(12) United States Patent
Garg et al.

(10) Patent No.: US 11,286,502 B2
(45) Date of Patent: Mar. 29, 2022

(54) ZIKA VIRUS LIKE PARTICLE (VLP) BASED VACCINE AND MICRONEUTRALIZATION ASSAY

(71) Applicant: Texas Tech University System, Lubbock, TX (US)

(72) Inventors: Himanshu Garg, El Paso, TX (US); Anjali Joshi, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 9 days.

(21) Appl. No.: 16/620,581

(22) PCT Filed: Jun. 20, 2018

(86) PCT No.: PCT/US2018/038551
§ 371 (c)(1),
(2) Date: Dec. 9, 2019

(87) PCT Pub. No.: WO2018/237039
PCT Pub. Date: Dec. 27, 2018

(65) Prior Publication Data
US 2020/0140891 A1    May 7, 2020

Related U.S. Application Data

(60) Provisional application No. 62/522,655, filed on Jun. 20, 2017.

(51) Int. Cl.
*C12N 15/86* (2006.01)
*C12N 7/00* (2006.01)
*C12Q 1/70* (2006.01)

(52) U.S. Cl.
CPC ............ *C12N 15/86* (2013.01); *C12N 7/00* (2013.01); *C12Q 1/70* (2013.01); *C12N 2740/15043* (2013.01); *C12N 2770/24122* (2013.01); *C12N 2770/24123* (2013.01); *C12N 2770/24134* (2013.01)

(58) Field of Classification Search
None
See application file for complete search history.

(56) References Cited

FOREIGN PATENT DOCUMENTS

| WO | 2016210127 A1 | 12/2016 |
| WO | 2017015463 A2 | 1/2017 |
| WO | 2018152526 A1 | 8/2018 |

OTHER PUBLICATIONS

Invitrogen pcDNA3.4-TOPO TA Cloning Kit, 2013, 29 pgs, from: https://www.thermofisher.com/document-connect/document-connect.html?url=https%3A%2F%2Fassets.thermofisher.com%2FTFS-Assets%2FLSG%2Fmanuals%2Fpcdna3_4_topo_ta_cloning_kit_man.pdf&title=cGNETkEzLjQtVE9QTyBUQSBDbG9uaW5nIEtpdCBVc2VyIEd1aWRl (Year: 2013).*
Dowd et al., Cell Reports, Aug. 9, 2016, 16:1485-1491, Supplemental Information, 13 pages, available from: https://ars.els-cdn.com/content/image/1-s2.0-S2211124716309809-mmc1.pdf (Year: 2016).*
Invitrogen ViraPower Lentiviral Expression System, 2002, 4 pages, available from: https://assets.thermofisher.com/TFS-Assets/LSG/brochures/710_021387_ViraPowerAnnounc.pdf (Year: 2002).*
NIH AIDS Reagent Program, Catalog No. 4692, dHP-dl-N/A, Feb. 14, 2019, 1 page from the attachments section at https://www.hivreagentprogram.org/Catalog/HRPPlasmidVectors/ARP-4692.aspx, accessed Aug. 30, 2021. (Year: 2019).*
Brien, JD, et al., "Propagation, quantification, detection, and storage of West Nile virus." Curr Protoc Microbiol (2013), 31:15D 3 1-15D 3 18.
Pugachev, KV, et al., "Double-subgenomic Sindbis virus recombinants expressing immunogenic proteins of Japanese encephalitis virus induce significant protection in mice against lethal JEV infection." Virology (1995), 212:587-94.
Rasmussen, SA, et al., "Zika Virus and Birth Defects—Reviewing the Evidence for Causality." N Engl J Med (2016), 374:1981-7.
Richner, JM, et al., "Modified mRNA Vaccines Protect against Zika Virus Infection." Cell (2017), 169:176.
Sapparapu, G, et al., "Neutralizing human antibodies prevent Zika virus replication and fetal disease in mice." Nature (2016), 540:443-447.
Shi, PY, et al., "Construction and characterization of subgenomic replicons of New York strain of West Nile virus." Virology (2002), 296:219-33.
Shi Y, Gao GF. "Structural Biology of the Zika Virus." Trends Biochem Sci (2017), doi:10.1016/j.tibs.2017.02.009.
Simpson, DI. "Zika Virus Infection in Man " Trans R Soc Trop Med Hyg (1964), 58:335-8.
Stadler, K, et al., "Proteolytic activation of tick-borne encephalitis virus by furin." J Virol (1997

(56) References Cited

OTHER PUBLICATIONS

Wilson, JR, et al., "West Nile virus nonstructural protein 1 inhibits TLR3 signal transduction." J Virol (2008), 82:8262-71.
Xing, YP, et al., "Novel DNA vaccine based on hepatitis B virus core gene induces specific immune responses in Balb/c mice." World J Gastroenterol (2005), 11:4583-6.
Yamshchikov, VF, et al., "Formation of the flavivirus envelope: role of the viral NS2B-NS3 protease." J Virol (1995), 69:1995-2003.
Zhao, H, et al., "Structural Basis of Zika Virus-Specific Antibody Protection." Cell (2016), 166:1016-27.
Boigard, H, et al., "Zika virus-like particle (VLP) based vaccine." PLoS Negl Trop (2017), Dis 11:e0005608.
Henchal, EA, et al., "Dengue virus-specific and flavivirus group determinants identified with monoclonal antibodies by indirect immunofluorescence." Am J Trop Med Hyg (1982), 31:830-6.
Pincus, S, et al., "Recombinant vaccinia virus producing the prM and E proteins of yellow fever virus protects mice from lethal yellow fever encephalitis." Virology (1992), 187:290-7.
Garg, H. et al., "Development of Virus-Like-Particle Vaccine and Reporter Assay for Zika Virus", Journal of Virology, Oct. 2017, vol. 91, Issue 20, e00834-17, pp. 1-16.
International Search Report and Written Opinion, ISA/AU [PCT/US2018/038551] Sep. 28, 2018.
Abbink, P, et al., "Protective efficacy of multiple vaccine platforms against Zika virus challenge in rhesus monkeys." Science (2016), 353:1129-32.
Aihara, H, et al., "Establishment and characterization of Japanese encephalitis virus-specific, human CD4(+) T-cell clones: flavivirus cross-reactivity, protein recognition, and cytotoxic activity." J Virol (1998), 72:8032-6.
Bera, AK, et al., "Functional characterization of cis and trans activity of the Flavivirus NS2B-NS3 protease." J Biol Chem (2007), 282:12883-92.
Brasil, P, et al., "Zika Virus Infection in Pregnant Women in Rio de Janeiro." N Engl J Med (2016), 375:2321-2334.
Cao-Lormeau, VM, et al., "Guillain-Barre Syndrome outbreak associated with Zika virus infection in French Polynesia: a case-control study." Lancet (2016), 387:1531-9.
Chahal, JS, et al., "An RNA nanoparticle vaccine against Zika virus elicits antibody and CD8+ T cell responses in a mouse model." Sci Rep (2017), 7:252.
Chambers, TJ, et al., "Flavivirus genome organization, expression, and replication." Annu Rev Microbiol (1990), 44:649-88.
Davidson, A, et al., "Suspected Female-to-Male Sexual Transmission of Zika Virus—New York City, 2016." MMWR Morb Mortal Wkly Rep (2016), 65:716-7.
Davis, BS, et al., "West Nile virus recombinant DNA vaccine protects mouse and horse from virus challenge and expresses in vitro a noninfectious recombinant antigen that can be used in enzyme-linked immunosorbent assays." J Virol (2001), 75:4040-7.
Dick, GW, et al., "Zika virus. I. Isolations and serological specificity." Trans R Soc Trap Med Hyg (1952), 46:509-20.
Dick, GW. "Zika virus. II. Pathogenicity and physical properties." Trans R Soc Trop Med Hyg (1952), 46:521-34.
Dowd, KA, et al., "Broadly Neutralizing Activity of Zika Virus-Immune Sera Identifies a Single Viral Serotype." Cell Rep (2016), 16:1485-91.
Dowd, KA, et al., "Genotypic Differences in Dengue Virus Neutralization Are Explained by a Single Amino Acid Mutation That Modulates Virus Breathing." MBio (2015), 6:e01559-15.
Dowd, KA, et al., "Rapid development of a DNA vaccine for Zika virus." Science (2016), 354:237-240.
Duenas-Carrera S, et al., "A truncated variant of the hepatitis C virus core induces a slow but potent immune response in mice following DNA immunization." Vaccine, 19:992-7, (2001).
Duffy, MR, et al., "Zika virus outbreak on Yap Island, Federated States of Micronesia." N Engl J Med (2009), 360:2536-43.
Enfissi, A, et al., "Zika virus genome from the Americas." Lancet (2016), 387:227-8.
Ferlenghi, I, et al., "Molecular organization of a recombinant subviral particle from tick-borne encephalitis virus." Mol Cell (2001), 7:593-602.
Gagnon, SJ, et al., "Identification of two epitopes on the dengue 4 virus capsid protein recognized by a serotype-specific and a panel of serotype-cross-reactive human CD4+ cytotoxic T-lymphocyte clones." J Virol (1996), 70:141-7.
Garg, H, et al., "HIV-1 adaptation to low levels of CCR5 results in V3 and V2 loop changes that increase envelope pathogenicity, CCR5 affinity and decrease susceptibility to Maraviroc." Virology (2016), 493:86-99.
Garg, H, et al., "Identification of conserved motifs in the West Nile virus envelope essential for particle secretion." BMC Microbiol (2013), 13:197.
Gehrke, R, et al., "Incorporation of tick-borne encephalitis virus replicons into virus-like particles by a packaging cell line." J Virol (2003), 77:8924-33.
Haddow, AD, et al., "Genetic characterization of Zika virus strains: geographic expansion of the Asian lineage." PLoS Negl Trop Dis (2012), 6:e1477.
Hasan, SS, et al., "A human antibody against Zika virus crosslinks the E protein to prevent infection." Nat Commun (2017), 8:14722.
Hayes, EB. "Zika virus outside Africa." Emerg Infect Dis (2009), 15:1347-50.
Hunt, AR, et al., "A recombinant particulate antigen of Japanese encephalitis virus produced in stably-transformed cells is an effective noninfectious antigen and subunit immunogen." J Virol Methods (2001), 97:133-49.
Jeong, H, Seong BL. "Exploiting virus-like particles as innovative vaccines against emerging viral infections." J Microbiol (2017), 55:220-230.
Joshi, A, et al., "HIV ENV glycoprotein-mediated bystander apoptosis depends on expression of the CCR5 co-receptor at the cell surface and ENV fusogenic activity." J Biol Chem (2011), 286:36404-13.
Khromykh, AA, et al., "Encapsidation of the flavivirus kunjin replicon RNA by using a complementation system providing Kunjin virus structural proteins in trans." J Virol (1998), 72:5967-77.
Kim, E, et al., "Preventative Vaccines for Zika Virus Outbreak: Preliminary Evaluation." EBioMedicine (2016), 13:315-320.
Kuno, G, Chang GJ. "Full-length sequencing and genomic characterization of Bagaza, Kedougou, and Zika viruses." Arch Virol (2007), 152:687-96.
Larocca, RA, et al., "Vaccine protection against Zika virus from Brazil." Nature (2016), 536:474-8.
Lazear, HM, Diamond MS. "Zika Virus: New Clinical Syndromes and Its Emergence in the Western Hemisphere." J Virol (2016), 90:4864-75.
Lazo, L, et al., "A recombinant capsid protein from Dengue-2 induces protection in mice against homologous virus." Vaccine (2007), 25:1064-70.
Lo, MK, et al., "Potential high-throughput assay for screening inhibitors of West Nile virus replication." J Virol (2003), 77:12901-6.
Lobigs, M. "Flavivirus premembrane protein cleavage and spike heterodimer secretion require the function of the viral proteinase NS3." Proc Natl Acad Sci U S A (1993), 90:6218-22.
Lorenz, IC, et al., "Intracellular assembly and secretion of recombinant subviral particles from tick-borne encephalitis virus." J Virol 77:4370-82, (2003).
Maeda, A and Maeda J. "Review of diagnostic plaque reduction neutralization tests for flavivirus infection." Vet J (2013), 195:33-40.
Mansuy, JM, et al., "Zika virus in semen and spermatozoa." Lancet Infect Dis (2016), 16:1106-7.
Mason, PW, et al., "Japanese encephalitis virus-vaccinia recombinants produce particulate forms of the structural membrane proteins and induce high levels of protection against lethal JEV infection." Virology (1991), 180:294-305.
Murray, KO, et al., "Prolonged Detection of Zika Virus in Vaginal Secretions and Whole Blood." Emerg Infect Dis (2017), 23:99-101.
Noad, R, Roy P. "Virus-like particles as immunogens." Trends Microbiol (2003), 11:438-44.

(56) References Cited

OTHER PUBLICATIONS

Oehler, E, et al., "Zika virus infection complicated by Guillain-Barre syndrome—case report, French Polynesia, December" Euro Surveill (2014), 19.

Oliveira, ER, et al., "The flavivirus capsid protein: Structure, function and perspectives towards drug design." Virus Res (2017), 227:115-123.

Pardi, N, et al., "Zika virus protection by a single low-dose nucleoside-modified mRNA vaccination." Nature (2017), 543:248-251.

Pattenden, LK, et al., "Towards the preparative and large-scale precision manufacture of virus-like particles." Trends Biotechnol (2005), 23:523-9.

Pierson, TC, et al., "A rapid and quantitative assay for measuring antibody-mediated neutralization of West Nile virus infection." Virology (2006), 346:53-65.

Pijlman, GP. "Enveloped virus-like particles as vaccines against pathogenic arboviruses." Biotechnol J 10:659-70, (2015).

* cited by examiner

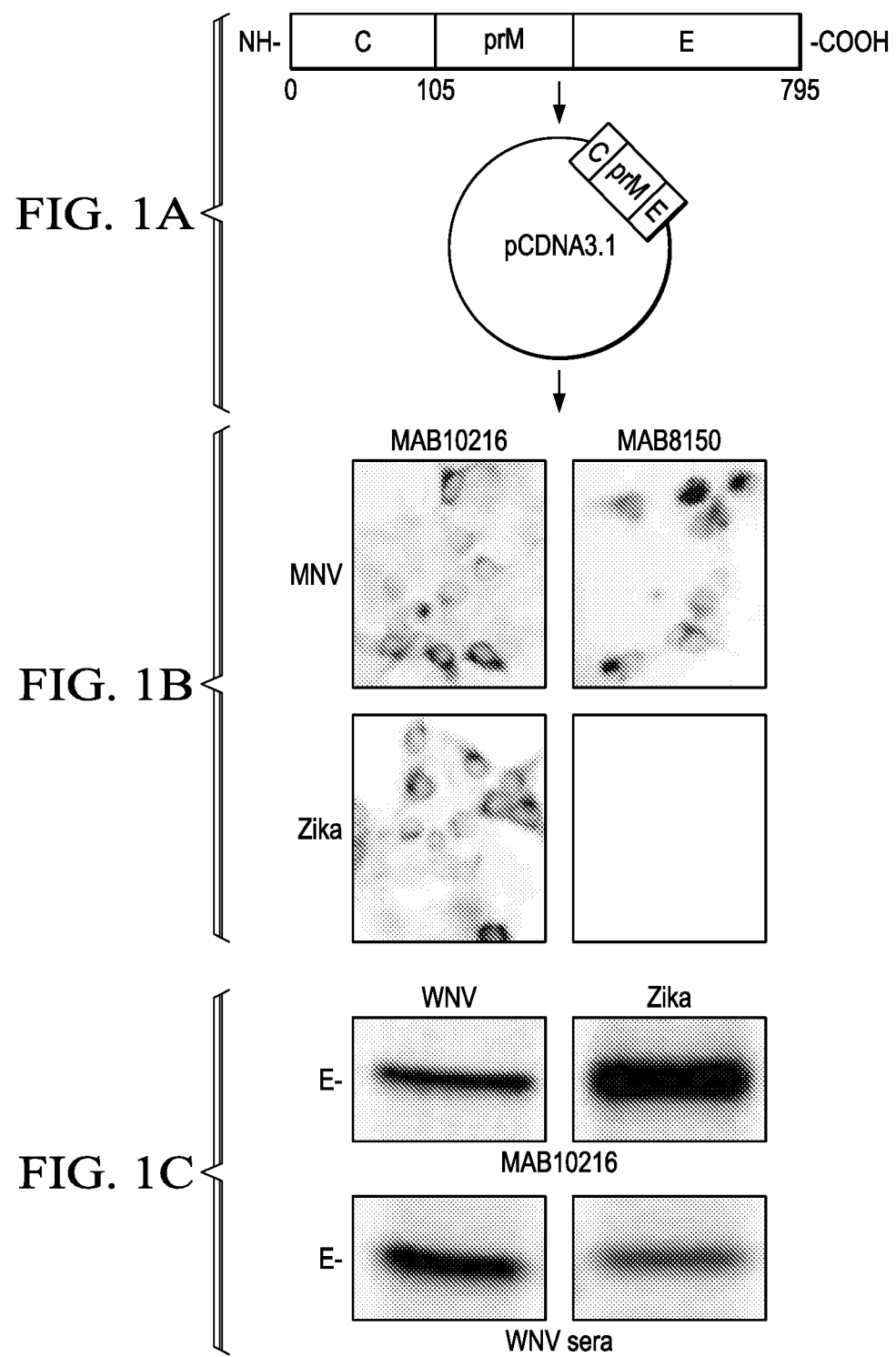

FIG. 2D

No. GFP+ cells vs Zika VLP (µl)

X-axis: 25, 12.5, 6.25, 3.125, 1.56, 0.78, 0.39, 0.195, 0.097

FIG. 2E

No. GFP+ cells vs WNV VLP (µl)

X-axis: 25, 12.5, 6.25, 3.125, 1.56, 0.78, 0.39, 0.195, 0.097

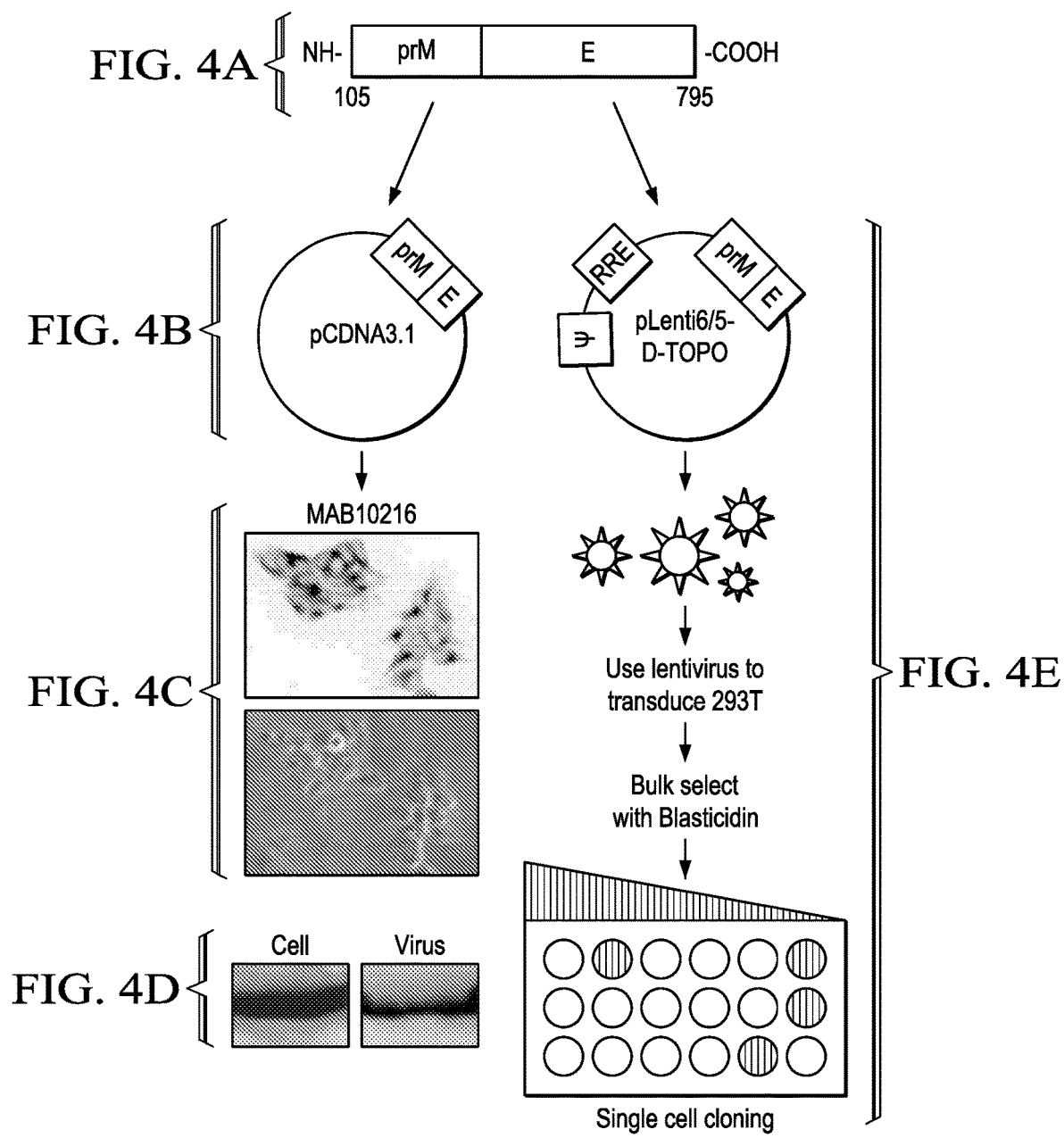

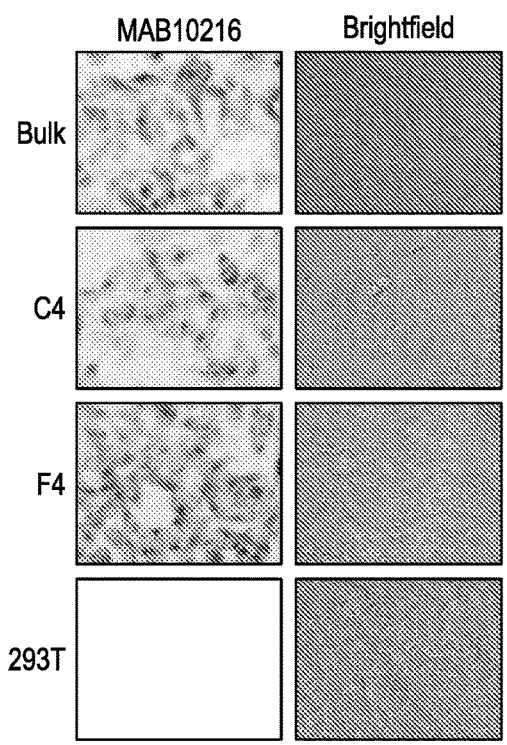
FIG. 4F
FIG. 4G
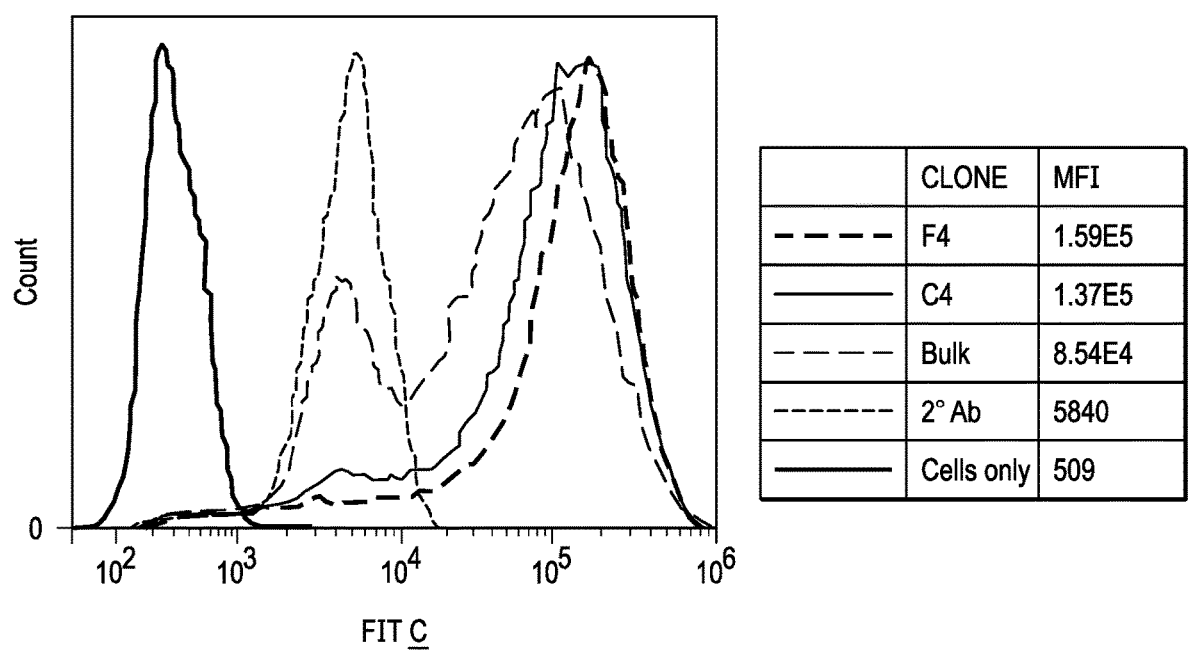

| GROUP | INJECTION | ROUTE | VOLUME | AMOUNT |
|---|---|---|---|---|
| 1 | prM-E DNA | i.m. Right & left thigh | 50 µl | 50µg/mice |
| 2 | C-prM-E DNA | i.m. Right & left thigh | 50 µl | 50µg/mice |
| 3 | prM-E VLPs | i.m. Right & left thigh | 50 µl | 1:1 mix with Titer Max Gold |
| 4 | C-prM-E VLPs | i.m. Right & left thigh | 50 µl | 1:1 mix with Titer Max Gold |
| 5 | PBS | i.m. Right & left thigh | 50 µl | 50 µl |

ZIKA VIRUS LIKE PARTICLE (VLP) BASED VACCINE AND MICRONEUTRALIZATION ASSAY

CROSS-REFERENCE TO RELATED APPLICATIONS

This application is the National Stage of International Application No. PCT/US2018/038551, filed on Jun. 20, 2018, which claims priority to U.S. Patent Appl. Ser. No. 62/522,655, filed Jun. 20, 2017, the content of each of which is incorporated by reference herein.

STATEMENT OF FEDERALLY FUNDED RESEARCH

This invention was made with government support under 1R21A1131696-01 awarded by the National Institutes of Health. The government has certain rights in the invention.

TECHNICAL FIELD OF THE INVENTION

The present invention relates in general to the field of a ZIKA virus like particle (VLP) based vaccine and microneutralization assay, cell lines, and vectors related to the same.

INCORPORATION-BY-REFERENCE OF MATERIALS FILED ON COMPACT DISC

The present application includes a Sequence Listing, which has been submitted in ASCII format via EFS-Web and is hereby incorporated by reference in its entirety. Said ASCII copy, created on Jun. 20, 2018, is named TECH2104WO_SeqList and is 53 kilobytes in size.

BACKGROUND OF THE INVENTION

Without limiting the scope of the invention, its background is described in connection with viruses belonging to the family Flaviviridae.

Since the identification of Zika virus (ZIKV) in 1947 from a Rhesus Monkey in Uganda until 2010, the virus has predominantly circulated between Aedes mosquitoes and non-human primates. Periodic episodes have been identified in the human population, which were characterized by mild self-limiting febrile disease associated with rash, headache, myalgia and conjunctivitis. However, the recent spread of ZIKV infections in the Western continents has caused much concern due to severe clinical outcome in unborn fetuses including cerebral calcifications, microcephaly and other severe congenital malformations. In adults, neurological manifestations are characterized by an autoimmune condition with symptoms of neuropathy and paralysis, also known as the Guillain-Barre syndrome. While Aedes species of mosquitos are the most common source of transmission, the virus has also been shown to transmit sexually both from women to men and men to women and is capable of persisting in semen and vaginal secretions for up to 6 months after infection.

ZIKV is an enveloped RNA virus belonging to the family Flaviviridae. The 11 Kb positive sense RNA genome is translated in the cytoplasm to generate three structural and seven non-structural proteins. The structural proteins C (Capsid), prM/M (Pre-membrane, membrane), and E (Envelope) aid in virus assembly that predominantly occurs in the lumen of the endoplasmic reticulum (ER). Virus maturation occurs during virus egress via the secretory pathway when the acidic environment in the Golgi cleaves the prM followed by release of pr peptide. The E protein is the major target for neutralizing antibodies and monoclonal antibodies against all 3 E protein domain (DI, DII and DIII) target epitopes have been found. The recent outbreaks of ZIKV infection have sparked efforts in the scientific community towards the development of a safe and effective vaccine. These efforts towards a safe and efficacious vaccine encompass the use of established approaches like purified inactivated virus to more advanced approaches like DNA (Pr-M-E), subunit (E) based vaccines, recombinant adenoviral platforms along with recent development of RNA nanoparticle technology, or modified mRNA (prM-E) as vaccine candidates. The studies have demonstrated a neutralizing antibody response capable of protecting against ZIKV infection both in mice and non-human primates leading several clinical trials currently underway (NCT02963909, NCT02840487, NCT02887482, NCT02809443, NCT02952833). One of the advantages of the development of a ZIKV vaccine is that even though the virus exists as two distinct lineages (the African and Asian/American), the immune response generated against the virus is broadly protective thus obviating the need to incorporate different serotypes in the vaccine.

What is needed is the development of neutralizing antibodies against the infection and availability of a rapid accurate diagnostic assay to quantitate the elicited immune response. A widely used assay for detection of neutralizing antibodies against Flaviviruses is the plaque reduction neutralization test (PRNT) assay, which involves the use of live virus handled under BSL-2 conditions. An ideal assay would be one that could be adapted to a high throughput format with a convenient read out and eliminate the use of live virus making it readily available to laboratories worldwide. With regards to an effective vaccine, the priorities include: safety, efficacy, ease of handling, and economy of production for worldwide dissemination.

Thus, despite many efforts, there is currently no approved vaccine for Zika. A recent report showed a PrME plasmid DNA vaccine to be effective in mouse studies. However, DNA based vaccines includes several risks, e.g., insertional mutagenesis.

SUMMARY OF THE INVENTION

In one embodiment, the present invention includes a nucleic acid vector comprising: a recombinant nucleic comprising at least one of: a Zika virus C-prM-E gene, or a recombinant nucleic comprising a portion of a prM-E gene region of Zika virus spanning amino acids 105-795, operably linked to a promoter. In one aspect, the nucleic acid vector is a flavivirus vector. In another aspect, the nucleic acid vector is a plasmid. In another aspect, the C-prM-E, the prM-E gene, or both are codon optimized. In another aspect, the nucleic acid vector is pcDNA3.1™, and the C-prM-E gene, the prM-E gene, or both, are codon optimized for expression in human cells. In another aspect, the nucleic acid vector further comprises an NS2B3 protease gene. In another aspect, the vector is a lentiviral vector pLenti6/5-D-Topo®. In another aspect, the vector further comprises an NS2B3 protease gene. In another aspect, the nucleic acid vector further comprising a selectable marker.

In another embodiment, the present invention includes a method of making a Zika virus Reporter Virus Particles (RVP) comprising: transfecting cells stably expressing a Zika C-prM-E gene; and transfecting the cells stably with a sub-genomic replicon derived from lineage II strain of WNV that also expresses a reporter gene; incubating the cells under conditions in which the proteins are expressed for a period sufficient to form RVPs; and harvesting the RVPs. In one aspect, cells are 293T cells, HeLa cells, MDCK cells, Vero cells, or vaccine-certified cell lines. In another aspect, the reporter gene is selected from at least one of green fluorescent protein; yellow fluorescent protein; blue fluorescent protein; Cerulean fluorescent protein; Cyan fluorescent protein; red fluorescent protein from *Zooanthus* sp.; red fluorescent protein from Entremacaea quadricolor (RFP), or flavin mononucleotide (FMN)-binding fluorescent proteins (FbFPs). In another aspect, the C-prM-E is codon optimized. In another aspect, the method further comprises transfecting an NS2B3 protease gene into the cell. In another aspect, the vector further a selectable marker and selecting stable expression with a selectable marker.

In another embodiment, the present invention includes a vaccine comprising: a particle that comprises a codon optimized PrM-E protein of Zika virus in a pharmaceutically acceptable carrier or excipient. In one aspect, the particles are manufactured in 293T cells, HeLa cells, MDCK cells, Vero cells, or vaccine-certified cell lines. In another aspect, the particle is a Zika virus like particle. In another aspect, the vector further comprises a selectable marker. In another aspect, the particle is a Zika virus reporter virus particle capable of a single round infection in cells in a manner identical to native Zika virus. In another aspect, the Zika virus reporter virus particle is non-infectious.

In yet another embodiment, the present invention includes a vaccine comprising: a Zika virus like particle comprising a matured C-prM-E expressed from a vector that comprises a codon optimized C-prM-E gene and an NS2B3 protease gene.

In another embodiment, the present invention includes a cell line comprising: a codon optimized C-prM-E gene of Zika virus that is stably expressed. In one aspect, the cell line comprises 293T, Raji, or Vero cells. In another aspect, the cell line is transduced with Lentiviral particles made in cells expressing lentiviral prME and php-dl-NA, and VSVG Env. In another aspect, the cell line is stably transduced selected using a selectable marker. In another aspect, the stable expression is by blasticidin selection. In another aspect, the cell line is further transfected with an NS2B3 protease gene.

In another embodiment, the present invention includes a cell line comprising: a codon optimized prM-E gene region of Zika virus spanning amino acids 105-795 that is stably expressed. In one aspect, the cell line is 293T cells, HeLa cells, MDCK cells, Vero cells, or vaccine-certified cell lines.

In another embodiment, the present invention includes a method of detecting Zika virus microneutralization using reporter virus particles (RVP) or Virus Like Particles (VLP) comprising: (a) incubating serial dilutions of sera or antibodies with a pre-determined amount of ZIKV RVPs or VLPs comprising a detectable marker at room temperature to make an antibody-RVP mix; (b) adding the antibody-RVP or VLP mix to cells under conditions in which the detectable marker is expressed; (c) measuring infection after a pre-determined amount of time by counting the number of detectable marker positive cells; and (d) comparing the level of the detectable marker in a first set of cells where no sera or neutralizing antibody was used to a second set of cells where the sera or neutralizing antibodies were used, wherein a decrease in the number of marker positive cells in the second set of cells when compared to the first set of cells is indicative of microneutralization that correlates to a level of neutralizing antibodies in the biological sample of the patient. In one aspect, the cells are 293T, Raji, or Vero cells.

In another aspect, the method further comprises obtaining another biological sample from the patient after a pre-determined time and comparing a titer of neutralizing antibodies between an earlier and a later biological sample to determine antibody titers. In another aspect, the method is adapted for use in 4, 6, 8, 12, 24, 48, 96, 384, 1538, 6114, or 9,600 well plates. In another aspect, the ZIKV VLPs comprise a PrM-E protein expressed by a codon-optimized construct. In another aspect, the detectable marker in the ZIKV RVPs comprises a fluorescent protein expressed in conjunction with a WNV sub-genomic replicon. In another aspect, the ZIKV VLP is adapted to be an antigen in a diagnostic assay.

In another embodiment, the present invention includes a method of making stably transduced cell lines comprising: transfecting cells with lentiviral vector expressing ZIKV prME, CprME, or both prME and CprME, and php-dl-NA and VSVG Env to produce Lentiviral particles; transducing cells with the Lentiviral particles; and selecting stable transduced cells with a selection agent to create the stably transduced cell lines. In one aspect, the cell line is prME-F4. In another aspect, the cell line is CprME (F6). In another aspect, the selection agent is Blasticidin. In another aspect, the transfected cells are selected from 293T cells, HeLa cells, MDCK cells, Vero cells, or vaccine-certified cell lines. In another aspect, the ZIKV prME, CprME, or both prME and CprME are codon optimized.

In another embodiment, the present invention includes a reporter Zika virus Reporter Virus Particles (RVP) made by expressing a matured, codon optimized ZIKV CprME made in a cell line that expressed an NS2B3 protease.

BRIEF DESCRIPTION OF THE DRAWINGS

For a more complete understanding of the features and advantages of the present invention, reference is now made to the detailed description of the invention along with the accompanying figures and in which:

FIGS. 1A to 1C show the expression of ZIKV C-prM-E using codon optimized synthetic construct. (FIG. 1A) A codon optimized ZIKV C-prM-E gene was synthesized via gene synthesis technology using the sequence available from the current outbreak in Americas and cloned into the pcDNA3.1 vector. (FIG. 1B) 293T cells were transfected with the ZIKV C-prM-E or WNV C-prM-E constructs. Cells were fixed, stained with antibodies MAB10216 and MAB8150 followed by analysis of E protein expression by fluorescence microscopy. (FIG. 1C) 293T cells were transfected as described above. Forty eight hours post transfection, cells were radiolabeled with [$^{35}$S]Met/Cys. Cell lysates were immunoprecipitated with ProteinA beads coated with MAB10216 or anti-WNV serum, resolved by SDS-PAGE followed by PhosphorImager analysis.

FIGS. 2A to 2H show RVP based microneutralization assay for ZIKV using a 96 well plate format and GFP readout. (FIG. 2A) Strategy for generation of ZIKV or WNV reporter virus particles. 293T cells were co-transfected with ZIKV/WNV C-prM-E along with the WNV subgenomic replicon construct Rep/GFP. Culture supernatants were harvested 48 h post transfection, used to infect 293T/Vero cells and GFP expression was analyzed as a measure of virus infection. (FIG. 2B) 293T and Vero cells were infected with ZIKV or WNV RVPs and infection analyzed by fluorescence microscopy as GFP positive cells. (FIG. 2C) Vero cells were infected with serial dilutions of ZIKV reporter virus like particles in 96-well plates. Cells were fixed 72 h post infection and images of whole wells captured via fluorescence microscopy. Representative fluorescent images of whole wells infected with 6 serial dilutions (dilution 1-6) of ZIKV RVPs is depicted. The top panel shows raw images acquired by fluorescent microscopy. The bottom panel shows the same images analyzed using the automated NIS elements software that marks the GFP positive cells using the cell count function. Numbers below each well represent the number of GFP positive cells in that well. Vero cells were infected with serial dilutions of (FIG. 2D) ZIKV or (FIG. 2E) WNV reporter virus particles in 96-well plates. The experiment was conducted with 6 technical wells infected for each dilution. Number of GFP positive cells was determined 72 h post infection as described in part C above. Data shows small variations between the 6 wells for each RVP dilution. (FIG. 2F) Quantitation of GFP positive cells infected with Zika RVPs using the automated software from Nikon versus manual counting. Representative data shows high degree of correlation between the two methods. (FIG. 2G) ZIKV-117 antibody or (FIG. 2H) the indicated antibodies/sera were serially diluted in DMEM and incubated with a predetermined amount of ZIKV RVPs for 1 h at room temperature. Subsequently, the virus: sera mix was added to Vero cells. The cells were incubated for 72 h following which images were acquired and the number of GFP positive cells quantitated as described above. The assay was conducted in technical triplicates for the ZIKV-117 antibody and ZIKV sera and in duplicates for others. One representative of 3 independent experiment is shown.

(FIG. 3A) The ZIKV C-prM-E was PCR amplified with specific primers using the codon optimized construct as template and cloned into the lentiviral vector with a directional Cloning site, Rouse Sarcoma Virus (RSV) enhancer/promoter, Modified HIV-1 5' and 3' Long Terminal Repeats (LTR), HIV-1 psi ($\psi$), HIV Rev response element (RRE), (CMV) immediate early promoter, C-terminal V5 epitope, Blasticidin (bsd) resistance gene, Ampicillin resistance gene, and pUC origin of replication, such as, pLenti6/5-D-Topo. 293T cells were then transfected with the pLenti-C-prM-E construct along with the helper plasmid and VSV-G envelope and ZIKV-C-prM-E lentiviral particles harvested 48 h post transfection. 293T cells were then transduced with the above lentiviral particles and cells selected by culturing in the presence of Blasticidin. Bulk selected cells were confirmed for E protein expression via immunofluorescence. Subsequently, cells were plated in 96 well plates using limiting dilution and clones arising from single viable cells selected. (FIG. 3B) 293T cells transduced with ZIKV C-prM-E lentiviral particles and bulk selected with Blasticidin were stained with antibody MAB10216 and analyzed by fluorescence microscopy. (FIG. 3C) The percentage of C-prM-E positive cells was determined by flow cytometry. The cells only peak represents 293T cells not stained with the antibody and the 293T peak represents 293T cells stained with MAB10216. (FIG. 3D) 293T cells expressing the pLenti-ZIKV-C-prM-E generated above and bulk selected with blasiticidin were analyzed for E protein expression by western blotting. Non transfected 293T cells (293T) or cells transiently transfected with the ZIKV C-prM-E expression construct (transient) were used as negative and positive controls respectively. (FIG. 3E) Single cells clones of 293T cells expressing the pLenti-ZIKV-C-prM-E were stained using antibody MAB10216 and analyzed by fluorescence microscopy or (FIG. 3F) Flow cytometry. The Mean Fluorescent Intensity (MFI) of E protein expression for each clone is indicated alongside. (FIG. 3G) The pLenti-ZIKV-C-prM-E 293T cells are ideal for producing high titer RVPs. 293T cells were transiently transfected with ZIKV C-prM-E along with the WNV Rep/GFP construct to generate reporter virus particles. Alongside, the pLenti-ZIKV-C-prM-E cell line was transfected with the WNV Rep/GFP construct. RVPs were harvested and serial dilutions used to infect Vero cells. Number of GFP positive cells in each well was quantitated by fluorescent microscopy. Error bars are mean+/−SD. *represents significant difference (p<0.01) in number of GFP+ cells in 293T versus C-prM-E-F6 RVPs using the unpaired t-test. One representative of 4 independent experiments is shown.

FIGS. 4A to 4H shows the generation of prM-E cell line for VLP production. (FIG. 4A) The ZIKV prM-E was PCR amplified with specific primers using the codon optimized C-prM-E construct as template and cloned into a vector having a Cytomegalovirus (CMV) enhancer-promoter, multiple cloning site, Bovine Growth Hormone (BGH) polyadenylation signal and transcription termination sequence, SV40 origin, ampicillin resistance gene and pUC origin of replication, such as the (FIG. 4B) pCDNA3.1 expression vector. (FIG. 4C) E protein expression was determined by fluorescence microscopy after staining with antibody MAB10216. (FIG. 4D) Culture supernatants were harvested from ZIKV prM-E expressing cells and ultracentrifuged. Cell and virus pellet was lysed and E protein expression determined by western blotting. (FIG. 4E) The ZIKV prM-E was PCR amplified and cloned into the lentiviral vector pLenti6/5-D-Topo. 293T cells were then transfected with the pLenti-prM-E construct along with the helper plasmid and VSV-G envelope and ZIKV-prM-E lentiviral particles harvested 48 h post transfection. 293T cells were then transduced with the above lentiviral particles and cells either bulk selected or as single cell clones by culturing in the presence of Blasticidin. (FIG. 4F) Selected cells were confirmed for E protein expression via immunofluorescence and (FIG. 4G) Fluorescence microscopy after staining with antibody MAB10216. The mean Fluorescent Intensity (MFI) of E protein expression for each prM-E clone is indicated alongside. (FIG. 4H) The indicated pLenti-ZIKV-prM-E cell clones were seeded in equal cell numbers and culture supernatants harvested and ultracentrifuged. VLP pellets were lysed, resolved by SDS-PAGE and E protein expression determined by western blotting.

(FIG. 5A) 293T cells were transfected with the pCDNA3.1 vector expressing the ZIKV prM-E or C-prM-E along with the indicated expression vectors. Cells were radiolabeled with [$^{35}$S]Met/Cys and culture supernatants harvested and ultracentrifuged. Cell and virion samples were lysed and immunoprecipitated with MAB10216 coated ProteinA beads, resolved by SDS-PAGE followed by PhosphorImager analysis. (FIG. 5B) Culture supernatants were harvested from cells expressing the ZIKV C-prM-E or prM-E as indicated in the methods. 25-30 ml of supernatant was transferred into ultracentrifuge tubes and carefully underlayed with 5 ml of 25% glycerol in TNE buffer. VLPs were pelleted by centrifugation at 110,500×g for 3 h at 4° C. Thereafter, the supernatant was carefully removed and the VLP pellet resuspended in TNE buffer. An aliquot of the concentrated VLPs were lysed using 10× RIPA buffer and E protein in the preps was detected by western blotting. (FIG. 5C) VLPs were concentrated as above and images were acquired after negative staining using the Transmission Electron Microscope JEOL1010 with a Hamamatsu digital camera. Scale Bar~30 nm. Immunization studies in mice. (FIG. 5D) Balb/c mice were divided into groups of six mice each. Mice received primary immunization on day 0 followed by 2 boosters at day 14 and 28 and were finally sacrificed at day 63 post primary immunization. (FIG. 5E) Mice were divided into 5 groups and received immunizations with either C-prM-E/prM-E DNA or VLPs. For DNA immunization, a total of 50 µg of DNA in a volume of 100 µl PBS was injected intramuscularly. For VLPs, the first immunization consisted of VLP prep mixed with TiterMax Gold adjuvant in total volume of 100 µl injected intramuscularly. For subsequent boosters, mice received VLPs alone without adjuvant. Control mice were sham injected with PBS.

(FIG. 6A) Serum samples collected from different groups of immunized mice were used in the reporter RVP based microneutralization assay. Sera sample from each mouse was serially diluted in DMEM and incubated with a predetermined amount of ZIKV RVPs for 1 h at room temperature. All samples were assayed in technical duplicates. Subsequently, the virus: sera mix was added to Vero cells in 96-well plates. The cells were incubated for 72 h following which the plates were fixed and images acquired as described in FIGS. 2A-2H. Curves were fit using the GraphPad Prism software and neutralizing antibody (FIG. 6B) EC50 and (FIG. 6C) EC90 values calculated. Statistical analysis was performed using the unpaired t test. Significant difference in EC50 ($p=0.0083$) and EC90 values ($p=0.0006$) between the prM-E and C-prM-E VLP immunized mice. The dotted line denotes the limit of detection for the RVP assay (defined as the highest concentration of sera used in the neutralization experiments). Samples with titers<20 are reported at half the limit of confidence (1:10). Neutralization data form one of two independent repeats is shown. (FIG. 6D) Neutralization of a clinical ZIKV isolate PRVABC59 with immune sera samples from mice. Pooled sera samples from each immunized group were serially diluted in serum free media as in part (A) and incubated with a predetermined amount of ZIKV for 2 h at 37° C. All samples were assayed in technical duplicates. Subsequently, the virus: sera mix was added to Vero cells in 96-well plates. The cells were incubated for 48 h following which the plates were stained using MAB10216. Images were acquired as described in FIG. 2, antibody positive cells quantitated and curves were fit using the GraphPad Prism software. (FIG. 6E) Protein A beads were coated with 3 µl or 0.6 µl of pooled sera samples from each group of immunized mice. The antibody coated beads were then incubated with radiolabeled cell lysates derived from C-prM-E expressing cells. Cell lysates were resolved on an SDS-PAGE gel followed by phosphorImager analysis. The Photo Stimulated Luminescence (PSL) values for each band are depicted in the graphs underneath. (FIG. 6F) Pooled sera samples from each group of immunized mice were used in technical duplicates to determine inhibition of WNV RVPs as in part (A) above.

DETAILED DESCRIPTION OF THE INVENTION

Figure 2A:
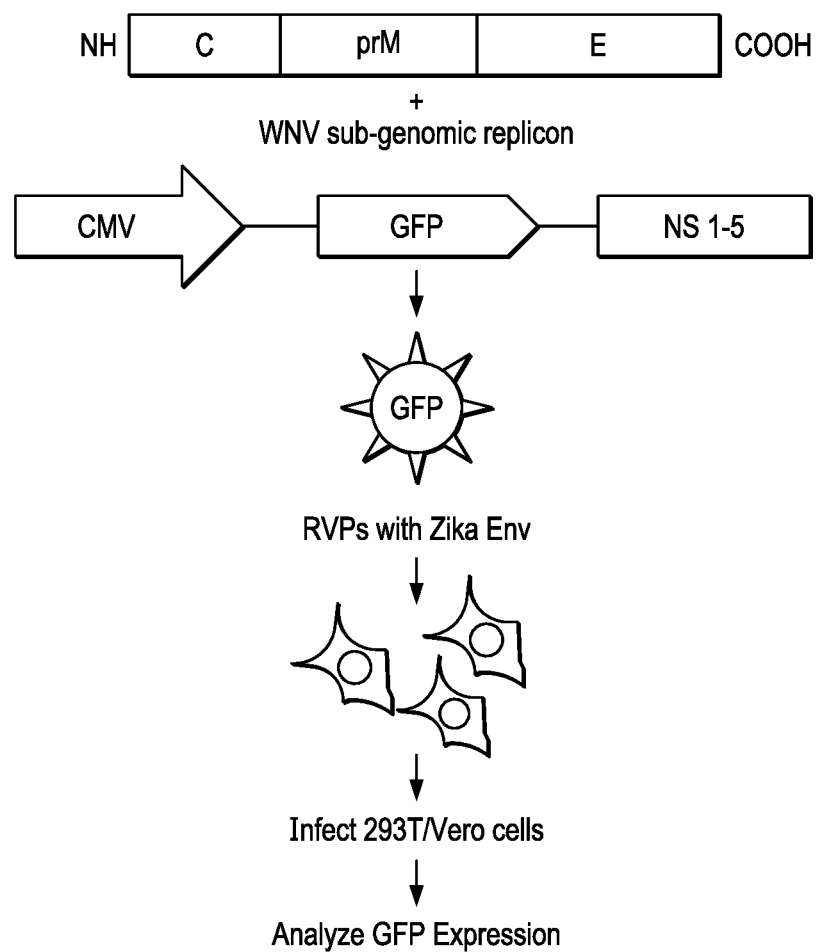

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention meets the criteria for an effective vaccine, namely, safety, efficacy, ease of handling, and economy of production for worldwide dissemination. The VLPs-based vaccines of the present invention are safe for manufacturing and handling and generate an effective immune response and can be readily scaled up for cost-effective production. The ZIKV VLPs taught herein can be readily produced in cells expressing the prM-E proteins and the particles although non-infectious resemble the live virus in morphology. Further, addition of the Capsid has been shown to promote virion stability and is effective in inducing a cell-mediated immune response against Flaviviruses. VLP-based vaccines have been successful against viral diseases like Hepatitis B (GlaxoSmithKline's ENGERIX® and Merck and Co., Inc.'s RECOMBIVAX HB®) and human papilloma virus (Merck and Co., Inc.'s GARDISIL®) with others in the pipeline for diseases like influenza, Parvovirus, Norwalk virus etc.

As used herein, the terms "antigen," "antigenic," and "antigenically active," refer to any substance that can be recognized by a specific humoral and/or cell-mediated immune response. As used herein, the terms "immunogen," "immunogenic" and "immunologically active" refer to any substance that is capable of inducing a specific humoral and/or cell-mediated immune response. An antigen or immunogen generally contains at least one epitope. Antigens and immunogens include but are not limited to molecules, including small molecules, peptides, polysaccharides, nucleic acids, and/or lipid, that trigger an immune response. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves. In certain aspects, the virus like particles of the present invention can be used as an antigen in a diagnostic assay.

As used herein, the term "adjuvant" refers to the addition of an agent that enhances an immune response in an animal. For example, the antigen may be mixed or emulsified in saline, for example, Freund's complete adjuvant ("FCA"), Freund's incomplete adjuvant, alum, CpG, and the mixture is injected parenterally, intraperitoneally, subcutaneously, intramuscularly, orally, etc. The animal is generally boosted 2-6 weeks later with one or more injections of the antigen with or without an adjuvant. Antibodies may also be generated by in vitro immunization, using methods known in the art. When isolated from an animal, polyclonal antisera is then obtained from the immunized animal.

As used herein, the term "cell culture" refers to any in vitro culture of cells, including, e.g., continuous cell lines (immortal), primary cell cultures, transformed cell lines, finite cell lines (e.g., non-transformed cells), and any other cell population capable of being maintained in vitro. Cells may include bacterial, fungal, mammalian, insect, etc.

As used herein, the term "codon optimized" refers to a nucleic acid sequence or polynucleotides that is expressed into a polypeptide wherein the codon usage is optimized for a specific host. Codon optimized sequences are engineered to increase the expression of the polypeptide in a given species. To provide optimized polynucleotides coding for the viral and other proteins described herein, the DNA sequence of the gene is modified to 1) include codons preferred by highly expressed genes in a particular species; 2) include an A+T or G+C content in nucleotide base composition to that substantially found in the target species; 3) form an initiation sequence of the target species; or 4) eliminate sequences that cause destabilization, inappropriate polyadenylation, degradation and termination of RNA, or that form secondary structure hairpins or RNA splice sites. Increased expression of the proteins described herein is achieved by using a distribution frequency of codon usage in eukaryotes and prokaryotes, or in a particular species. The term "frequency of codon usage" refers to the usage of nucleotide codons found in a specific host cell to express a given amino acid. There are 20 natural amino acids, most of which are specified by more than one codon. Therefore, all degenerate nucleotide sequences can be codon optimized so as long as the amino acid sequence of the polypeptide encoded by the nucleotide sequence is functionally unchanged.

As used herein, the term "gene" refers to a nucleic acid (e.g., DNA or RNA) sequence that comprises coding sequences necessary for the production of a polypeptide, polypeptide precursors, or RNA (e.g., rRNA, tRNA, RNAi). The polypeptide can be encoded by a full length coding sequence or by any portion of the coding sequence so long as the desired activity or functional properties (e.g., immunogenicity) of the full-length or fragment are retained. The term can also encompasses the coding region of a structural gene and the sequences located adjacent to the coding region on both the 5' and 3' ends on either end such that the gene corresponds to the length of the full-length mRNA, e.g., when engineered into a nucleic acid vector. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene, e.g., a viral genome. A genomic form or clone of a gene contains the coding region interrupted with non-coding sequences termed "introns" or "intervening regions" or "intervening sequences." Introns are segments of a gene that are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment, e.g., a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "host cell" refers to any cell capable of replicating and/or transcribing and/or translating a heterologous gene. Thus, a "host cell" refers to any eukaryotic or prokaryotic cell (e.g., such as 293T, Raji, or Vero cells, or bacterial cells, E. coli, yeast cells, mammalian cells, avian cells, amphibian cells, plant cells, fish cells, and insect cells), whether located in vitro or in vivo.

As used herein, the term "in vitro" refers to events that occur in an artificial environment, e.g., in a plate, well, test tube or reaction vessel, in cell culture, etc., rather than within a multi-cellular organism or tissue.

As used herein, the term "in vivo" refers to events that occur within a multi-cellular organism. For example only and not meant to be limiting, such as a mammal more particularly a human and/or non-human animal.

As used herein, the term "nucleic acid sequence" refers to an oligonucleotide, a nucleotide or a polynucleotide, and fragments or portions thereof, including, DNA or RNA of genomic or synthetic origin, which may be single or double-stranded, and represent the sense or antisense strand. As used herein, the term "amino acid sequence" as used herein refers to peptide or protein sequence.

As used herein, the terms "operably linked", "in operable combination," or "in operable order," refer to the linkage of a nucleic acid sequence in such a manner that a nucleic acid molecule capable of directing the transcription of a given gene and/or the synthesis of a desired protein molecule is produced. The terms also refer to the linkage of amino acid sequences in such a manner so that a functional protein is produced.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "purified" refers to molecules, either polynucleotides or polypeptides that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the term "purified" refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, the term "reporter gene" refers to a gene that, when expressed as a protein, produces a polypeptide that is capable of being identified in an assay. One example of a reporter gene includes that are fluorescent, e.g., luciferase, green fluorescent protein, red fluorescent protein, that can be visually identified (e.g. with marked probes or antibodies) as known to those skilled in the art. Further, while specific examples are given any other means of fluorescent, bioluminescent, luminescent, and related reporter proteins useful for tracking are contemplated by the present invention. Other reporter genes include enzymes that can be used to metabolize or perform a reaction that creates a change in color (β-galactosidase) or the presence of a new metabolite (e.g., acetylation of chloramphenicol). Non-limiting examples of fluorescent proteins include: green fluorescent protein (GFP) PDB designation 1GFL; yellow fluorescent protein (YFP) PDB designation 3DPW; blue fluorescent protein (BFP) PDB designation 1BFP; Cerulean fluorescent protein (CFP) PDB designation 2WSO; Cyan fluorescent protein (CFP) PDB designation 2WSN; red fluorescent protein from Zooanthus sp. (RFP) PDB designation 2ICR; red fluorescent protein from Entremacaea quadricolor (RFP) PDB designation 2PJB, flavin mononucleotide (FMN)-binding fluorescent proteins (FbFPs).

As used herein, the term "subject" or "patient" refers to any organism immunized with the nucleic acid constructs, polypeptides, cells, or Reporter Virus Particles (RVP) invention are administered, e.g., for experimental, diagnostic, prophylactic, and/or therapeutic purposes. Typical subjects include animals (e.g., mammals such as mice, rats, rabbits, non-human primates, and humans; insects; worms; etc.). In vitro systems may also be used (e.g. to express ZIKV proteins or portions thereof for study within the target cell and/or for isolation).

As used herein, the term "vaccine" refers to an immunogenic composition that is administered to a host to provide some degree of protection from an infection and/or disease from a target virus or pathogen, e.g., ZIKV. Immunogenic agents are those that trigger an immune response in an animal. Moreover, some degree of protection includes but is not limited to decreasing, reducing, modifying, and/or ameliorating one or more symptoms of an infection and/or disease.

Vaccines can be administered alone or in combination with various adjuvants/carriers. Pharmaceutical carriers for immunization are known to those skilled in the art. These most typically would be standard carriers for administration of vaccines to humans, including solutions such as sterile water, saline, and buffered solutions at physiological pH. Other ingredients can include, e.g., adjuvants, excipients, carriers, thickeners, diluents, buffers, preservatives, and surface-active agents.

As used herein, the term "vaccine-certified cells", refers to those cell lines that are routinely used for vaccine manufacturing purposes. A certification process is used, e.g., that taught by Donis, "Performance characteristics of qualified cell lines for isolation and propagation of influenza viruses for vaccine manufacturing", Vaccine, Volume 32, Issue 48, 12 Nov. 2014, Pages 6583-6590, relevant portions incorporated herein by reference.

As used herein, the term "virus-like particle" (VLP) refers to a membrane-surrounded viral core structure having viral envelope proteins. In addition, additional molecules can be expressed in or on the VLP, e.g., adjuvants, antigens, or reporter proteins or enzymes. Typically, viral core proteins are located within the membrane of the VLP and do not contain intact viral nucleic acids, and are non-infectious.

The present invention includes a vaccine against Zika virus as well as a high throughput assay to test anti Zika neutralizing antibodies and anti-viral compounds. The present invention provides for the first time a VLP-based vaccine, due to their protein composition only. Moreover, no VLP-based methodologies have been shown or published for Zika virus. VLP based approaches are both safer and more effective than DNA vaccines. The VLP system of the present invention overcomes the deficiencies in nucleic acid based approaches.

Development of Virus like Particle Vaccine and Reporter Assay for Zika Virus. Recent worldwide outbreaks of Zika virus (ZIKV) infection and the lack of an approved vaccine raise serious concerns regarding preparedness to combat this emerging virus. The present inventors used a Virus Like Particle (VLP) based approach to develop a vaccine and a microneutralization assay against ZIKV. Synthetic C-prM-E gene construct of ZIKV was used to generate Reporter Virus Particles (RVP) that package GFP reporter expressing WNV replicon. The assay was adapted to 96-well format, similar to the Plaque Reduction Neutralization assay (PRNT) and showed high reproducibility with specific detection of ZIKV neutralizing antibodies. Furthermore, C-prM-E and prM-E VLPs were tested as vaccine candidates in mice and compared to DNA vaccination. While flaviviral prM-E constructs alone are sufficient for generating VLPs; it was found that efficient VLP production with the C-prM-E constructs could be achieved in the presence of WNV NS2B-3 protease that cleaves C from prM allowing for VLP release. Immunization studies in mice showed that VLPs generated higher neutralizing antibody titers than DNA vaccine with C-prM-E VLPs slightly better than prM-E VLPs. The superiority of C-prM-E VLPs demonstrates that inclusion of Capsid may have benefits for ZIKV and other flaviviral VLP vaccines. To facilitate the VLP platform, the present inventors generated stable cell line expressing high levels of ZIKV prM-E proteins that constitutively produce VLPs as well as a cell line expressing ZIKV C-prM-E proteins for RVP production. Thus, the present invention provides a scalable platform to tackle the emerging threat of ZIKV by developing a safe, effective and economical ZIKV vaccine.

The present invention addresses two areas highly relevant to Zika virus research-development of an economical, efficacious and safe VLP-based vaccine and a rapid versatile diagnostic assay. The cell lines stably expressing the Zika prM-E were generated to produce high amounts of VLPs in the supernatants and a Zika C-prM-E expressing cell line was developed that produces reporter virus particle upon transfection with GFP replicon plasmid. It was found that the prM-E VLPs induced a strong neutralizing antibody response in mice that was better when the capsid protein was included in the VLPs. The VLP-based vaccines of the present invention showed significantly better neutralizing antibody response when compared to their DNA counterparts. Finally, a RVP-based microneutralization assay was developed that works similar to the plaque reduction neutralization test (PRNT) assay with a rapid GFP readout in a 96 well format. Thus, the VLP based platform provides a source for Zika vaccine, detection, and diagnosis that can be rapidly adapted to current outbreaks.

The present inventors determined the immune response in mice vaccinated with ZIKV VLP generated using a prM-E or the C-prM-E construct and compared it to the DNA based counterparts. To generate PrM-E VLPs, the inventors developed a cell line stably expressing the prM-E proteins while for C-prM-E, VLPs were generated by cotransfection of cells with C-prM-E and NS2B-3 protease of WNV to allow cleavage of Capsid (C) from prM-E. VLPs were purified via ultracentrifugation and used to immunize mice. Concomitantly, the inventors also developed a rapid and quantitative GFP based micro-neutralization assay using Reporter Virus Particles (RVPs) for measuring the neutralizing immune response generated in mice. These data demonstrates that both prM-E and C-prM-E based VLP vaccines were highly effective in generating neutralizing antibodies with the latter being more potent. Interestingly, while the prM-E DNA based vaccine was less effective than both the VLPs, the C-prM-E DNA construct was unable to generate significant neutralizing antibodies, most likely due to the lack of VLP formation in the absence of NS2B-3 protease. The RVP based neutralization assay of the present invention is safe for regular clinical laboratories because it does not require use of live virus and yielded results in <72 hrs compared to the PRNT assay that may require a week for completion. The assay was highly reproducible and effective in measuring the neutralizing antibody response against ZIKV that could be conducted in 96-well format using simple fluorescent microscopy. Thus, this study demonstrates for the first time the use of a VLP platform to tackle the emerging threat of ZIKV by providing a scalable source for a VLP based vaccine and RVP based diagnostic assay.

Cell culture and reagents. 293T and Vero cells were obtained from ATCC and cultured in DMEM supplemented with 10% FBS. All transfections were performed using Turbofect reagent (Thermo Fisher) as per the manufacturer's instructions. The WNV C-prM-E and Rep/GFP plasmids have been described previously (39) and were kindly provided by Dr. Ted Pierson (NIAID). Plasmid containing the WNV NS2B-3 accessory fusion protein expressing the active protease has been described previously (52) and was a kind gift from Dr. Frank Scholle (NC State Univ). The ZIKV-117 antibody was kindly provided by Dr. James Crowe (Vanderbilt University Medical Center, Nashville Tenn.) and ZIKV mouse polyclonal sera against the isolate MR766 was kindly provided by the Centers for Disease Control and Prevention (Fort Collins, Colo.). The ZIKV isolate PRVABC59 derived from a human serum specimen from Puerto Rico in December 2015 was obtained from ATCC and propagated in Vero cells strictly following the ATCC recommendations.

Generation of vectors expressing ZIKV C-prM-E and prM-E: ZIKV C-prM-E construct was synthesized using the complete ZIKV sequence available from the current outbreak in Americas (accession number KU312312.1). This most current sequence was used to synthesize a codon optimized version of the C-prM-E gene using the Gene Synthesis Technology by GenScript, Piscataway, N.J., USA. The synthesized gene was subcloned into pcDNA3.1™ vector (Invitrogen) using BamH1 and XhoI restriction sites. The C-prM-E cassette was also cloned into the lentiviral vector pLenti6/V5® vector (Invitrogen) using the above restriction sites to generate plasmid pLenti-C-prM-E. The prM-E construct was generated by PCR amplification of prM-E region spanning amino acids 105-795 using the Phusion® high fidelity PCR kit (New England BioLabs) and cloned into the pcDNA3.1+™ vector. The prM-E cassette was also subcloned into pLenti6/V5 vector using the BamH1-XhoI sites to generate plasmid pLenti-prM-E. Plasmids were sequenced to confirm sequence identity.

Detection of ZIKV E protein expression. Detection of ZIKV virus E protein was conducted either via immunofluorescence or Western blotting. For this, cells were stained using ZIKV E specific antibody MAB10216 (clone 4G2, EMD Millipore) that reacts with Flavivirus group specific antigens followed by secondary antibody Alexa 488 (Invitrogen) and analyzed by fluorescence microscopy. The monoclonal antibody MAB8150 (clone 3.67G, EMD Millipore) was used as control and reacts with E protein of West Nile/Kunjin virus. For Western blotting, lysates were resolved on an SDS-PAGE gel, transferred onto PVDF membranes and probed with ZIKV virus E antibody (GTX133314, GeneTex, 1:3000) followed by HRP conjugated anti mouse secondary antibody and bands visualized via enhanced chemiluminescence using the Super signal West Femto substrate (Pierce).

Metabolic labeling and immunoprecipitation. The protocol for radiolabeling and immunoprecipitation of cell and virus lysates has been described in detail previously (Garg, 2013. Briefly, transfected cells were washed with RPMI medium lacking Met and Cys. Thereafter, cells were incubated in RPMI medium supplemented with FBS and [35S] Met/Cys. Culture supernatants were filtered and subjected to ultracentrifugation at 100,000×g for 45 min. Cell and virion samples were lysed with Triton X containing lysis buffer (0.5% Triton X-100, 300 mM NaCl, 50 mM Tris [pH 7.5] containing protease inhibitors [Complete; Roche]). Thereafter, lysates were immunoprecipitated with anti-WNV serum (kindly provided by Dr. Robert B. Tesh, University of Texas Medical Branch, Galveston) or MAB10216 coated Protein A beads. Immunoprecipitated cell lysates were washed three times with TritonX-100 wash buffer and once with SDS-DOC wash buffer (0.1% sodium dodecyl sulfate, 300 mM NaCl, 50 mM Tris [pH 7.5], 2.5 mM deoxycholic acid), resolved by SDS-PAGE followed by PhosphorImager analysis.

Production of RVPs. ZIKV RVPs were generated using protocol described previously (38) with some modifications and originally described by Pierson et al (39). 293T cells were co-transfected with the ZIKV C-prM-E construct along with plasmid containing the sub-genomic GFP expressing replicon derived from lineage II strain of WNV (39). The RVPs were harvested 48 h post transfection, aliquoted and stored for future use. RVPs were titrated in Vero cells plated in 96 well clear bottom black plates at 5,000 cells per well. Thereafter, cells were infected with serial two-fold dilutions of the RVPs and incubated for 72 h. The plates were fixed using 4% formalin/PBS, images acquired using a Nikon EclipseTi microscope and number of GFP positive cells counted using the NIS elements software (Nikon).

RVP based and clinical ZIKV based microneutralization assay. For neutralization assays, mouse sera or antibodies were serially diluted in DMEM in technical duplicates in a volume of 50 µl. Thereafter, a predetermined concentration of virus producing 200 to 500 GFP positive cells was added to each well in a volume of 50 µl. The sera and RVPs were incubated for 1 h at room temperature. Subsequently, the virus:sera mix (100 µl) was added to Vero cells after removing all the media and incubated for ~72 h after which the number of GFP positive cells was quantitated. Statistical analysis was performed using the unpaired t test. The limit of detection for the RVP assay was defined as the highest concentration of sera (1:20 dilution) used in the neutralization experiments.

For neutralization assays using the ZIKV isolate PRV-ABC59, mouse sera was serially diluted in serum free media in technical duplicates in a volume of 50 µl. Thereafter, diluted ZIKV was added to each sera sample at an MOI of ~5 and incubated for 2 h at 37° C. The virus antibody mixtures were then added to Vero cells plated in 96-well plates and incubated for another 2 h at 37° C. The virus antibody mix was then removed and cells incubated in DMEM containing 10% FBS for 48 h. The cells were then fixed and stained using MAB10216. Images were acquired using fluorescence microscopy and number of antibody stained cells quantitated as described above.

Generation of stable cell lines expressing ZIKV C-prM-E or prM-E: Lentiviral vectors expressing ZIKV C-prM-E and prM-E were packaged in 293T cells by transfecting with pLenti-C-prM-E or pLenti-prM-E along with the helper construct php-dl-NA (NIH AIDS Reagent program) and VSVG Env. The viral supernatants were collected at 48 h post transfection, aliquoted and stored. To generate stable cell lines, 293T cells were transduced with the lentiviral particles and the cells were selected using blasticidin at a concentration of 10 µg/ml. Bulk selected cells were passaged 8-10 times and stained for ZIKV E protein expression using monoclonal Ab MAB10216 at regular intervals to confirm selection. Subsequently, single cell clones were generated from the bulk selected cells using limiting dilution cloning in 96 well plates. Up to 6 single cell clones were selected for both C-prM-E and prM-E constructs from wells that showed single colony formation. Each single cell clone was further characterized for ZIKV E protein expression using immunostaining followed by flow cytometry.

Production of DNA and VLPs for immunization: For DNA immunizations in mice, the pcDNA-C-prM-E and pcDNA-prM-E plasmids were purified using the endotoxin free plasmid maxi kit (Qiagen) following the manufacturer's protocol. VLPs for immunization were generated and purified. For C-prM-E VLPs, 293T cells were transfected with pcDNA3.1-CprM-E construct along with WNV NS2B-3 plasmid. The viral supernatants were harvested at 24 h and 48 h post transfection. For production of prM-E virus particles, the 293T-Lenti-prM-E bulk cell line was cultured in the absence of Blasticidin and supernatants harvested at 72 and 96 hrs. VLPs were concentrated as follows. Harvested supernatants (25-30 ml) were transferred into ultracentrifuge tubes and carefully underlayed with 5 ml of 25% glycerol in TNE buffer. VLPs were pelleted by centrifugation at 110,500×g for 3 hrs at 4° C. Thereafter, the supernatant was carefully removed and the VLP pellet resuspended in PBS or TNE buffer. The total protein content in the VLP prep was measured using the micro BCA kit (Pierce) and specific E protein in the prep was detected by western blotting using the GTX133314 antibody.

Electron microscopy. VLPs were concentrated as above and imaged by electron microscopy after negative staining. Purified VLPs (3 µl) were applied to glow-discharged carbon-coated 300 mesh grid. After ~1 min, the grid was blotted with filter paper and 3 µl of 2% uranyl acetate aqueous solution was added for 30 sec. After blotting off excess liquid and drying, images were acquired using the Transmission Electron Microscope JEOL1010 with a Hamamatsu digital camera and AMT Advantage image capture software at 100× magnification.

Mice studies. For immunization studies, 6 to 8 week old Balb/c mice were purchased from Jackson laboratory and housed in pathogen free animal facility at Texas Tech University Health Sciences Center, El Paso. Mice were divided into groups of six mice each and immunized with different preparations. For DNA immunization, a total of 50 µg of DNA in a volume of 100 µl PBS was injected intramuscularly in each thigh. Mice received two additional boosts at week 2 and 4 of primary immunization as described above. For VLPs, the first immunization consisted of VLP prep (approximate total protein content 1.7-2.3 mg/ml) mixed with TiterMax Gold adjuvant (Sigma) at a 1:1 ratio in total volume of 100 µl injected intramuscularly in each thigh. Mice received two additional boosts of VLPs at week 2 and 4 without adjuvant. Control mice were sham injected with PBS. Blood was collected from mice at week 9 post first immunization under terminal isoflurane anesthesia followed by intracardiac puncture. Blood samples were collected in serum separator tubes as per the manufacturer's recommendations. After coagulation, the tubes were centrifuged, sera harvested, aliquoted and stored at −80° C. until further use.

Expression of ZIKV C-prM-E using codon optimized synthetic construct: To develop a VLP based platform for ZIKV vaccine and RVP assay, the inventors used the complete ZIKV sequence available from the current outbreak in Americas (KU312312.1) (6) to synthesize a codon optimized C-prM-E gene. The isolate was derived from a 52 year male hospitalized with symptoms of conjunctivitis and exanthema in Paramaribo (Suriname) in 2015. The synthesized gene was cloned into pcDNA3.1™ vector that contains a CMV promoter (FIG. 1A). 293T cells transfected with the synthetic ZIKV C-prM-E or WNV C-prM-E construct were tested for E protein expression by immunofluorescence using antibodies MAB10216 (clone 4G2) and MAB8150 (clone 3.67G). As shown in FIG. 1B, the MAB10216 reacted with both ZIKV and WNV E protein while the MAB8150 only reacted specifically with the WNV E protein. This is expected as the MAB10216 reacts with flavivirus group specific antigens (36) and binds to the fusion loop at the extremity of domain II of the E protein while the MAB8150 is specific for the E protein of West Nile/Kunjin virus. The inventors also performed radioimmunoprecipitation analysis of ZIKV C-prM-E expression after transfection in 293T cells and compared it to WNV. As shown in FIG. 1C, both ZIKV and WNV C-prM-E were immunoprecipitated with MAB10216 and also with anti-WNV mouse sera, although with different efficiencies, emphasizing the relatedness between flaviviruses (37). These data demonstrate that the ZIKV C-prM-E synthetic construct expresses the viral proteins at high levels and can be used in downstream assays requiring VLP production.

Figure 2B:
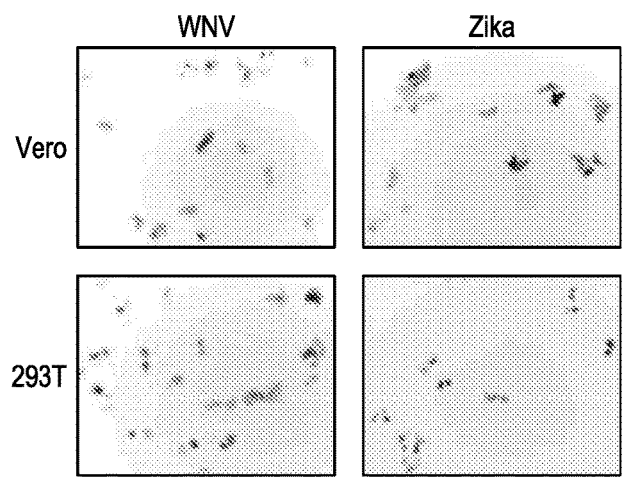

RVP based microneutralization assay for ZIKV using a 96 well format and GFP readout. To make and test ZIKV RVPs, the inventors used the method described previously by Garg et al (38) and adapted from Pierson et al (39). 293T cells were co-transfected with the ZIKV C-prM-E construct along with the WNV replicon reporter plasmid Rep/GFP (29, 39, 40) that provides the WNV accessory proteins and the GFP reporter gene (FIG. 2A). RVPs generated in a similar manner using WNV C-prM-E alongside were used as positive control. Both WNV and ZIKV RVPs showed robust infection of Vero and 293T cells (FIG. 2B).

Figure 2C:
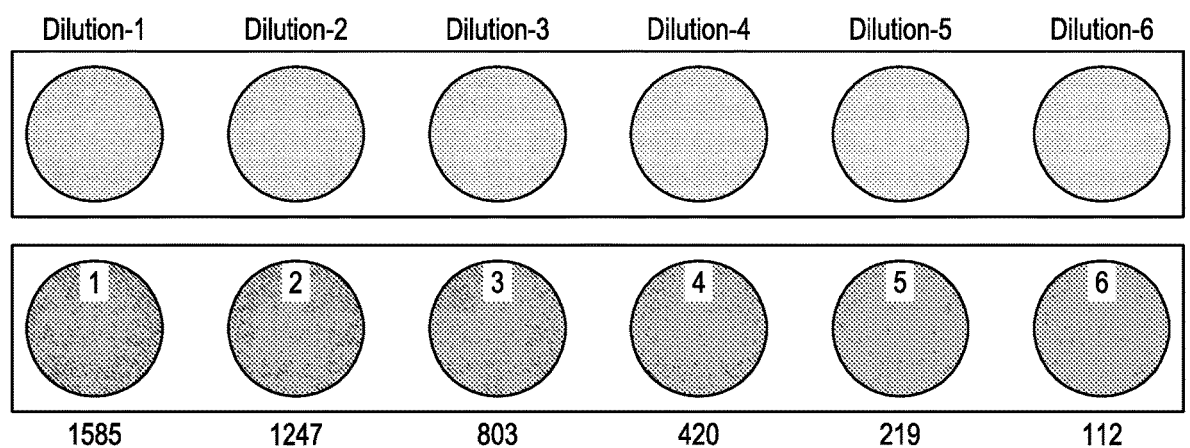
Figure 2F:
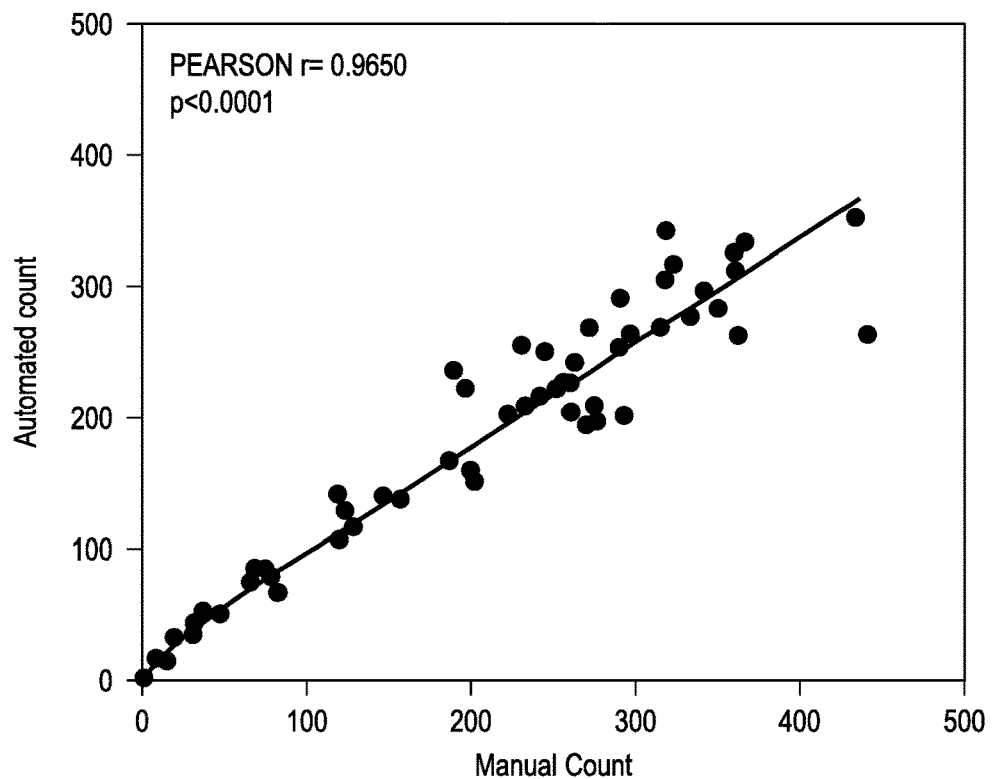

Although ZIKV RVPs have recently been used by other labs, the current method of choice is infection of Raji or Vero cells, followed by detection of GFP+ cells via flow cytometry (29, 39, 40). On the other hand, the infectious virus based PRNT utilizes Vero cells in 96 well format and can be tedious and time consuming. The inventors adapted The RVP based assay to a 96 well plate using Vero cells similar to the PRNT method. Cells plated in 96 well clear bottom black tissue culture plates were infected with serial dilutions of the RVPs. The plates were fixed 72 h later, analyzed by fluorescent microscopy and the number of GFP positive cells counted using an automated software (NIS Elements, Nikon). Serial dilutions (1-6) of the input virus showed a dose dependent decrease in the number of GFP positive cells (FIG. 2C). The assay was conducted using ZIKV (FIG. 2D) and WNV (FIG. 2E) RVPs and GFP+ cells were quantified using the automated software. The assay showed high level of reproducibility with minimum variation between replicate wells. The linear range of the assay was between 200-800 GFP+ cells. The inventors also compared manual cell counting versus automated software (NIS Elements) and found a high degree of correlation between the two methods ($r=0.9650$, $p<0.0001$) (FIG. 2F) suggesting that manual GFP+ counting using a simple fluorescent microscope could also be used for the assay. Hence, this assay, much like the PRNT, can be adapted to give a reasonable number of GFP+ cells that can be counted either manually or using automated software.

Figure 2G:
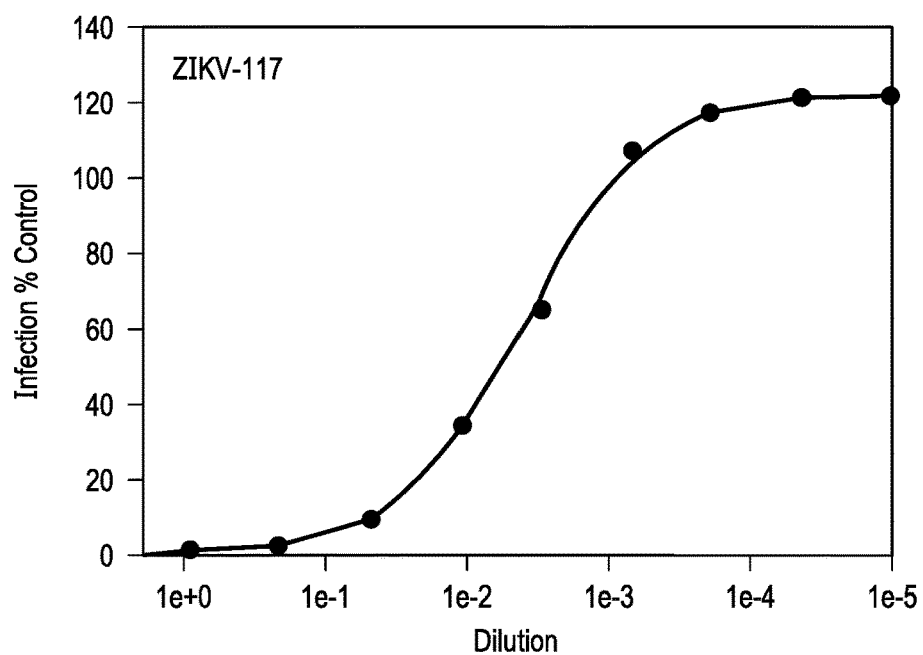
Figure 2H:
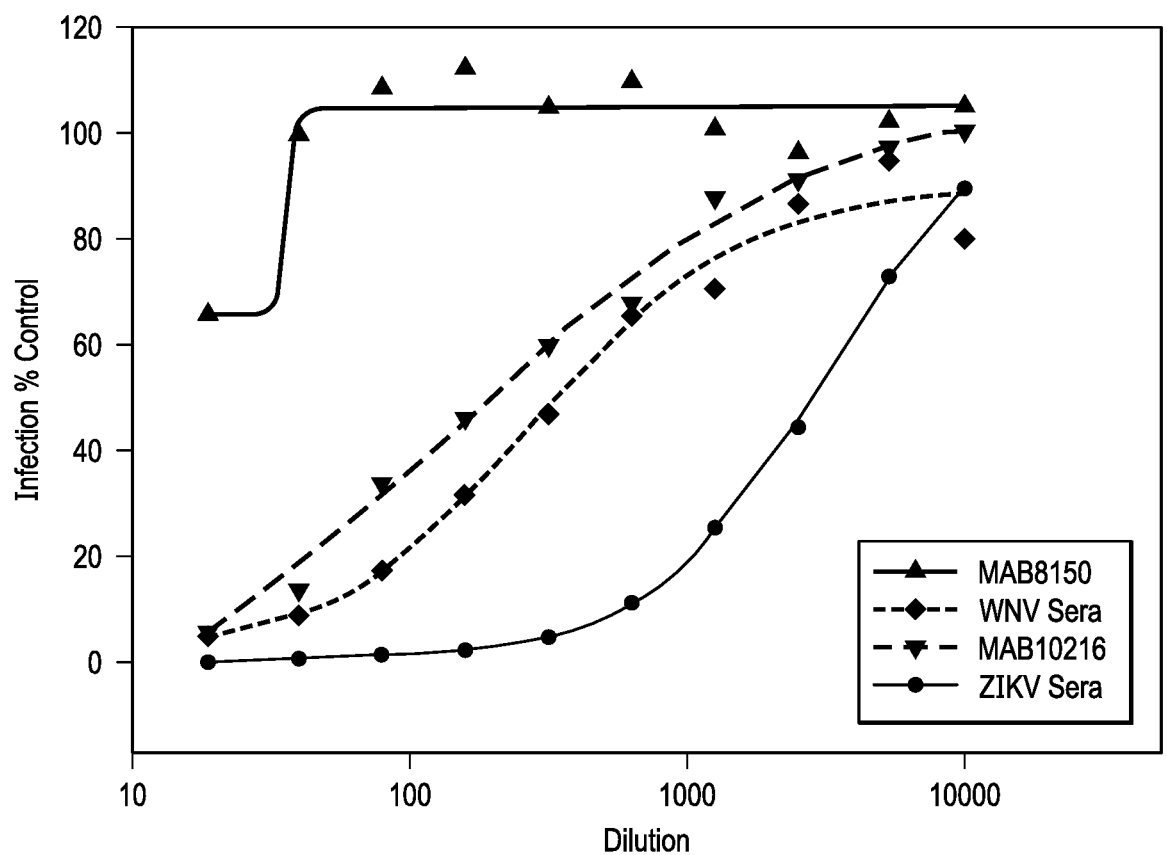

The inventors next tested whether the assay could detect neutralization of ZIKV RVPs via antibodies or polyclonal mouse sera. Experiments were carried in a manner similar to the standard PRNT, where sera/antibody dilutions were incubated with RVPs for 1 h prior to addition to Vero cells. As shown in FIG. 2G, a human antibody against the ZIKV E protein (ZIKV-117) known to prevent infection via cross linking the protein (41) potently inhibited RVP infection in a dose dependent manner. Moreover, WNV pooled sera, polyclonal ZIKV sera and MAB10216 also inhibited ZIKV RVP infection in a dose dependent manner (FIG. 2H). Interestingly, and as expected, the antibody MAB8150 that failed to bind ZIKV E protein in immunofluorescence did not inhibit RVP infection (FIG. 2H). This demonstrates that the assay is specific and can be readily used to test for the presence of ZIKV neutralizing antibodies. Similar to PRNT, this assay can also be used to calculate EC50 and EC90 for serum samples. For example, the EC90 for WNV serum to inhibit 90% ZIKV infection was determined to be 80 and the EC50 to inhibit 50% ZIKV infection was 640 (FIG. 2H). The above data demonstrate that WNV replicon reporter construct along with ZIKV C-prM-E can yield infectious RVPs that can subsequently be used for several applications including a microneutralization assay while obviating the use of infectious virus and high level biosafety containment.

Figure 3A:
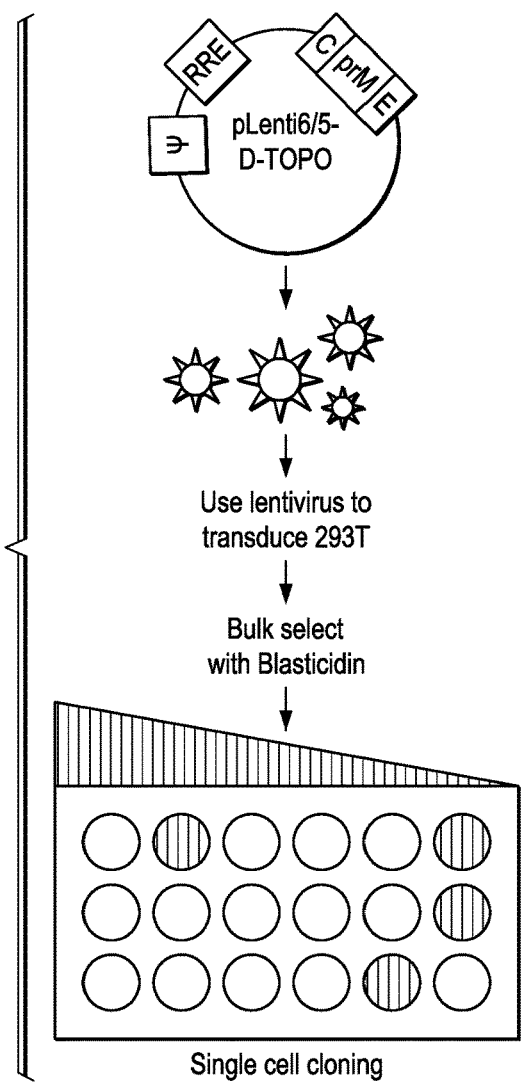
FIGS. 3A to 3G shows the establishment of a stable cell line expressing ZIKV C-prM-E.
Figure 3B:
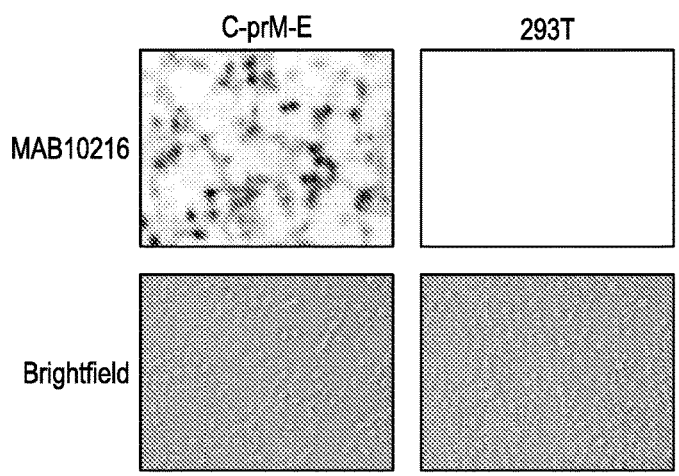
Figure 3C:
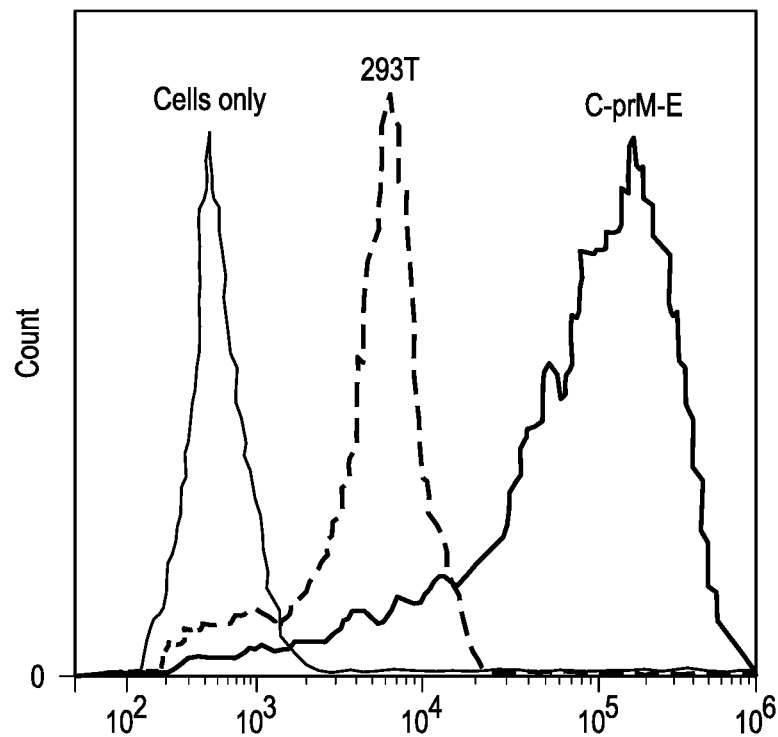
Figure 3D:
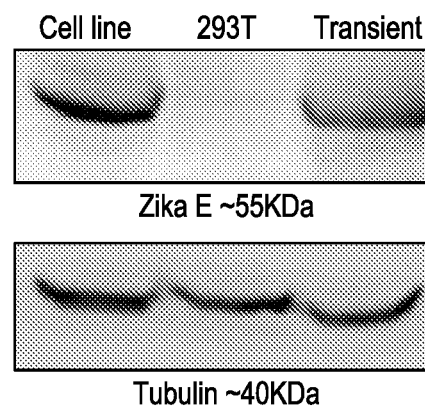
Figure 3E:
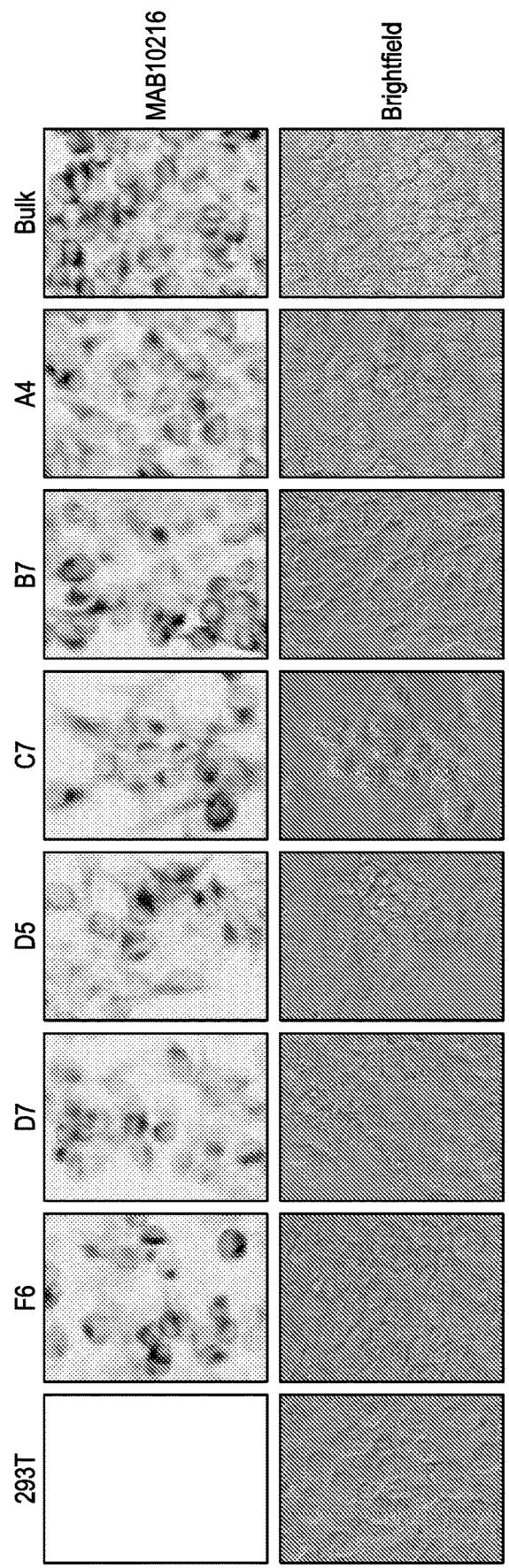
Figure 3F:
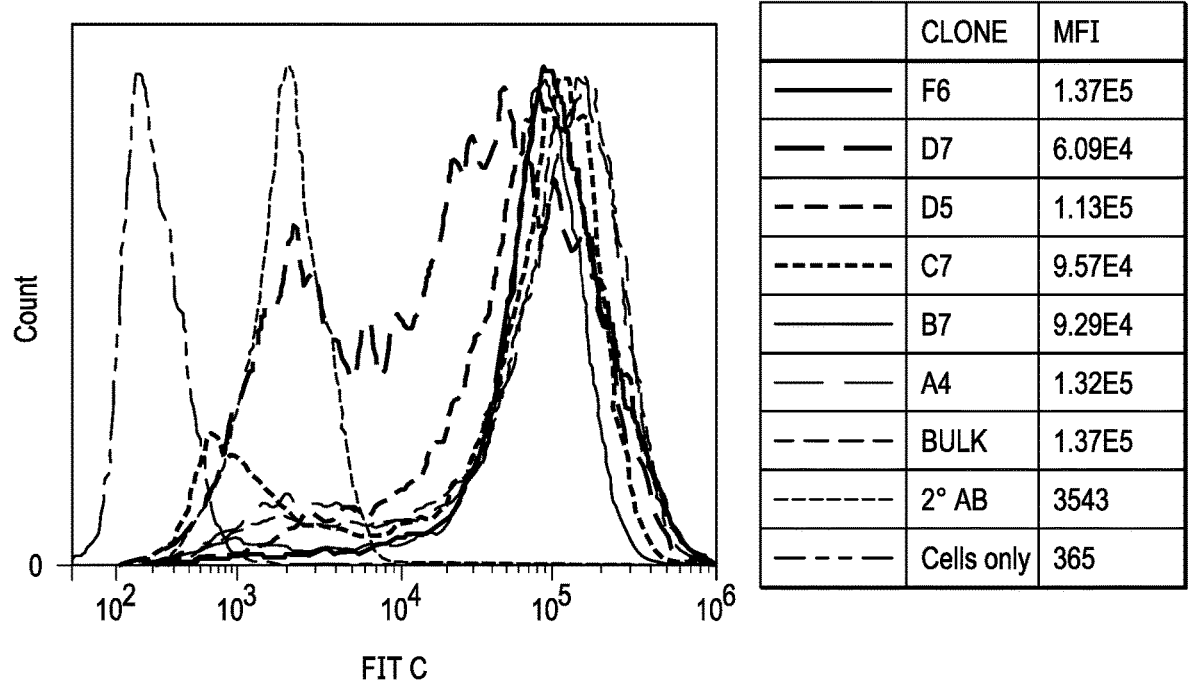
Figure 3G:
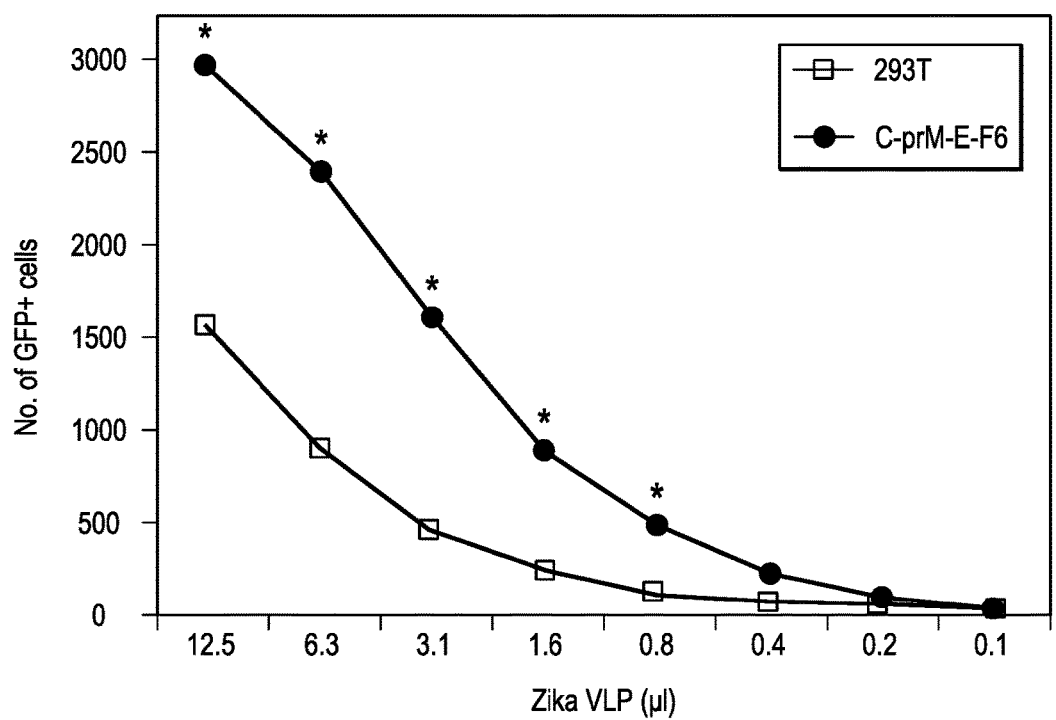

Establishment of a stable cell line expressing ZIKV C-prM-E. The sudden outbreaks of ZIKV infection have caught the research community off guard and the limited number of reagents and resources available for ZIKV studies has hampered research efforts. The inventors hence developed a stable cell line expressing the ZIKV C-prM-E to facilitate generation of RVPs. For this, the codon optimized ZIKV C-prM-E cassette was subcloned into a lentiviral vector (pLenti6/V5®) carrying a Blasticidin resistance gene (FIG. 3A). Lentiviral particles generated with this vector were used to transduce 293T cells which were selected in the presence of 10 µg/ml Blasticidin for 2 weeks. Bulk selected cells were tested for expression of ZIKV E protein via fluorescence microscopy (FIG. 3B) and flow cytometry (FIG. 3C) and showed robust expression with more than 90% cells positive for the E antigen. The inventors also confirmed the expression of ZIKV E protein using Western blotting in the selected cell line and compared it to transient protein expression after transfection. As expected, high levels of E protein expression was seen in the 293T-C-prM-E-bulk cell line (FIG. 3D). As lentivirus transduced cells can have different levels of exogenous gene expression (42, 43), the inventors also selected single cell clones from the parent bulk cell line. A total of 6 single clones were selected via limiting dilution cloning and characterized for ZIKV E expression using fluorescent microscopy (FIG. 3E) as well as flow cytometry (FIG. 3F). Based on The flow data, clone F6 (293T-C-prM-E-F6) showed the highest expression and was chosen for subsequent experiments. The inventors generated RVPs using the 293T-C-prM-E-F6 cell line after transfecting with WNV Rep/GFP replicon plasmid and compared it to RVPs generated in 293T cells after transient transfection with pcDNA-C-prM-E and Rep/GFP. RVPs generated using the 293T-C-prM-E-F6 cell line were of significantly higher titers when compared to virus produced form 293T cells (FIG. 3G). Thus, the 293T-C-prM-E-F6 cell line stably expresses the ZIKV structural proteins and can be used for generation of high titer RVPs.

Figure 4H:
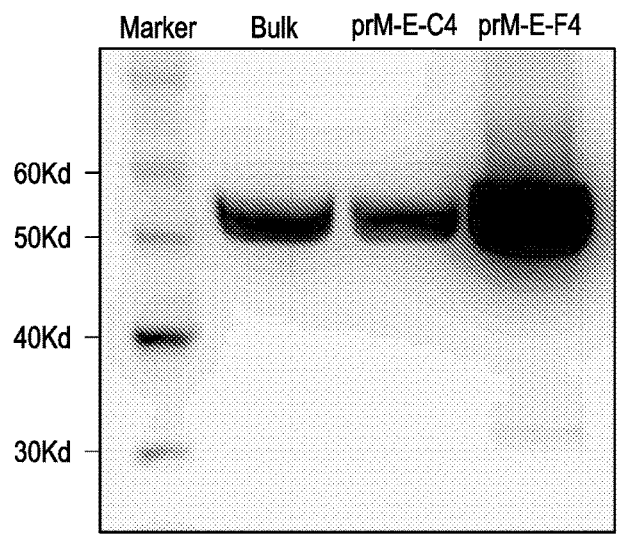

Generation of prM-E cell line for VLP production. Extensive studies with different flaviviruses including ZIKV have shown that expression of prM-E in the absence of capsid can produce sub viral particles that can be used for immunization and elicit protective antibodies (44-48). These prM-E based constructs are also the basis of DNA and mRNA nanoparticle vaccines currently in development for ZIKV (20-25). The inventors hence developed a stable cell line that would constitutively produce prM-E VLPs in the supernatant and can be used for large-scale production of VLPs for immunization studies. For this, the inventors used the original C-prM-E construct and PCR amplified and cloned the prM-E region spanning amino acids 105-795 (FIG. 4A) into the pcDNA3.1™ vector (FIG. 4B). The last 17 amino acids of capsid after the NS2B-3 cleavage site were included in the prM-E construct for proper translocation into the ER lumen. Once the expression of E protein (FIG. 4C) and VLP production in the supernatant (FIG. 4D) was confirmed, the prM-E region was subcloned into the lentivirus vector generating pLenti-prM-E (FIG. 4E). Packaged lentiviral particles were used to transduce 293T cells and generate bulk selected cell line and single clones (FIG. 4E). As above for the C-prM-E cell lines, 6 single cell clones were selected and characterized for ZIKV E protein expression (data not shown). The clones C4 and F4 showed highest expression both by immunofluorescence (FIG. 4F) and flow cytometry (FIG. 4G). Finally, the inventors characterized the single cell clones for production of VLPs in the supernatants. For this, supernatants from the 293T-prM-E cell lines were ultracentrifuged through a glycerol cushion (49), virus pellet was lysed and E protein detected by western blotting (FIG. 4H). Interestingly, the cell line 293T-prM-E-F4 showed significantly higher VLP production than the 293 T-prM-E-Bulk and the 293 T-prM-E-C4 cell line. Thus, the inventors have generated cell lines that constitutively produce high levels of ZIKV prM-E VLPs in the supernatant that can be used for VLP based vaccine studies. Production of VLPs from The stable cell lines can be readily scaled up for clinical trials.

Figure 5A:
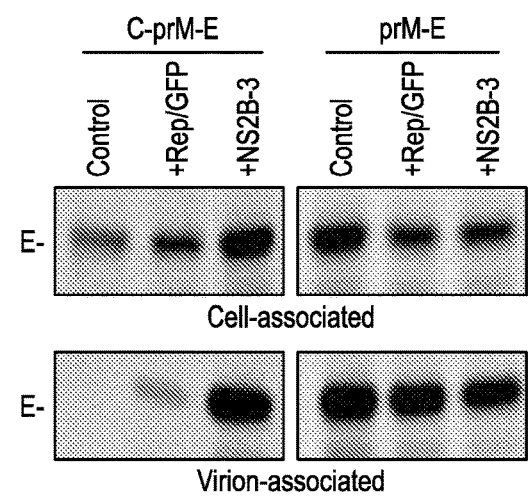
FIGS. 5A to 5E shows the expression of ZIKV prM-E alone releases VLPs in the supernatants while the C-prM-E requires the protease NS2B-3 for efficient VLP release.
Figure 5B:
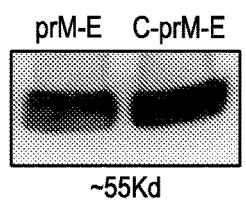
Figure 5C:
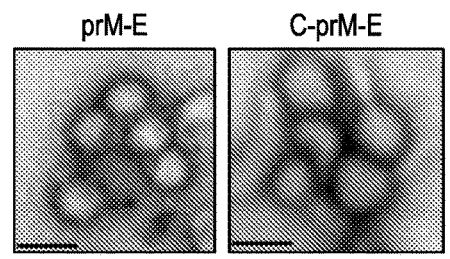

Immunization studies in mice: Lack of an approved vaccine for ZIKV amidst the recent outbreaks and the association of ZIKV infections with severe congenital birth defects, warrants development of a safe and efficacious vaccine against the virus. For a vaccine to be available worldwide, especially in underdeveloped countries, it should be both easy to prepare and cost effective. In this regard, stable cell lines constitutively producing the ZIKV VLPs would be optimal as they can be readily scaled up with minimal scientific infrastructure and can provide an economical alternative to other forms of vaccination. The inventors hence tested the immunogenicity of the ZIKV VLPs in mice. Although prM-E VLPs are most commonly used in flavivirus vaccine research, the inventors also generated VLPs incorporating the capsid protein using the C-prM-E construct. While prM-E particles can be readily be generated using The stable cell lines (293T-prM-E), for generation of C-prM-E VLPs the WNV NS2B-3 protease was needed for cleavage of C from prM-E in the ER (35, 50). As shown in FIG. 5A and consistent with published findings (50, 51), expression of the WNV protease NS2B-3 was essential for release of C-prM-E but not prM-E VLPs. Hence, for generation of C-prM-E VLPs, cells were co-transfected with the NS2B-3 expression plasmid (52). Using these two different strategies, the inventors generated both prM-E and C-prM-E VLPs that were purified from culture supernatants by ultracentrifugation through a glycerol cushion (49). The purified VLP pellet was analyzed for E protein expression via western blotting and VLP morphology by electron microscopy. As shown in FIG. 5B, there were high amounts of E protein detected in both the prM-E and C-prM-E VLP preps. The total protein content of the VLP preps ranged from ~1.7-2.3 mg/ml. Electron microscopy showed that the VLP particle morphology was consistent with that of ZIKV with the approximate particle diameter ranging from 30-40 nm (FIG. 5C).

Figures 5D, 5E:
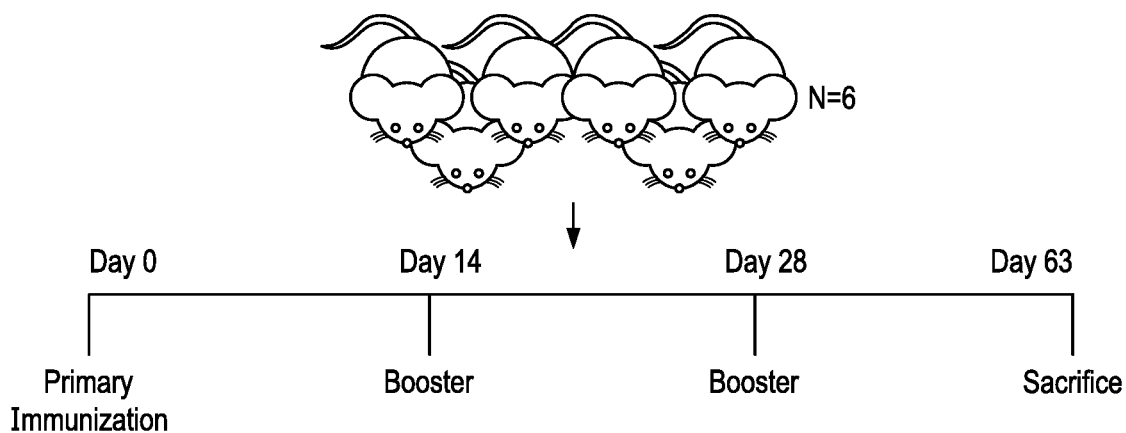

The purified VLPs were subsequently used to immunize mice. The immunization schedule is shown in FIG. 5D. Mice divided into 5 groups of 6 mice each were immunized with either prM-E or C-prM-E DNA or the corresponding VLPs (FIG. 5E). Mice in the control group were sham injected with PBS. For the first immunization, the VLPs were emulsified with a 1:1 mix of TiterMax Gold. All mice received 2 booster injections with the respective DNA or VLPs at day 14 and day 28 and the mice were sacrificed on day 63, blood collected by intra-cardiac puncture and sera was harvested.

Figure 6A:
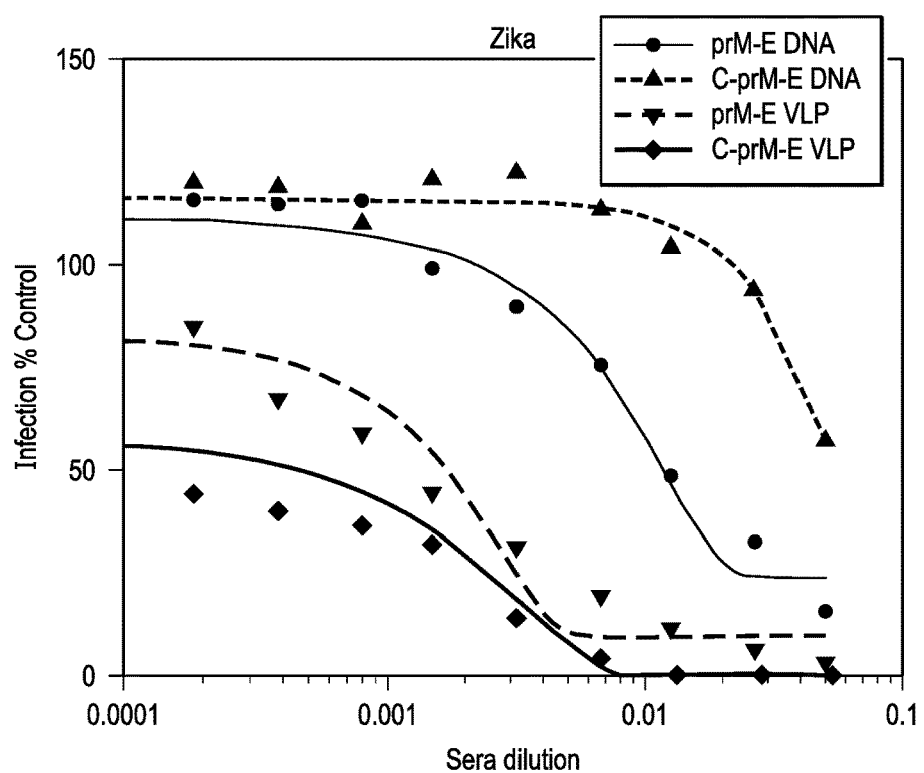
FIGS. 6A to 6F shows the Anti-ZIKV immune response in mice immunized with prM-E/C-prM-E DNA and VLPs.
Figure 6B:
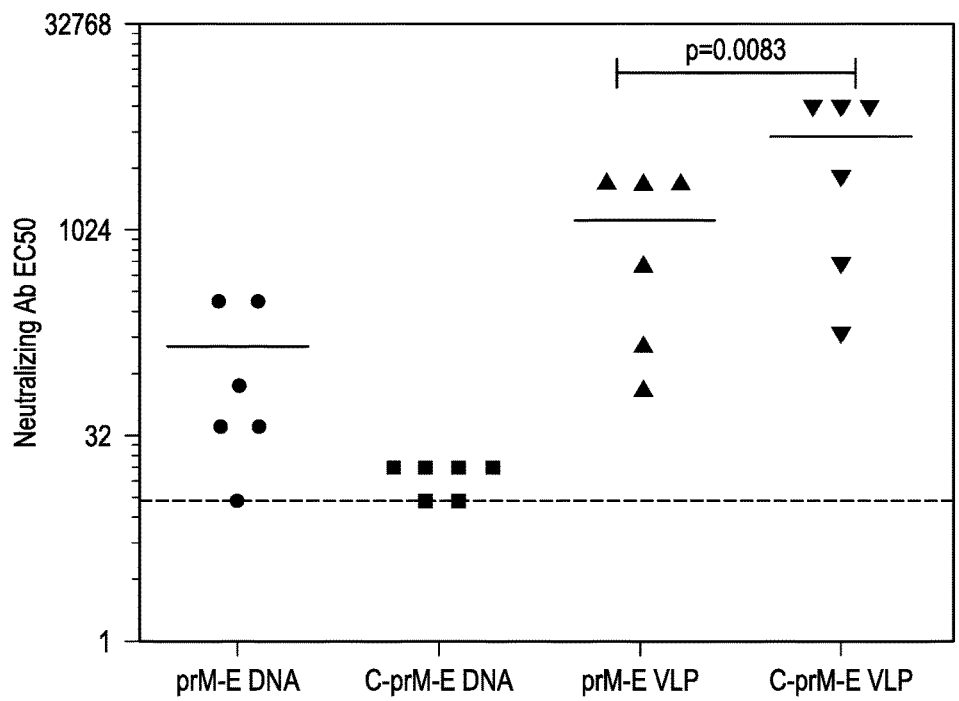
Figure 6C:
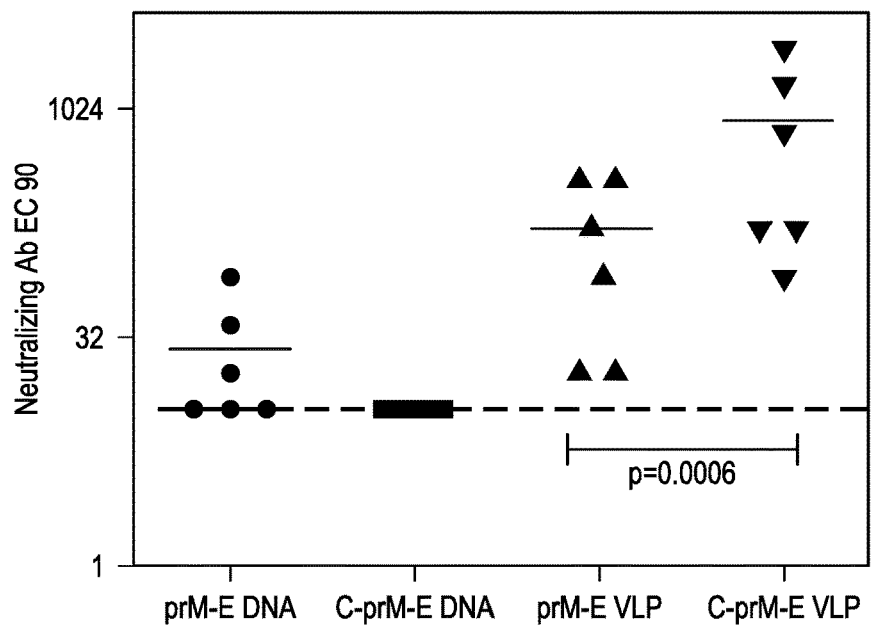
Figure 6D:
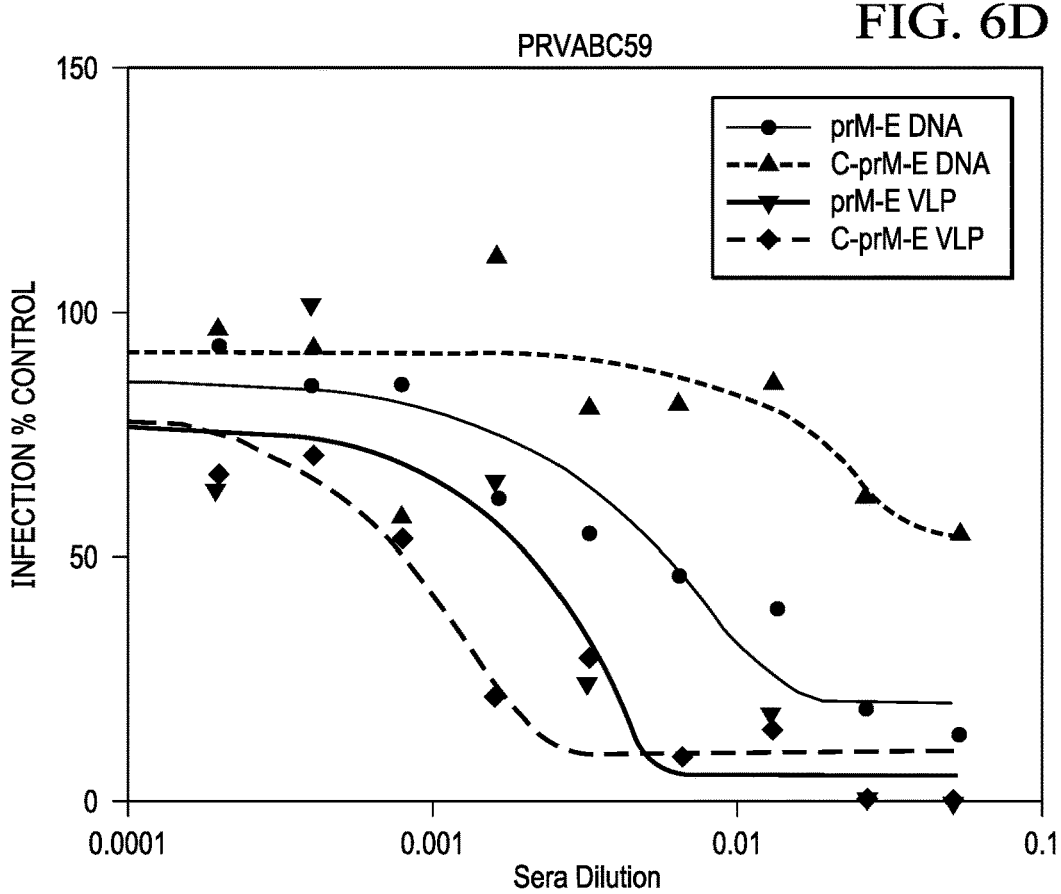
Figure 6E:
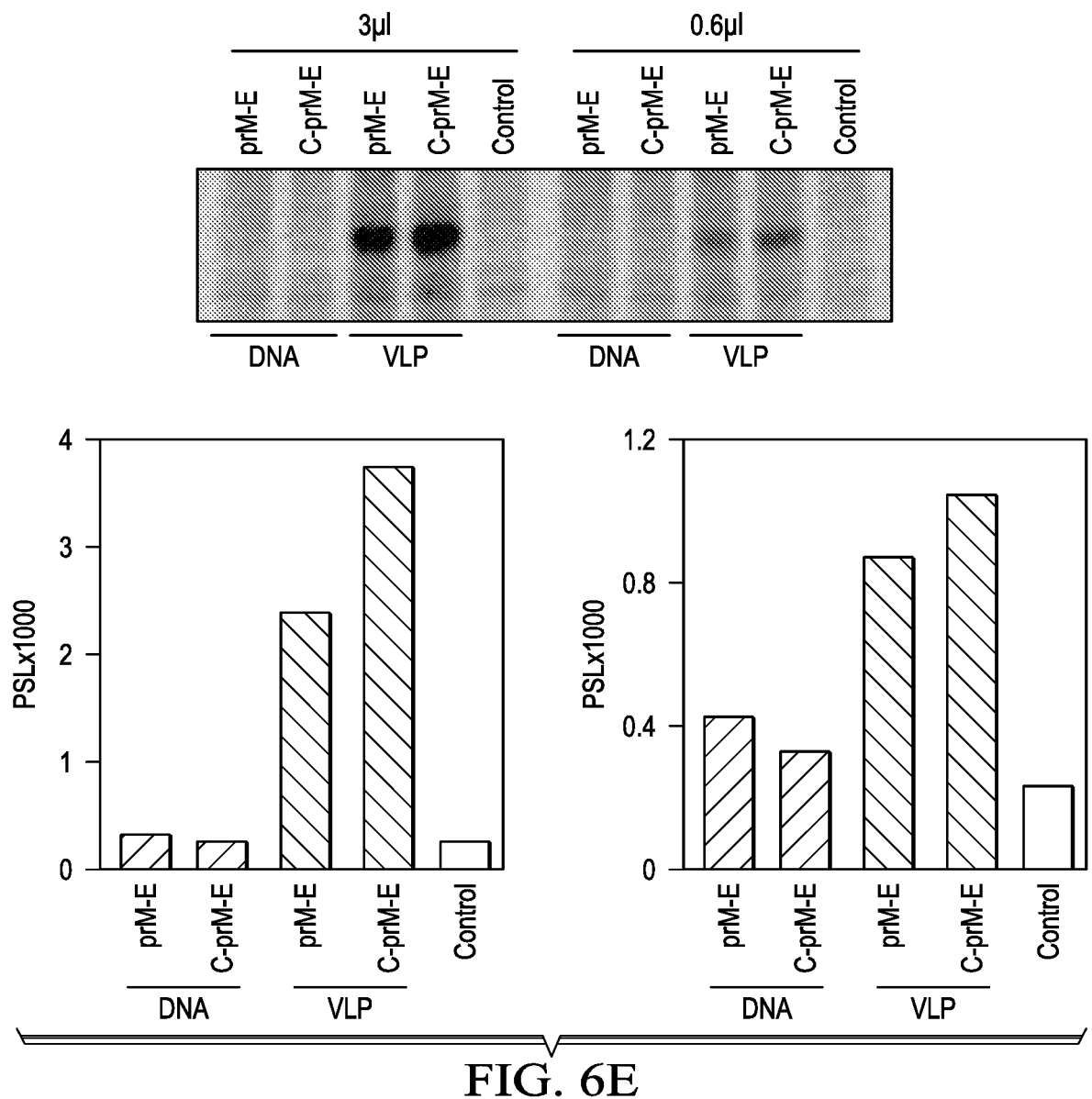

Anti-ZIKV virus immune response in mice immunized with prM-E/C-prM-E DNA and VLPs. The inventors next determined the immune response generated in mice upon immunization with the DNA or VLP based vaccines. Two-fold serial dilutions of the individual mice sera were tested in the RVP based microneutralization assay described in FIG. 2. Interestingly, the C-prM-E VLPs elicited the best neutralization titers followed by the prM-E VLPs and prM-E DNA vaccine (FIG. 6A). Interestingly, the C-prM-E DNA worked the poorest in generation of neutralizing antibodies most likely because C-prM-E DNA in the absence of NS2B-3 protease fails to assemble and release VLPs with the proteins being sequestered in the ER. The mean EC50 titers were>1:1000 for both the VLP vaccines and 1:132 for prM-E DNA while C-prM-E DNA showed<1:32 titers (FIG. 6B). The EC90 titers followed a similar trend (FIG. 6C). Moreover, there was a significant difference in EC50 ($p=0.0083$) and EC90 values ($p=0.0006$) between the prM-E and C-prM-E VLP immunized mice (FIGS. 6B and C). The inventors also tested the ability of the immune sera generated in mice to neutralize a clinical ZIKV isolate PRV-ABC59. As evident in FIG. 6D, the mice sera samples were able to neutralize the clinical ZIKV isolate following a trend similar to that seen with neutralization of ZIKV RVPs in FIG. 6A. To further confirm the presence of ZIKV E specific antibodies, the inventors conducted an immunoprecipitation assay using pooled sera from different groups of immunized mice. For this, C-prM-E expressing cells were radiolabeled with [$^{35}$S]Met/Cys protein labeling mix and cell lysates were immunoprecipitated with Protein A beads coated with either 3 μl or 0.6 μl of pooled sera from respective immunized groups. As shown in FIG. 6E and consistent with microneutralization data, pooled sera form the C-PrM-E VLP immunized group showed highest E protein band intensity followed by the prM-E VLP group. Sera from prM-E DNA group showed low levels of anti-E antibodies followed by the C-prM-E DNA, again consistent with neutralization data presented in FIG. 6A. These results confirm that high levels of neutralizing antibodies against ZIKV virus E protein were generated using either prM-E or C-prM-E VLPs and this approach can be used for generation of safe and effective vaccine.

Figure 6F:
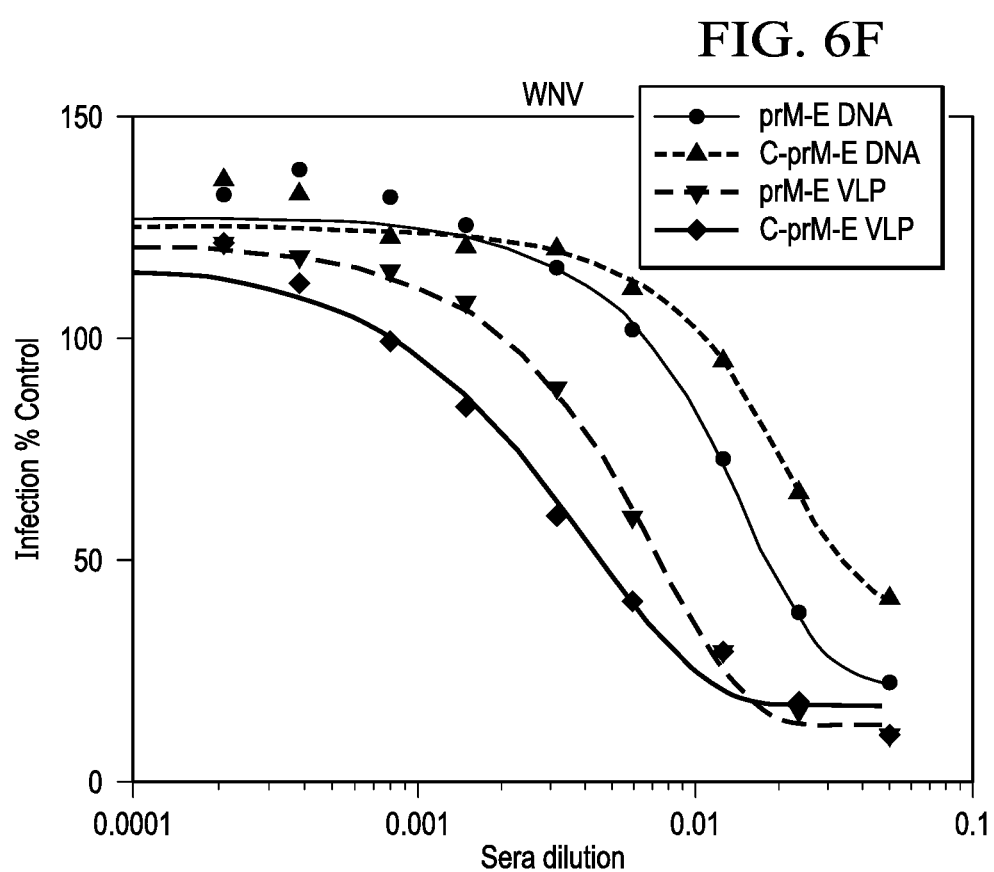

The inventors have previously seen that immune sera from WNV infected mice is capable of binding to ZIKV E protein and cross neutralize ZIKV RVPs (FIGS. 1 and 2). The inventors hence determined if pooled sera form The ZIKV immunized mice groups was able to cross neutralize WNV infection using the RVP assay. For this, the inventors prepared WNV reporter VLPs using WNV C-PrM-E and the Rep/GFP construct as described previously (38). Interestingly, sera obtained from ZIKV VLP/DNA immunized mice was able to cross neutralize WNV RVP infection in a trend that was similar to ZIKV RVP inhibition, although with a lower efficacy (FIG. 6F). Here again, sera from ZIKV C-prM-E VLP immunized mice was most effective followed by prM-E VLPs and PrM-E DNA with C-prM-E DNA being the least effective (FIG. 6F). These data demonstrate the efficacy of VLP based vaccine compared to DNA vaccination in generating a robust neutralizing antibody response against ZIKV. Furthermore, incorporation of the capsid in VLPs shows enhanced immune response against ZIKV although prM-E VLPs are sufficient for inducing high level of neutralizing antibodies. The initial outbreaks of ZIKV virus infection in Africa and Southeast Asia and subsequent transfer of infection to western countries including the US has raised concerns regarding lack of preparedness to combat the virus (5-7). Currently there is no approved vaccine or specific treatment for ZIKV infections. Moreover, there is limited information regarding ZIKV spread, its enhanced specificity for neural fetal tissue and the mechanism via which it causes microcephaly. Thus, there is an urgent need to not only understand the basic virus biology but also develop safe and efficacious vaccines to target the virus. Moreover, there is a need for development of rapid, reliable and accurate assays that can be used to test anti-ZIKV immune responses and antiviral agents.

The ZIKV genome consists of a single stranded positive sense RNA and an open reading frame encoding a polyprotein 5'-C-prM-E-NS1-NS2A-NS2B-NS3-NS4A-NS4B-NS5-3' (53, 54). This polyprotein is subsequently cleaved into Capsid (C), precursor of membrane (prM), Envelope (E) and seven non-structural proteins (53, 55). The E protein (~53 Kd) is the major virion surface protein involved in virus binding to the cell surface and membrane fusion (53, 55). Co-expression of the flaviviral proteins prM and E leads to secretion of VLPs that do not contain viral RNA and resemble empty particles produced during viral infection (48, 50, 56-58). These VLPs induce neutralizing antibody responses that are more potent than purified proteins (59, 60). One of the major obstacles in flavivirus research is the requirement of high level biosafety containment to undertake infectious virus studies with BSL-2 or higher needed for ZIKV studies. The persistence of ZIKV in body for prolonged periods (12) and the reports of sexual transmission (10, 11) highlight the risks associated with working with infectious virus. The use of VLPs has recently emerged as a powerful technology not only to study basic virus biology but also for vaccine and diagnostic assay development (59, 60). VLPs resemble viruses and are largely composed of viral structural proteins (53, 55). VLPs contain minimal or no genetic material, are non-replicating, and may also contain a reporter gene, thus allowing for easy detection (39, 61). Moreover, the requirement of high level biosafety containment to undertake infectious flavivirus studies (61, 62) can be overcome by using recombinant VLP based assays. This eliminates the use of infectious virus while still allowing testing of various aspects of the pathogen including: (1) mechanism of viral entry; (2) neutralizing antibody sensitivity; (3) vaccine efficacy; and (4) screening compounds that inhibit viral entry (63).

In this study, a construct expressing the C-prM-E polyprotein of ZIKV was used to package GFP reporter containing WNV replicon to generate RVPs similar to those generated with WNV (38, 39). WNV based RVPs have been used by the present inventors and others previously to study WNV E biology (29, 38, 39). ZIKV RVPs were generated using a codon optimized synthetic ZIKV C-prM-E construct that was co-transfected with WNV replicon construct (Rep/GFP). These RVPs were infectious in multiple cell lines and could be neutralized using anti-ZIKV antibodies or cross-neutralizing WNV immune sera. Although similar ZIKV RVPs have recently been used for anti-ZIKV response, the current approach involves detection of infected cells by flow cytometry (29, 40). While flow cytometry has its benefits, especially in minimizing human error and bias and can be readily used for large sample sizes, the plate-based assay may be more helpful in resource limiting conditions where flow cytometry is not available.

The inventors adapted the RVP assay to a 96-well plate format with a GFP readout that could be quantitated using a simple fluorescent microscope. The objective was to develop an assay that can replace PRNT, requires less time to complete, does not involve use of live ZIKV, is highly reproducible and can be used in resource limiting situations. The inventors tested the assay extensively in 96 well format and found that both the number of GFP+ cells and the neutralization sensitivity was highly reproducible. Both automated counting using imaging software or manual counting yielded similar results suggesting that the assay needs minimum infrastructure. For further ease and to facilitate the use of the assay, the inventors generated a stable cell line expressing ZIKV structural proteins (293T-C-prM-E-F6) that can be used for RVP production by transfecting with a GFP replicon construct, in the case WNV replicon. However, the same cell line could also be utilized to package ZIKV reporter replicons when those become available. Besides the elimination of the use of infectious virus, the assay also provides several key advantages that make it attractive for resource limiting areas. The assay requires simple to grow and maintain cell lines (293T-C-prM-E-F6 and Vero), standard transfection protocols, 96 well plates and a basic fluorescent microscope with a 4× objective. As in the case of PRNT, the plates can be fixed using formalin and saved for extended periods for quantitation of GFP positive cells at a later time. In The hands, the inventors have saved the fixed plates for up to 6 months without loss of GFP signal and quantified at different time points with comparable accuracy. With rapid spread of ZIKV in countries with limited scientific infrastructure, this assay would be a valuable tool to assess ZIKV neutralizing antibodies in response to either vaccination drives and/or natural infection with ZIKV or related flaviviruses. Recently, a number of studies have investigated vaccine candidates for ZIKV. These include conventional approaches like use of purified inactivated virus (PIV) (20, 21), DNA (20-22), adenoviral-based subunit vaccines incorporating prM-E or M-E regions of ZIKV (20, 23) as well as lipid nanoparticle (LNP) encapsulated RNA or modified mRNA as vaccine candidates (24-26). These studies have demonstrated effective neutralizing antibody responses capable of protecting against ZIKV infection in various animal models. Recruitment of human subjects for testing some of these vaccine candidates is ongoing (NCT02963909, NCT02840487, NCT02887482, NCT02809443, NCT02952833). The geographical distribution of ZIKV is largely in developing and underdeveloped areas of the world (64). Hence, besides safety and efficacy being the top priorities for a successful vaccine, an important practical aspect for ZIKV vaccine is cost effectiveness and ease of production. In this regard, VLP based vaccines especially from cells lines stably expressing and releasing ZIKV proteins are highly attractive. The 293T-prM-E cell lines provide a much needed resource to take ZIKV VLP vaccines from the bench to the bedside. Not only do these cell lines release copious amount of E protein in the supernatant, but VLPs produced from these cells generate a robust neutralizing antibody response in mice making it ideal for further vaccine development.

The inventors also found that VLP vaccines were more efficacious than their DNA counterparts in inducing a neutralizing antibody response. In contrast, other studies have reported higher antibody titers upon immunization with a single dose of prM-E DNA (22) or prM-E modified RNA (25). This could be due to use of heterologous signal sequence from JEV to improve expression, use of stem/transmembrane region of the E protein from JEV to improve particle secretion (22) or use of signal peptide from MHC class II (25). Moreover, while C-prM-E VLPs worked better than prM-E VLPs, the C-prM-E DNA based vaccine was relatively non-efficacious. This is largely because the flavivirus NS3 enzyme along with the cofactor NS2B forms an active protease that cleaves the flavivirus C protein that spans the ER membrane producing its mature form (35, 50). Processing of the C protein by the viral protease in the ER is important for subsequent cleavage of E protein from prM by ER resident signal peptidases (50, 65). Interestingly, this study finds that inclusion of capsid in VLPs generates a better neutralizing immune response. However, it has been proposed that in the absence of an RNA genome, the nucleocapsid does not form and hence no capsid would be released into the supernatant (66) debating the benefit of a C-prM-E based vaccine.

Studies have suggested that T cells play an important role in generating a functional immune response in the presence of the viral capsid for Hepatitis B and C viruses (67, 68). Similarly, for DENV-4, epitopes in the capsid were shown to be recognized by CTLs that were cross reactive with other dengue serotypes (33). In fact, immunization by capsid alone was shown to generate a protective immune response independent of neutralizing antibodies and largely dependent on cell-mediated immunity (34). Moreover, CD4 T cells may also be involved in protection as specialized subsets have been implicated in lysing flavivirus infected cells (33, 69). Interestingly, The study shows that inclusion of capsid in VLPs requires a functional flavivivral protease, in the case WNV NS2B-3 fusion protein. The NS2B-3 fusion protein sequence itself is about 2Kb and can be easily included in VLP platforms, DNA vaccines as well as modified mRNA vaccines.

In summary, the inventors describe the development, testing and efficacy of a VLP based vaccine against ZIKV and the generation of stable cell lines to facilitate this platform. The inventors also describe the optimization of a RVP based microneutralization assay using ZIKV C-PrM-E cell line and WNV replicon/GFP. This assay recapitulates the standard PRNT routinely used by virologists with several advantages including ease of use, reproducibility and eliminating infectious virus use. Thus, the study addresses two most relevant aspects of ZIKV infection, a safe, effective and economical vaccine and a neutralization assay that could be employed in the fight against the current ZIKV outbreaks.

Zika virus isolate Z1106033 nucleic acid sequence, GenBank Accession No.
KU312312.1. Enfissi, A., Codrington, J., Roosblad, J., Kazanji, M. and
Rousset, D., "Zika virus genome from the Americas",
Lancet 387 (10015), 227-228 (2016).

SEQ ID NO: 1

```
   1 acaggtttta ttttggattt ggaaacgaga gtttctggtc atgaaaaacc caaaaaagaa
  61 atccggagga ttccggattg tcaatatgct aaaacgcgga gtagcccgtg tgagcccctt
 121 tgggggcttg aagaggctgc cagccggact tctgctgggt catgggccca tcaggatggt
 181 cttggcgatt ctagcctttt tgagattcac ggcaatcaag ccatcactgg gtctcatcaa
 241 tagatggggt tcagtgggga aaaagaggc tatggaaata taaagaagt tcaagaaaga
 301 tctggctgcc atgctgagaa taatcaatgc taggaaggag aagaagagac gaggcgcaga
 361 tactagtgtc ggaattgttg gcctcctgct gaccacagct atggcagcgg aggtcactag
 421 acgtgggagt gcatactata tgtacttgga cagaaacgat gctggggagg ccatatcttt
 481 tccaaccaca ttggggatga ataagtgtta tatacagatc atggatcttg acacacgtg
 541 tgatgccacc atgagctatg aatgccctat gctggatgag ggggtggaac cagatgacgt
 601 cgattgttgg tgcaacacga cgtcaacttg ggttgtgtac ggaacctgcc atcacaaaaa
 661 aggtgaagca cggagatcta aagagctgt gacgctcccc tcccattcca ctaggaagct
 721 gcaaacgcgg tcgcaaacct ggttggaatc aagagaatac acaaagcact tgattagagt
 781 cgaaaattgg atattcagga accctggctt cgcgttagca gcagctgcca tcgcttggct
 841 tttgggaagc tcaacgagcc aaaaagtcat atacttggtc atgatactgc tgattgcccc
 901 ggcatacagc atcaggtgca taggagtcag caatagggac tttgtggaag tatgtcagg
 961 tgggacttgg gttgatgttg tcttggaaca tggaggttgt gtcactgtaa tggcacagga
1021 caaaccgact gtcgacatag agctggttac aacaacagtc agcaacatgg cggaggtaag
1081 atcctactgc tatgaggcat caatatcaga catggcttcg gacagccgct gcccaacaca
1141 aggtgaagcc taccttgaca agcaatcaga cactcaatat gtctgcaaaa gaacgttagt
1201 ggacagaggc tggggaaatg gatgtggact ttttggcaaa gggagcctgg tgacatgcgc
1261 taagtttgca tgctccaaga aaatgaccgg gaagagcatc agccagaga atctggagta
1321 ccgataatg ctgtcagttc atggctccca gcacagtggg atgatcgtta atgacacagg
1381 acatgaaact gatgagaata gagcgaaagt tgagataacg cccaattcac aagagccga
1441 agccacctg gggggttg gaagcctagg acttgattgt gaaccgagga caggccttga
1501 cttttcagat tgtattact tgactatgaa taacaagcac tggctggttc acaaggagtg
1561 gttccacgac attccattac cttggcacgc tgggggcagac accggaactc cacactggaa
1621 caacaaagaa gcactggtag agttcaagga cgcacatgcc aaaaggcaaa ctgtcgtggt
1681 tctagggagt caagaaggag cagttcacac ggcccttgct ggagctctgg aggctgagat
1741 ggatggtgca aagggaaggc tgtcctctgg ccacttgaaa tgtcgcctga aaatggataa
1801 acttagattg aagggcgtgt catactccctt gtgtactgca gcgttcacat tcaccaagat
1861 cccggctgaa acactgcacg ggacagtcac agtggaggta cagtacgcag ggacagatgg
1921 accttgcaag gttccagctc agatggcgt ggacatgcaa actctgaccc cagttgggag
1981 gttgataacc gctaaccccg taatcactga aagcactgag aactctaaga tgatgctgga
2041 acttgatcca cctttgggg actcttacat tgtcatagga gtcggggaga agaagatcac
2101 ccaccactgg cacaggagtg gcagcaccat tggaaaagca tttgaagcca ctgtgagagg
2161 tgccaagaga atggcagtct gggagacac agcctgggac tttggatcag ttggaggcgc
2221 tctcaactca ttgggcaagg gcatccatca aatctttgga gcagctttca atcattgtt
```

-continued

```
2281 tggaggaatg tcctggttct cacaaattct cattggaacg ttgctgatgt ggttgggtct
2341 gaacgcaaag aatggatcta tttcccttat gtgcttggcc ttaggggag tgttgatctt
2401 cttatccaca gccgtctctg ctgatgtggg gtgctcggtg acttctcaa agaaggagac
2461 gagatgcggt acaggggtgt tcgtctataa cgacgttgaa gcctggaggg acaggtacaa
2521 gtaccatcct gactccccc gtagattggc agcagcagta aagcaagcct gggaagatgg
2581 tatctgcggg atctcctctg tttcaagaat ggaaaacatc atgtggagat cagtagaagg
2641 ggagctcaac gcaatcctgg aagagaatgg agttcaactg acggtcgttg tgggatctgt
2701 aaaaaacccc atgtggagag gtccacagag attgcccgtg cctgtgaacg agctgcccca
2761 cggctggaag gcttggggga aatcgtactt cgtcagagca gcaaagacaa ataacagctt
2821 tgtcgtggat ggtgacacac tgaaggaatg cccactcaaa catagagcat ggaacagctt
2881 tcttgtggag gatcatgggt tcggggtatt tcacactagt gtctggctca aggttagaga
2941 agattattca ttagagtgtg atccagccgt tattggaaca gctgttaagg gaaaggaggc
3001 tgtacacagt gatctaggct actggattga gagtgagaag aatgacacat ggaggctgaa
3061 gagggcccat ctgatcgaga tgaaaacatg tgaatggcca aagtcccaca cattgtggac
3121 agatggaata aagagagtg atctgatcat acccaagtct ttagctgggc cactcagcca
3181 tcacaatacc agagagggct acaggaccca atgaaaggg ccatggcaca gtgaagagct
3241 tgaaattcgg tttgaggaat gcccaggcac taaggtccac gtggaggaaa catgtggaac
3301 gagaggacca tctctgagat caaccactgc aagcggaagg gtgatcgagg aatggtgctg
3361 cagggagtgc acaatgcccc cactgtcgtt ccgggctaaa gatggctgtt ggtatggaat
3421 ggagataagg cccaggaaag aaccagaaag caacttagta aggtcaatgg tgactgcagg
3481 atcaactgat cacatggacc acttctccct tggagtgctt gtgattctgc tcatggtgca
3541 ggaagggttg aagaagagaa tgaccacaaa gatcatcata agcacatcaa tggcagtgct
3601 ggtagctatg atcctggag gattttcaat gagtgacctg gctaagcttg caattttgat
3661 gggtgccacc ttcgcggaaa tgaacactgg aggagatgta gctcatctgg cgctgatagc
3721 ggcattcaaa gtcagaccag cgttgctggt atctttcatc ttcagagcta attggacacc
3781 ccgtgaaagc atgctgctgg ccttggcctc gtgtcttttg caaactgcga tctccgcctt
3841 ggaaggcgac ctgatggttc tcatcaatgg ttttgctttg gcctggttgg caatacgagc
3901 gatggttgtt ccacgcactg ataacatcac cttggcaatc ctggctgctc tgacaccact
3961 ggccgggc acactgcttg tggcgtggag agcaggcctt gctacttgcg ggggtttat
4021 gctcctctct ctgaagggaa aaggcagtgt gaagaagaac ttaccatttg tcatggccct
4081 gggactaacc gctgtgaggc tggtcgaccc catcaacgtg tgggactgc tgttgctcac
4141 aaggagtggg aagcggagct ggccccctag cgaagtactc acagctgttg gcctgatatg
4201 cgcattggct ggagggttcg ccaaggcaga tatagagatg gctgggccca tggccgcggt
4261 cggtctgcta attgtcagtt acgtggtctc aggaaagagt gtggacatgt acattgaaag
4321 agcaggtgac atcacatggg aaaaagatgc ggaagtcact ggaaacagtc cccggctcga
4381 tgtggcgcta gatgagagtg gtgatttctc cctggtggag gatgacggtc ccccatgag
4441 agagatcata ctcaaggtgg tcctgatgac catctgtggc atgaacccaa tagccatacc
4501 ctttgcagct ggagcgtggt acgtatacgt gaagactgga aaaggagtg tgctctatg
4561 ggatgtgcct gctcccaagg aagtaaaaaa gggggagacc acagatggag tgtacagagt
4621 aatgactcgt agactgctag gttcaacaca agttggagtg ggagttatgc aagaggggt
4681 ctttcacact atgtggcacg tcacaaaagg atccgcgctg agaagcggtg aagggagact
```

```
4741  tgatccatac tggggagatg tcaagcagga tctggtgtca tactgtggtc catggaagct
4801  agatgccgcc tgggacgggc acagcgaggt gcagctcttg gccgtgcccc ccgagagag
4861  agcgaggaac atccagactc tgcccggaat atttaagaca aaggatgggg acattggagc
4921  ggttgcgctg gattacccag caggaacttc aggatctcct atcctagaca agtgtgggag
4981  agtgatagga ctttatggca atggggtcgt gatcaaaaat gggagttatg ttagtgccat
5041  cacccaaggg aggagggagg aagagactcc tgttgagtgc ttcgagcctt cgatgctgaa
5101  gaagaagcag ctaactgtct tagacttgca tcctggagct gggaaaacca ggagagttct
5161  tcctgaaata gtccgtgaag ccataaaaac aagactccgt actgtgatct tagctccaac
5221  cagggttgtc gctgctgaaa tggaggaggc ccttagaggg cttccagtgc gttatatgac
5281  aacagcagtc aatgtcaccc actctggaac agaaatcgtc gacttaatgt gccatgccac
5341  cttcacttcg cgtctactac agccaatcag agtccccaac tataatctgt atattatgga
5401  tgaggcccac ttcacagatc cctcaagtat agcagcaaga ggatacattt caacaagggt
5461  tgagatgggc gaggcggccg ccatcttcat gaccgccacg ccaccaggaa cccgtgacgc
5521  atttccggac tccaactcac caattatgga caccgaagtg gaagtcccag agagagcctg
5581  gagctcaggc tttgattggg tgacggatca ttctggaaaa acagtttggt ttgttccaag
5641  cgtgaggaac ggcaatgaga tcgcagcttg tctgacaaag gctggaaaac gggtcataca
5701  gctcagcaga aagactttg agacagagtt ccagaaaaca aaacatcaag agtgggactt
5761  tgtcgtgaca actgacattt cagagatggg cgccaacttt aaagctgacc gtgtcataga
5821  ttccaggaga tgcctaaagc cggtcatact tgatggcgag agagtcattc tggctggacc
5881  catgcctgtc acacatgcca gcgctgccca gaggaggggg cgcataggca ggaatcccaa
5941  caaacctgga gatgagtatc tgtatggagg tgggtgcgca gagactgacg aagaccatgc
6001  acactggctt gaagcaagaa tgctccttga caatatttac ctccaagatg gcctcatagc
6061  ctcgctctat cgacctgagg ccgacaaagt agcagccatt gagggagagt tcaagcttag
6121  gacggagcaa aggaagacct ttgtggaact catgaaaaga ggagatcttc ctgtttggct
6181  ggcctatcag gttgcatctg ccggaataac ctacacagat agaagatggt gctttgatgg
6241  cacgaccaac aacaccataa tggaagacag tgtgccggca gaagtgtgga ccagacacgg
6301  agagaaaaga gtgctcaaac cgaggtggat ggacgccaga gtttgttcag atcatgcggc
6361  cctgaagtca ttcaaggagt ttgccgctgg gaaaagagga gcggcttttg gagtgatgga
6421  agccctggga acactgccag acacatgac agagagattc caggaagcca ttgacaacct
6481  cgctgtgctc atgcgggcag agactggaag caggccttac aaagccgcgg cggcccaatt
6541  gccggagacc ctagagacca ttatgctttt ggggttgctg ggaacagtct cgctgggaat
6601  cttcttcgtc ttgatgagga caagggcat agggaagatg gctttggaa tggtgactct
6661  tggggccagc gcatggctca tgtggctctc ggaaattgag ccagccagaa ttgcatgtgt
6721  cctcattgtt gtgttcctat tgctggtggt gctcataccgt gagccagaaa agcaaagatc
6781  tccccaggac aaccaaatgg caatcatcat catggtagca gtaggtcttc tgggcttgat
6841  taccgccaat gaactcggat ggttggagag aacaaagagt gacctaagcc atctaatggg
6901  aaggagagag gagggggcaa ccataggatt ctcaatggac attgacctgg ggcagcctc
6961  agcttgggcc atctatgctg ccttgacaac tttcattacc ccagccgtcc aacatgcagt
7021  gaccacctca tacaacaact actccttaat ggcgatggcc acgcaagctg gagtgttgtt
7081  tggtatgggc aaagggatgc cattctacgc atgggacttt ggagtcccgc tgctaatgat
```

-continued

```
7141 aggttgctac tcacaattaa caccsctgac cctaatagtg gccatcattt tgctcgtggc
7201 gcactacatg tacttgatcc cagggctgca ggcagcagct gcgcgtgctg cccagaagag
7261 aacggcagct ggcatcatga agaaccctgt tgtggatgga atagtggtga ctgacattga
7321 cacaatgaca attgaccccc aagtggagaa aaagatggga caggtgctac tcatagcagt
7381 agccgtctcc agcgccatac tgtcgcggac cgcctggggg tgggggagg tcggggccct
7441 gatcacagcc gcaacttcca ctttgtggga aggctctccg aacaagtact ggaactcctc
7501 tacagccact tcactgtgta acatttttag gggaagttac ttggctggag cttctctaat
7561 ctacacagta acaagaaacg ctggcttggt caagacgtg ggggtggaa caggagagac
7621 cctgggagag aaatggaagg cccgcttgaa ccagatgtcg gccctggagt tctactccta
7681 caaaaagtca ggcatcaccg aggtgtgcag agaagaggcc cgccgcgccc tcaaggacgg
7741 tgtggcaacg ggaggccatg ctgtgtcccg aggaagtgca aagctgagat ggttggtgga
7801 gcggggatac ctgcagccct atggaaaggt cattgatctt ggatgtggca gaggggctg
7861 gagttactac gccgccacca tccgcaaagt tcaagaagtg aaaggataca caaaaggagg
7921 ccctggtcat gaagaacccg tgttggtgca aagctatggg tggaacatag tccgtcttaa
7981 gagtggggtg gacgtctttc atatggcggc tgagccgtgt gacacgttgc tgtgtgacat
8041 aggtgagtca tcatctagtc ctgaagtgga agaagcacgg acgctcagag tcctctccat
8101 ggtgggggat tggcttgaaa aaagaccagg agccttttgt ataaaagtgt tgtgcccata
8161 caccagcact atgatggaaa ccctggagcg actgcagcgt aggtatgggg gaggactggt
8221 cagagtgcca ctctcccgca actctacaca tgagatgtac tgggtctctg gagcgaaaag
8281 caacaccata aaaagtgtgt ccaccacgag ccagctcctc ttggggcgca tggacgggcc
8341 taggaggcca gtgaaatatg aggaggatgt gaatctcggc tctggcacgc gggctgtggt
8401 aagctgcgct gaagctccca acatgaagat cattggtaac cgcattgaaa ggatccgcag
8461 tgagcacgcg gaaacgtggt tctttgacga gaaccaccca tataggacat gggcttacca
8521 tggaagctat gaggcccca cacaagggtc agcgtcctct ctaataaacg gggttgtcag
8581 gctcctgtca aaaccctggg atgtggtgac tggagtcaca ggaatagcca tgaccgacac
8641 cacaccgtat ggtcagcaaa gagttttcaa ggaaaaagtg gacactaggg tgccagaccc
8701 ccaagaaggc actcgtcagg ttatgagcat ggtctcttcc tggttgtgga aagagctagg
8761 caaacacaaa cggccacgag tctgtaccaa agaagagttc atcaacaagg ttcgtagcaa
8821 tgcagcatta ggggcaatat ttgaagagga aaaagagtgg aagactgcag tggaagctgt
8881 gaacgatcca aggttctggg ctctagtgga caaggaaaga gagcaccacc tgagaggaga
8941 gtgccagagt tgtgtgtaca acatgatggg aaaaagagaa aagaaacaag gggaatttgg
9001 aaaggccaag ggcagccgcg ccatctggta tatgtggcta ggggctagat ttctagagtt
9061 cgaagccctt ggattcttga cgaggatca ctggatgggg agagagaact caggaggtgg
9121 tgttgaaggg ctgggattac aaagactcgg atatgtccta gaagagatga gtcgtatacc
9181 aggaggaagg atgtatgcag atgacactgc tggctgggac acccgcatta gcaggtttga
9241 tctggagaat gaagctctaa tcaccaacca aatggagaaa gggcacaggg ccttggcatt
9301 ggccataatc aagtacacat accaaaacaa agtggtaaag gtccttagac cagctgaaaa
9361 agggaaaaca gttatggaca ttatttcgag acaagaccaa ggggagcg acaagttgt
9421 cacttacgct cttaacacat ttaccaacct agtggtgcaa ctcattcgga atatggaggc
9481 tgaggaagtt ctagagatgc aagacttgtg gctgctgcgg aggtcagaga agtgactaa
9541 ctggttgcag agcaacggat gggataggct caaacgaatg gcagtcagtg gagatgattg
```

-continued

```
 9601 cgttgtgaag ccaattgatg ataggtttgc acatgccctc aggttcttga atgatatggg
 9661 aaaagttagg aaggacacac aagagtggaa accctcaact ggatgggaca actgggaaga
 9721 agttccgttt tgctcccacc acttcaacaa gctccatctc aaggacggga ggtccattgt
 9781 ggttccctgc cgccaccaag atgaactgat tggccgggcc cgcgtctctc caggggcggg
 9841 atggagcatc cggagactg cttgcctagc aaaatcatat gcgcaaatgt ggcagctcct
 9901 ttatttccac agaagggacc tccgactgat ggccaatgcc atttgttcat ctgtgccagt
 9961 tgactgggtt ccaactggga gaactacctg gtcaatccat ggaaagggag aatggatgac
10021 cactgaagac atgcttgtgg tgtggaacag agtgtggatt gaggagaacg accacatgga
10081 agacaagacc ccagttacga aatggacaga cattccctat ttgggaaaaa gggaagactt
10141 gtggtgtgga tctctcatag ggcacagacc gcgcaccacc tgggctgaga acattaaaaa
10201 cacagtcaac atggtgcgca ggatcatagg tgatgaagaa aagtacatgg actacctatc
10261 cacccaagtt gcgtacttgg gtgaagaagg gtctacacct ggagtgctgt aagcaccaat
10321 cttaatgttg tcaggcctgc tagtcagcca cagcttgggg aaagctgtgc agcc,
```

Zika virus isolate Z1106033 polyprotein GenBank Accession No. KU312312.1.
SEQ ID NO: 2

MKNPKKKSGGFRIVNMLKRGVARVSPFGGLKRLPAGLLLGHGPIRMVLAILAFLRFTAI
KPSLGLINRWGSVGKKEAMEIIKKFKKDLAAMLRIINARKEKKRRGADTSVGIVGLLLT
TAMAAEVTRRGSAYYMYLDRNDAGEAISFPTTLGMNKCYIQIMDLGHTCDATMSYEC
PMLDEGVEPDDVDCWCNTTSTWVVYGTCHHKKGEARRSRRAVTLPSHSTRKLQTRSQ
TWLESREYTKHLIRVENWIFRNPGFALAAAAIAWLLGSSTSQKVIYLVMILLIAPAYSIRC
IGVSNRDFVEGMSGGTWVDVVLEHGGCVTVMAQDKPTVDIELVTTTVSNMAEVRSYC
YEASISDMASDSRCPTQGEAYLDKQSDTQYVCKRTLVDRGWGNGCGLFGKGSLVTCA
KFACSKKMTGKSIQPENLEYRIMLSVHGSQHSGMIVNDTGHETDENRAKVEITPNSPRA
EATLGGFGSLGLDCEPRTGLDFSDLYYLTMNNKHWLVHKEWFHDIPLPWHAGADTGT
PHWNNKEALVEFKDAHAKRQTVVVLGSQEGAVHTALAGALEAEMDGAKGRLSSGHL
KCRLKMDKLRLKGVSYSLCTAAFTFTKIPAETLHGTVTVEVQYAGTDGPCKVPAQMAV
DMQTLTPVGRLITANPVITESTENSKMMLELDPPFGDSYIVIGVGEKKITHHWHRSGSTI
GKAFEATVRGAKRMAVLGDTAWDFGSVGGALNSLGKGIHQIFGAAFKSLFGGMSWFS
QILIGTLLMWLGLNAKNGSISLMCLALGGVLIFLSTAVSADVGCSVDFSKKETRCGTGV
FVYNDVEAWRDRYKYHPDSPRRLAAAVKQAWEDGICGISSVSRMENIMWRSVEGELN
AILEENGVQLTVVVGSVKNPMWRGPQRLPVPVNELPHGWKAWGKSYFVRAAKTNNSF
VVDGDTLKECPLKHRAWNSFLVEDHGFGVFHTSVWLKVREDYSLECDPAVIGTAVKG
KEAVHSDLGYWIESEKNDTWRLKRAHLIEMKTCEWPKSHTLWTDGIEESDLIIPKSLAG
PLSHHNTREGYRTQMKGPWHSEELEIRFEECPGTKVHVEETCGTRGPSLRSTTASGRVIE
EWCCRECTMPPLSFRAKDGCWYGMEIRPRKEPESNLVRSMVTAGSTDHMDHFSLGVL
VILLMVQEGLKKRMTTKIIISTSMAVLVAMILGGFSMSDLAKLAILMGATFAEMNTGGD
VAHLALIAAFKVRPALLVSFIFRANWTPRESMLLALASCLLQTAISALEGDLMVLINGFA
LAWLAIRAMVVPRTDNITLAILAALTPLARGTLLVAWRAGLATCGGFMLLSLKGKGSV
KKNLPFVMALGLTAVRLVDPINVVGLLLLTRSGKRSWPPSEVLTAVGLICALAGGFAKA
DIEMAGPMAAVGLLIVSYVVSGKSVDMYIERAGDITWEKDAEVTGNSPRLDVALDESG
DFSLVEDDGPPMREIILKVVLMTICGMNPIAIPFAAGAWYVYVKTGKRSGALWDVPAP

-continued

KEVKKGETTDGVYRVMTRRLLGSTQVGVGVMQEGVFHTMWHVTKGSALRSGEGRLD

PYWGDVKQDLVSYCGPWKLDAAWDGHSEVQLLAVPPGERARNIQTLPGIFKTKDGDI

GAVALDYPAGTSGSPILDKCGRVIGLYGNGVVIKNGSYVSAITQGRREEETPVECFEPSM

LKKKQLTVLDLHPGAGKTRRVLPEIVREAIKTRLRTVILAPTRVVAAEMEEALRGLPVR

YMTTAVNVTHSGTEIVDLMCHATFTSRLLQPIRVPNYNLYIMDEAHFTDPSSIAARGYIS

TRVEMGEAAAIFMTATPPGTRDAFPDSNSPIMDTEVEVPERAWSSGFDWVTDHSGKTV

WFVPSVRNGNEIAACLTKAGKRVIQLSRKTFETEFQKTKHQEWDFVVTTDISEMGANF

KADRVIDSRRCLKPVILDGERVILAGPMPVTHASAAQRRGRIGRNPNKPGDEYLYGGGC

AETDEDHAHWLEARMLLDNIYLQDGLIASLYRPEADKVAAIEGEFKLRTEQRKTFVEL

MKRGDLPVWLAYQVASAGITYTDRRWCFDGTTNNTIMEDSVPAEVWTRHGEKRVLKP

RWMDARVCSDHAALKSFKEFAAGKRGAAFGVMEALGTLPGHMTERFQEAIDNLAVL

MRAETGSRPYKAAAAQLPETLETIMLLGLLGTVSLGIFFVLMRNKGIGKMGFGMVTLG

ASAWLMWLSEIEPARIACVLIVVFLLLVVLIPEPEKQRSPQDNQMAIIIMVAVGLLGLITA

NELGWLERTKSDLSHLMGRREEGATIGFSMDIDLRPASAWAIYAALTTFITPAVQHAVT

TSYNNYSLMAMATQAGVLFGMGKGMPFYAWDFGVPLLMIGCYSQLTPLTLIVAIILLV

AHYMYLIPGLQAAAARAAQKRTAAGIMKNPVVDGIVVTDIDTMTIDPQVEKKMGQVL

LIAVAVSSAILSRTAWGWGEAGALITAATSTLWEGSPNKYWNSSTATSLCNIFRGSYLA

GASLIYTVTRNAGLVKRRGGGTGETLGEKWKARLNQMSALEFYSYKKSGITEVCREEA

RRALKDGVATGGHAVSRGSAKLRWLVERGYLQPYGKVIDLGCGRGGWSYYAATIRKV

QEVKGYTKGGPGHEEPVLVQSYGWNIVRLKSGVDVFHMAAEPCDTLLCDIGESSSSPE

VEEARTLRVLSMVGDWLEKRPGAFCIKVLCPYTSTMMETLERLQRRYGGGLVRVPLSR

NSTHEMYWVSGAKSNTIKSVSTTSQLLLGRMDGPRRPVKYEEDVNLGSGTRAVVSCAE

APNMKIIGNRIERIRSEHAETWFFDENHPYRTWAYHGSYEAPTQGSASSLINGVVRLLSK

PWDVVTGVTGIAMTDTTPYGQQRVFKEKVDTRVPDPQEGTRQVMSMVSSWLWKELG

KHKRPRVCTKEEFINKVRSNAALGAIFEEEKEWKTAVEAVNDPRFWALVDKEREHHLR

GECQSCVYNMMGKREKKQGEFGKAKGSRAIWYMWLGARFLEFEALGFLNEDHWMG

RENSGGGVEGLGLQRLGYVLEEMSRIPGGRMYADDTAGWDTRISRFDLENEALITNQM

EKGHRALALAIIKYTYQNKVVKVLRPAEKGKTVMDIISRQDQRGSGQVVTYALNTFTN

LVVQLIRNMEAEEVLEMQDLWLLRRSEKVTNWLQSNGWDRLKRMAVSGDDCVVKPI

DDRFAHALRFLNDMGKVRKDTQEWKPSTGWDNWEEVPFCSHHFNKLHLKDGRSIVVP

CRHQDELIGRARVSPGAGWSIRETACLAKSYAQMWQLLYFHRRDLRLMANAICSSVPV

DWVPTGRTTWSIHGKGEWMTTEDMLVVWNRVWIEENDHMEDKTPVTKWTDIPYLGK

REDLWCGSLIGHRPRTTWAENIKNTVNMVRRIIGDEEKYMDYLSTQVRYLGEEGSTPG

VL.

codon optimized Zika C-prM-E synthesized.

SEQ ID NO: 3

ATGAAGAATCCCAAGAAGAAATCTGGCGGGTTCCGAATCG

TCAATATGCTGAAGAGAGGAGTGGCAAGAGTGTCACCTTTTGGCG

GGCTGAAGAGGCTGCCTGCAGGACTGCTGCTGGGGCACGGACCAA

TCAGGATGGTGCTGGCAATTCTGGCCTTCCTGCGCTTTACCGCTA

TCAAACCCAGCCTGGGCCTGATTAATCGCTGGGGGTCCGTGGGAA

AGAAAGAGGCTATGGAGATCATCAAGAAGTTCAAGAAAGACCTGG

```
CCGCTATGCTGCGGATCATTAACGCTAGAAAGGAGAAGAAACGGA

GAGGGGCAGATACCTCTGTGGGCATCGTCGGGCTGCTGCTGACCA

CAGCAATGGCAGCCGAGGTGACAAGGCGCGGATCAGCCTACTATA

TGTACCTGGACCGGAATGATGCTGGCGAAGCAATCAGCTTCCCAA

CTACCCTGGGGATGAACAAGTGCTACATCCAGATTATGGACCTGG

GCCACACATGCGATGCCACCATGAGCTATGAGTGTCCAATGCTGG

ACGAGGGGTGGAACCCGACGATGTCGATTGCTGGTGTAATACAA

CTTCCACTTGGGTGGTCTACGGCACCTGTCACCATAAGAAAGGAG

AAGCTCGGCGGAGCCGGAGGGCAGTGACACTGCCATCACACAGCA

CTAGGAAGCTGCAGACACGCAGCCAGACTTGGCTGGAGTCCAGAG

AATATACAAAACATCTGATCAGAGTGGAGAACTGGATCTTCCGGA

ATCCAGGATTCGCACTGGCTGCAGCCGCTATCGCATGGCTGCTGG

GCAGCTCCACCTCTCAGAAAGTGATCTACCTGGTCATGATCCTGC

TGATTGCCCCCGCTTATTCTATCCGCTGCATTGGGGTGAGTAATC

GAGACTTCGTCGAGGGAATGAGCGGCGGGACATGGGTGGATGTGG

TCCTGGAACACGGAGGCTGCGTGACTGTGATGGCTCAGGACAAGC

CTACCGTGGATATCGAGCTGGTGACCACAACTGTCTCAAACATGG

CCGAGGTGAGGAGCTACTGCTATGAAGCCTCCATTTCTGACATGG

CTAGTGATTCACGCTGTCCAACCCAGGGCGAGGCCTACCTGGACA

AGCAGAGTGATACCCAGTACGTGTGCAAACGAACACTGGTCGACC

GGGGCTGGGGAATGGATGTGGCCTGTTTGGGAAGGGAAGCCTGG

TGACATGCGCCAAATTCGCTTGTTCCAAGAAAATGACTGGCAAGT

CTATCCAGCCTGAGAACCTGGAATACAGGATTATGCTGAGCGTGC

ACGGATCACAGCATAGCGGCATGATCGTCAACGACACCGGCCACG

AGACAGATGAAAATCGAGCCAAAGTGGAGATTACCCCTAACTCTC

CAAGAGCAGAAGCCACACTGGGGGGATTTGGAAGTCTGGGCCTGG

ACTGCGAGCCACGAACCGGCCTGGACTTCTCCGATCTGTACTATC

TGACAATGAACAATAAGCACTGGCTGGTGCATAAAGAATGGTTTC

ACGACATCCCACTGCCCTGGCATGCTGGAGCAGATACCGGCACAC

CTCACTGGAACAATAAGGAGGCCCTGGTGGAGTTCAAGGATGCCC

ATGCTAAACGGCAGACAGTGGTCGTGCTGGGGAGCCAGGAGGGAG

CAGTGCACACTGCACTGGCCGGCGCTCTGGAGGCAGAAATGGACG

GGGCCAAGGGAAGACTGTCTAGTGGGCATCTGAAATGCCGGCTGA

AGATGGATAAACTGAGACTGAAGGGAGTGAGCTACTCCCTGTGCA

CTGCAGCCTTCACTTTTACCAAAATCCCAGCTGAGACACTGCACG

GCACAGTCACTGTGGAAGTCCAGTATGCCGGCACTGACGGCCCTT

GTAAGGTGCCTGCACAGATGGCCGTCGATATGCAGACCCTGACAC

CAGTGGGCCGGCTGATCACCGCCAATCCTGTCATTACTGAGAGTA

CCGAAAACTCAAAAATGATGCTGGAGCTGGACCCCCCTTTTGGGG

ATTCCTATATCGTGATTGGCGTCGGGGAAAAGAAAATCACACACC
```

```
ATTGGCACCGGAGCGGCAGTACAATTGGGAAGGCTTTTGAGGCAA

CTGTGCGCGGCGCCAAACGAATGGCTGTCCTGGGAGACACCGCAT

GGGATTTCGGCAGTGTGGGAGGGGCTCTGAACTCACTGGGAAAGG

GCATCCATCAGATTTTCGGAGCTGCCTTCAAGAGCCTGTTCGGAG

GCATGTCCTGGTTCTCTCAGATCCTGATTGGCACTCTGCTGATGT

GGCTGGGGCTGAACGCCAAGAATGGCAGCATCAGTCTGATGTGCC

TGGCCCTGGGGGGGGTCCTGATTTTCCTGTCAACCGCAGTCTCCG

CTGACTGATGA, codon optimized amino acid sequence of Zika C-prM-E

MKNPKKKSGGFRIVNMLKRGVARVSPFGGLKRLPAGLLLGHPIRMVLAI

LAFLRFTAIKPSLGLINRWGSVGKKEAMEIIKKFKKDLAAMLRIINARKE

KKRRGADTSVGIVGLLLTTAMAAEVTRRGSAYYMYLDRNDAGEAISFPTT

LGMNKCYIQIMDLGHTCDATMSYECPMLDEGVEPDDVDCWCNTTSTWVVY

GTCHHKKGEARRSRRAVTLPSHSTRKLQTRSQTWLESREYTKHLIRVENW

IFRNPGFALAAAAIAWLLGSSTSQKVIYLVMILLIAPAYSIRCIGVSNRD

FVEGMSGGTWVDVVLEHGGCVTVMAQDKPTVDIELVTTTVSNMAEVRSYC

YEASISDMASDSRCPTQGEAYLDKQSDTQYVCKRTLVDRGWGNGCGLFGK

GSLVTCAKFACSKKMTGKSIQPENLEYRIMLSVHGSQHSGMIVNDTGHET

DENRAKVEITPNSPRAEATLGGFGSLGLDCEPRTGLDFSDLYYLTMNNKH

WLVHKEWFHDIPLPWHAGADTGTPHWNNKEALVEFKDAHAKRQTVVVLGS

QEGAVHTALAGALEAEMDGAKGRLSSGHLKCRLKMDKLRLKGVSYSLCTA

AFTFTKIPAETLHGTVTVEVQYAGTDGPCKVPAQMAVDMQTLTPVGRLIT

ANPVITESTENSKMMLELDPPFGDSYIVIGVGEKKITHHWHRSGSTIGKA

FEATVRGAKRMAVLGDTAWDFGSVGGALNSLGKGIHQIFGAAFKSLFGGM

SWFSQILIGTLLMWLGLNAKNGSISLMCLALGGVLIFLSTAVSAD,
```

SEQ ID NO: 4

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Dick G W. 1952. Zika virus. II. Pathogenicity and physical properties. Trans R Soc Trop Med Hyg 46:521-34.
2. Dick G W, Kitchen S F, Haddow A J. 1952. Zika virus. I. Isolations and serological specificity. Trans R Soc Trop Med Hyg 46:509-20.
3. Duffy M R, Chen T H, Hancock W T, Powers A M, Kool J L, Lanciotti R S, Pretrick M, Marfel M, Holzbauer S, Dubray C, Guillaumot L, Griggs A, Bel M, Lambert A J, Laven J, Kosoy O, Panella A, Biggerstaff B J, Fischer M, Hayes E B. 2009. Zika virus outbreak on Yap Island, Federated States of Micronesia. N Engl J Med 360:2536-43.
4. Simpson D I. 1964. Zika Virus Infection in Man. Trans R Soc Trop Med Hyg 58:335-8.
5. Brasil P, Pereira J P, Jr., Moreira M E, Ribeiro Nogueira R M, Damasceno L, Wakimoto M, Rabello R S, Valderramos S G, Halai U A, Salles T S, Zin A A, Horovitz D, Daltro P, Boechat M, Raja Gabaglia C, Carvalho de Sequeira P, Pilotto J H, Medialdea-Carrera R, Cotrim da Cunha D, Abreu de Carvalho L M, Pone M, Machado Siqueira A, Calvet G A, Rodrigues Baiao A E, Neves E S, Nassar de Carvalho P R, Hasue R H, Marschik P B, Einspieler C, Janzen C, Cherry J D, Bispo de Filippis A M, Nielsen-Saines K. 2016. Zika Virus Infection in Pregnant Women in Rio de Janeiro. N Engl J Med 375:2321-2334.
6. Enfissi A, Codrington J, Roosblad J, Kazanji M, Rousset D. 2016. Zika virus genome from the Americas. Lancet 387:227-8.
7. Rasmussen S A, Jamieson D J, Honein M A, Petersen L R. 2016. Zika Virus and Birth Defects—Reviewing the Evidence for Causality. N Engl J Med 374:1981-7.
8. Cao-Lormeau V M, Blake A, Mons S, Lastere S, Roche C, Vanhomwegen J, Dub T, Baudouin L, Teissier A, Larre P, Vial A L, Decam C, Choumet V, Halstead S K, Willison H J, Musset L, Manuguerra J C, Despres P, Fournier E, Mallet H P, Musso D, Fontanet A, Neil J, Ghawche F. 2016. Guillain-Barre Syndrome outbreak associated with Zika virus infection in French Polynesia: a case-control study. Lancet 387:1531-9.
9. Oehler E, Watrin L, Lane P, Leparc-Goffart I, Lastere S, Valour F, Baudouin L, Mallet H, Musso D, Ghawche F. 2014. Zika virus infection complicated by Guillain-Barre syndrome—case report, French Polynesia, December 2013. Euro Surveill 19.
10. Davidson A, Slavinski S, Komoto K, Rakeman J, Weiss D. 2016. Suspected Female-to-Male Sexual Transmission of Zika Virus—New York City, 2016. MMWR Morb Mortal Wkly Rep 65:716-7.
11. Mansuy J M, Suberbielle E, Chapuy-Regaud S, Mengelle C, Buj an L, Marchou B, Delobel P, Gonzalez-Dunia D, Malnou C E, Izopet J, Martin-Blondel G. 2016. Zika virus in semen and spermatozoa. Lancet Infect Dis 16:1106-7.
12. Murray K O, Gorchakov R, Carlson A R, Berry R, Lai L, Natrajan M, Garcia M N, Correa A, Patel S M, Aagaard K, Mulligan M J. 2017. Prolonged Detection of Zika Virus in Vaginal Secretions and Whole Blood. Emerg Infect Dis 23:99-101.
13. Shi Y, Gao G F. 2017. Structural Biology of the Zika Virus. Trends Biochem Sci doi:10.1016/j.tibs.2017.02.009.
14. Stadler K, Allison S L, Schalich J, Heinz F X. 1997. Proteolytic activation of tick-borne encephalitis virus by furin. J Virol 71:8475-81.
15. Sapparapu G, Fernandez E, Kose N, Bin C, Fox J M, Bombardi R G, Zhao H, Nelson C A, Bryan A L, Barnes T, Davidson E, Mysorekar I U, Fremont D H, Doranz B J, Diamond M S, Crowe J E. 2016. Neutralizing human antibodies prevent Zika virus replication and fetal disease in mice. Nature 540:443-447.
16. Stettler K, Beltramello M, Espinosa D A, Graham V, Cassotta A, Bianchi S, Vanzetta F, Minola A, Jaconi S, Mele F, Foglierini M, Pedotti M, Simonelli L, Dowall S, Atkinson B, Percivalle E, Simmons C P, Varani L, Blum J, Baldanti F, Cameroni E, Hewson R, Harris E, Lanzavecchia A, Sallusto F, Corti D. 2016. Specificity, cross-reactivity, and function of antibodies elicited by Zika virus infection. Science 353:823-6.
17. Swanstrom J A, Plante J A, Plante K S, Young E F, McGowan E, Gallichotte E N, Widman D G, Heise M T, de Silva A M, Baric R S. 2016. Dengue Virus Envelope Dimer Epitope Monoclonal Antibodies Isolated from Dengue Patients Are Protective against Zika Virus. MBio 7.

18. Wang Q, Yang H, Liu X, Dai L, Ma T, Qi J, Wong G, Peng R, Liu S, Li J, Li S, Song J, Liu J, He J, Yuan H, Xiong Y, Liao Y, Li J, Yang J, Tong Z, Griffin B D, Bi Y, Liang M, Xu X, Qin C, Cheng G, Zhang X, Wang P, Qiu X, Kobinger G, Shi Y, Yan J, Gao G F. 2016. Molecular determinants of human neutralizing antibodies isolated from a patient infected with Zika virus. Sci Transl Med 8:369ra179.
19. Zhao H, Fernandez E, Dowd K A, Speer S D, Platt D J, Gorman M J, GoVero J, Nelson C A, Pierson T C, Diamond M S, Fremont D H. 2016. Structural Basis of Zika Virus-Specific Antibody Protection. Cell 166:1016-27.
20. Abbink P, Larocca R A, De La Barrera R A, Bricault C A, Moseley E T, Boyd M, Kirilova M, Li Z, Ng'ang'a D, Nanayakkara O, Nityanandam R, Mercado N B, Borducchi E N, Agarwal A, Brinkman A L, Cabral C, Chandrashekar A, Giglio P B, Jetton D, Jimenez J, Lee B C, Mojta S, Molloy K, Shetty M, Neubauer G H, Stephenson K E, Peron J P, Zanotto P M, Misamore J, Finneyfrock B, Lewis M G, Alter G, Modjarrad K, Jarman R G, Eckels K H, Michael N L, Thomas S J, Barouch D H. 2016. Protective efficacy of multiple vaccine platforms against Zika virus challenge in rhesus monkeys. Science 353: 1129-32.
21. Larocca R A, Abbink P, Peron J P, Zanotto P M, Iampietro M J, Badamchi-Zadeh A, Boyd M, Ng'ang'a D, Kirilova M, Nityanandam R, Mercado N B, Li Z, Moseley E T, Bricault C A, Borducchi E N, Giglio P B, Jetton D, Neubauer G, Nkolola J P, Maxfield L F, De La Barrera R A, Jarman R G, Eckels K H, Michael N L, Thomas S J, Barouch D H. 2016. Vaccine protection against Zika virus from Brazil. Nature 536:474-8.
22. Dowd K A, Ko S Y, Morabito K M, Yang E S, Pelc R S, DeMaso C R, Castilho L R, Abbink P, Boyd M, Nityanandam R, Gordon D N, Gallagher J R, Chen X, Todd J P, Tsybovsky Y, Harris A, Huang Y S, Higgs S, Vanlandingham D L, Andersen H, Lewis M G, De La Barrera R, Eckels K H, Jarman R G, Nason M C, Barouch D H, Roederer M, Kong W P, Mascola J R, Pierson T C, Graham B S. 2016. Rapid development of a DNA vaccine for Zika virus. Science 354:237-240.
23. Kim E, Erdos G, Huang S, Kenniston T, Falo L D, Jr., Gambotto A. 2016. Preventative Vaccines for Zika Virus Outbreak: Preliminary Evaluation. EBioMedicine 13:315-320.
24. Chahal J S, Fang T, Woodham A W, Khan O F, Ling J, Anderson D G, Ploegh H L. 2017. An RNA nanoparticle vaccine against Zika virus elicits antibody and CD8+ T cell responses in a mouse model. Sci Rep 7:252.
25. Pardi N, Hogan M J, Pelc R S, Muramatsu H, Andersen H, DeMaso C R, Dowd K A, Sutherland L L, Scearce R M, Parks R, Wagner W, Granados A, Greenhouse J, Walker M, Willis E, Yu J S, McGee C E, Sempowski G D, Mui B L, Tam Y K, Huang Y J, Vanlandingham D, Holmes V M, Balachandran H, Sahu S, Lifton M, Higgs S, Hensley S E, Madden T D, Hope M J, Kariko K, Santra S, Graham B S, Lewis M G, Pierson T C, Haynes B F, Weissman D. 2017. Zika virus protection by a single low-dose nucleoside-modified mRNA vaccination. Nature 543:248-251.
26. Richner J M, Himansu S, Dowd K A, Butler S L, Salazar V, Fox J M, Julander J G, Tang W W, Shresta S, Pierson T C, Ciaramella G, Diamond M S. 2017. Modified mRNA Vaccines Protect against Zika Virus Infection. Cell 169: 176.
27. Boigard H, Alimova A, Martin G R, Katz A, Gottlieb P, Galarza J M. 2017. Zika virus-like particle (VLP) based vaccine. PLoS Negl Trop Dis 11:e0005608.
28. Haddow A D, Schuh A J, Yasuda C Y, Kasper M R, Heang V, Huy R, Guzman H, Tesh R B, Weaver S C. 2012. Genetic characterization of Zika virus strains: geographic expansion of the Asian lineage. PLoS Negl Trop Dis 6:e1477.
29. Dowd K A, DeMaso C R, Pelc R S, Speer S D, Smith A R, Goo L, Platt D J, Mascola J R, Graham B S, Mulligan M J, Diamond M S, Ledgerwood J E, Pierson T C. 2016. Broadly Neutralizing Activity of Zika Virus-Immune Sera Identifies a Single Viral Serotype. Cell Rep 16:1485-91.
30. Maeda A, Maeda J. 2013. Review of diagnostic plaque reduction neutralization tests for flavivirus infection. Vet J 195:33-40.
31. Jeong H, Seong B L. 2017. Exploiting virus-like particles as innovative vaccines against emerging viral infections. J Microbiol 55:220-230.
32. Oliveira E R, Mohana-Borges R, de Alencastro R B, Horta B A. 2017. The flavivirus capsid protein: Structure, function and perspectives towards drug design. Virus Res 227:115-123.
33. Gagnon S J, Zeng W, Kurane I, Ennis F A. 1996. Identification of two epitopes on the dengue 4 virus capsid protein recognized by a serotype-specific and a panel of serotype-cross-reactive human CD4+ cytotoxic T-lymphocyte clones. J Virol 70:141-7.
34. Lazo L, Hermida L, Zulueta A, Sanchez J, Lopez C, Silva R, Guillen G, Guzman M G. 2007. A recombinant capsid protein from Dengue-2 induces protection in mice against homologous virus. Vaccine 25:1064-70.
35. Stocks C E, Lobigs M. 1998. Signal peptidase cleavage at the flavivirus C-prM junction: dependence on the viral NS2B-3 protease for efficient processing requires determinants in C, the signal peptide, and prM. J Virol 72:2141-9.
36. Henchal E A, Gentry M K, McCown J M, Brandt W E. 1982. Dengue virus-specific and flavivirus group determinants identified with monoclonal antibodies by indirect immunofluorescence. Am J Trop Med Hyg 31:830-6.
37. Lazear H M, Diamond M S. 2016. Zika Virus: New Clinical Syndromes and Its Emergence in the Western Hemisphere. J Virol 90:4864-75.
38. Garg H, Lee R T, Tek N O, Maurer-Stroh S, Joshi A. 2013. Identification of conserved motifs in the West Nile virus envelope essential for particle secretion. BMC Microbiol 13:197.
39. Pierson T C, Sanchez M D, Puffer B A, Ahmed A A, Geiss B J, Valentine L E, Altamura L A, Diamond M S, Doms R W. 2006. A rapid and quantitative assay for measuring antibody-mediated neutralization of West Nile virus infection. Virology 346:53-65.
40. Dowd K A, DeMaso C R, Pierson T C. 2015. Genotypic Differences in Dengue Virus Neutralization Are Explained by a Single Amino Acid Mutation That Modulates Virus Breathing. MBio 6:e01559-15.
41. Hasan S S, Miller A, Sapparapu G, Fernandez E, Klose T, Long F, Fokine A, Porta J C, Jiang W, Diamond M S, Crowe J E, Jr., Kuhn R J, Rossmann M G. 2017. A human antibody against Zika virus crosslinks the E protein to prevent infection. Nat Commun 8:14722.
42. Garg H, Lee R T, Maurer-Stroh S, Joshi A. 2016. HIV-1 adaptation to low levels of CCR5 results in V3 and V2 loop changes that increase envelope pathogenicity, CCR5 affinity and decrease susceptibility to Maraviroc. Virology 493:86-99.
43. Joshi A, Nyakeriga A M, Ravi R, Garg H. 2011. HIV ENV glycoprotein-mediated bystander apoptosis depends on expression of the CCR5 co-receptor at the cell surface and ENV fusogenic activity. J Biol Chem 286:36404-13.
44. Davis B S, Chang G J, Cropp B, Roehrig J T, Martin D A, Mitchell C J, Bowen R, Bunning M L. 2001. West Nile virus recombinant DNA vaccine protects mouse and horse from virus challenge and expresses in vitro a noninfectious recombinant antigen that can be used in enzyme-linked immunosorbent assays. J Virol 75:4040-7.
45. Ferlenghi I, Clarke M, Ruttan T, Allison S L, Schalich J, Heinz F X, Harrison S C, Rey F A, Fuller S D. 2001. Molecular organization of a recombinant subviral particle from tick-borne encephalitis virus. Mol Cell 7:593-602.
46. Hunt A R, Cropp C B, Chang G J. 2001. A recombinant particulate antigen of Japanese encephalitis virus produced in stably-transformed cells is an effective noninfectious antigen and subunit immunogen. J Virol Methods 97:133-49.
47. Mason P W, Pincus S, Fournier M J, Mason T L, Shope R E, Paoletti E. 1991. Japanese encephalitis virus-vaccinia recombinants produce particulate forms of the structural membrane proteins and induce high levels of protection against lethal JEV infection. Virology 180:294-305.
48. Pincus S, Mason P W, Konishi E, Fonseca B A, Shope R E, Rice C M, Paoletti E. 1992. Recombinant vaccinia virus producing the prM and E proteins of yellow fever virus protects mice from lethal yellow fever encephalitis. Virology 187:290-7.
49. Brien J D, Lazear H M, Diamond M S. 2013. Propagation, quantification, detection, and storage of West Nile virus. Curr Protoc Microbiol 31:15D 3 1-15D 3 18.
50. Lobigs M. 1993. Flavivirus premembrane protein cleavage and spike heterodimer secretion require the function of the viral proteinase NS3. Proc Natl Acad Sci USA 90:6218-22.
51. Bera A K, Kuhn R J, Smith J L. 2007. Functional characterization of cis and trans activity of the Flavivirus NS2B-NS3 protease. J Biol Chem 282:12883-92.
52. Wilson J R, de Sessions P F, Leon M A, Scholle F. 2008. West Nile virus nonstructural protein 1 inhibits TLR3 signal transduction. J Virol 82:8262-71.
53. Chambers T J, Hahn C S, Galler R, Rice C M. 1990. Flavivirus genome organization, expression, and replication. Annu Rev Microbiol 44:649-88.
54. Kuno G, Chang G J. 2007. Full-length sequencing and genomic characterization of Bagaza, Kedougou, and Zika viruses. Arch Virol 152:687-96.
55. Lindenbach B D, Rice C M. 2003. Molecular biology of flaviviruses. Adv Virus Res 59:23-61.
56. Gehrke R, Ecker M, Aberle S W, Allison S L, Heinz F X, Mandl C W. 2003. Incorporation of tick-borne encephalitis virus replicons into virus-like particles by a packaging cell line. J Virol 77:8924-33.
57. Lorenz I C, Kartenbeck J, Mezzacasa A, Allison S L, Heinz F X, Helenius A. 2003. Intracellular assembly and secretion of recombinant subviral particles from tick-borne encephalitis virus. J Virol 77:4370-82.
58. Pugachev K V, Mason P W, Shope R E, Frey T K. 1995. Double-subgenomic Sindbis virus recombinants expressing immunogenic proteins of Japanese encephalitis virus induce significant protection in mice against lethal JEV infection. Virology 212:587-94.
59. Noad R, Roy P. 2003. Virus-like particles as immunogens. Trends Microbiol 11:438-44.
60. Pattenden L K, Middelberg A P, Niebert M, Lipin D I. 2005. Towards the preparative and large-scale precision manufacture of virus-like particles. Trends Biotechnol 23:523-9.
61. Lo M K, Tilgner M, Shi P Y. 2003. Potential high-throughput assay for screening inhibitors of West Nile virus replication. J Virol 77:12901-6.
62. Shi P Y, Tilgner M, Lo M K. 2002. Construction and characterization of subgenomic replicons of New York strain of West Nile virus. Virology 296:219-33.
63. Pijlman G P. 2015. Enveloped virus-like particles as vaccines against pathogenic arboviruses. Biotechnol J 10:659-70.
64. Hayes E B. 2009. Zika virus outside Africa. Emerg Infect Dis 15:1347-50.
65. Yamshchikov V F, Compans R W. 1995. Formation of the flavivirus envelope: role of the viral NS2B-NS3 protease. J Virol 69:1995-2003.
66. Khromykh A A, Varnayski A N, Westaway E G. 1998. Encapsidation of the flavivirus kunjin replicon RNA by using a complementation system providing Kunjin virus structural proteins in trans. J Virol 72:5967-77.
67. Duenas-Carrera S, Alvarez-Lajonchere L, Alvarez-Obregon J C, Herrera A, Lorenzo L J, Pichardo D, Morales J. 2000. A truncated variant of the hepatitis C virus core induces a slow but potent immune response in mice following DNA immunization. Vaccine 19:992-7.
68. Xing Y P, Huang Z H, Wang S X, Cai J, Li J, Chou T H, Lu S. 2005. Novel DNA vaccine based on hepatitis B virus core gene induces specific immune responses in Balb/c mice. World J Gastroenterol 11:4583-6.
69. Aihara H, Takasaki T, Matsutani T, Suzuki R, Kurane I. 1998. Establishment and characterization of Japanese encephalitis virus-specific, human CD4(+) T-cell clones: flavivirus cross-reactivity, protein recognition, and cytotoxic activity. J Virol 72:8032-6.

What is claimed is:

1. A nucleic acid vector comprising:
   a recombinant nucleic acid comprising: a Zika virus CprME gene of SEQ ID NO: 3 or a recombinant nucleic acid encoding a prME gene region of Zika virus of SEQ ID NO: 3, operably linked to a promoter.

2. The vector of claim 1, wherein the nucleic acid vector is selected from a flavivirus vector, a plasmid, or a lentiviral vector.

3. The vector of claim 1, wherein the CprME, the prME gene, or both, are codon optimized for expression in human cells.

4. The vector of claim 1, wherein at least one of: the nucleic acid vector comprises a Cytomegalovirus (CMV) enhancer-promoter, multiple cloning site, Bovine Growth Hormone (BGH) polyadenylation signal and transcription termination sequence, SV40 origin, ampicillin resistance gene and pUC origin of replication, and the CprME gene, the prME gene, or both, are codon optimized for expression in human cells; or the vector further comprises at least one of an NS2B3 protease gene, or a selectable marker.

5. The vector of claim 1, wherein the vector is a lentiviral expression vector comprising a directional Cloning site, Rouse Sarcoma Virus (RSV) enhance/promoter, Modified HIV-1 5' and 3' Long Terminal Repeats (LTR), HIV-1 psi (ψ), HIV Rev response element (RRE), (CMV) immediate early promoter, C-terminal V5 epitope, Blasticidin (bsd) resistance gene, Ampicillin resistance gene, and pUC origin of replication.

6. A method of making Zika virus Reporter Virus Particles (RVP) comprising:
   transfecting cells to stably express a Zika CprME gene of SEQ ID NO:3; and
   transfecting the cells stably with a sub-genomic replicon derived from a lineage II strain of WNV or ZIKV that also expresses a reporter gene;
   incubating the cells under conditions in which the proteins are expressed for a period sufficient to form RVPs; and harvesting the RVPs.

7. The method of claim 6, wherein the cells are 293T cells, HeLa cells, MDCK cells, or Vero cells.

8. The method of claim 6, wherein the reporter gene is selected from at least one of green fluorescent protein; yellow fluorescent protein; blue fluorescent protein; Cerulean fluorescent protein; Cyan fluorescent protein; red fluorescent protein from Zooanthus sp.; red fluorescent protein from Entremacaea quadricolor (RFP), or flavin mononucleotide (FMN)-binding fluorescent proteins (FbFPs).

9. The method of claim 6, further comprising transfecting an NS2B3 protease gene into the cell, wherein the CprME is codon optimized, or wherein the vector further comprises a selectable marker and selecting stable expression with a selectable marker.

10. A cell line comprising: a codon optimized CprME gene of SEQ ID NO:3 of Zika virus that is stably expressed.

11. The cell line of claim 10, wherein the cell line is selected from at least one of: 293T cells, HeLa cells, MDCK cells, or Vero cells;
    the cell line is transduced with Lentiviral particles made in cells expressing lentiviral prME and pHP-dl-N/A, and VSVG Env;
    the cell line is stably transduced and selected using a selectable marker;
    the cell line is stably transduced and selected using a selectable marker for blasticidin selection; or
    the cell line is further transfected with an NS2B3 protease gene.

12. A cell line comprising: a codon optimized prME gene of SEQ ID NO:3 that is stably expressed.

13. The cell line of claim 12, wherein the cell line is 293T cells, HeLa cells, MDCK cells, or Vero cells.

14. A method of making stably transduced cell lines comprising:
    transfecting cells with a lentiviral vector expressing ZIKV prME, CprME of SEQ ID NO:4, or CprME of SEQ ID NO:3, and pHP-dl-N/A and VSVG Env to produce Lentiviral particles;
    transducing cells with the Lentiviral particles; and
    selecting stable transduced cells with a selection agent to create the stably transduced cell lines.

15. The method of claim 14, wherein the cell line is 293T cells, HeLa cells, MDCK cells, or Vero cells, or wherein the ZIKV prME, CprME of SEQ ID NO:3, or both prME and CprME of SEQ ID NO:3 are codon optimized.

16. A method of making Zika virus Virus Like Particles (VLPs) comprising:
    transfecting cells to stably express a Zika CprME gene of SEQ ID NO:3; and
    transfecting the cells stably with a sub-genomic replicon derived from a lineage II strain of WNV or ZIKV;
    incubating the cells under conditions in which the proteins are expressed for a period sufficient to form VLPs; and
    harvesting the VLPs.

17. The method of claim 14, wherein at least one of: the Zika CprME gene; or the VLP is made in a cell line that expresses an NS2B3 protease.

* * * * *

SEQUENCE LISTING

<160> NUMBER OF SEQ ID NOS: 4

<210> SEQ ID NO 1
<211> LENGTH: 10374
<212> TYPE: DNA
<213> ORGANISM: Artificial Sequence
<220> FEATURE:
<223> OTHER INFORMATION: Synthetic primer

<400> SEQUENCE: 1

```
acaggtttta ttttggattt ggaaacgaga gtttctggtc atgaaaaacc caaaaaagaa      60
atccggagga ttccggattg tcaatatgct aaaacgcgga gtagcccgtg tgagcccctt     120
tgggggcttg aagaggctgc cagccggact tctgctgggt catgggccca tcaggatggt     180
cttggcgatt ctagccttt tgagattcac ggcaatcaag ccatcactgg gtctcatcaa      240
tagatgggt tcagtgggga aaaagaggc tatggaaata ataaagaagt tcaagaaaga       300
tctggctgcc atgctgagaa taatcaatgc taggaaggag aagaagagac gaggcgcaga    360
tactagtgtc ggaattgttg gcctcctgct gaccacagct atggcagcgg aggtcactag    420
acgtgggagt gcatactata tgtacttgga cagaaacgat gctggggagg ccatatcttt    480
tccaaccaca ttggggatga ataagtgtta tatacagatc atggatcttg acacacgtg     540
tgatgccacc atgagctatg aatgccctat gctggatgag ggggtggaac cagatgacgt    600
cgattgttgg tgcaacacga cgtcaacttg ggttgtgtac ggaacctgcc atcacaaaaa    660
aggtgaagca cggagatcta aagagctgtg tgacgctccc tcccattcca ctaggaagct    720
gcaaacgcgg tcgcaaacct ggttggaatc aagagaataa acaaagcact tgattagagt    780
cgaaaattgg atattcagga accctggctt cgcgttagca gcagctgcca tcgcttggct    840
tttgggaagc tcaacgagcc aaaaagtcat atacttggtc atgatactgc tgattgcccc    900
ggcatacagc atcaggtgca taggagtcag caatagggac tttgtggaag gtatgtcagg    960
tgggacttgg gttgatgttg tcttggaaca tggaggttgt gtcactgtaa tggcacagga   1020
caaaccgact gtcgacatag agctggttac aacaacagtc agcaacatgg cggaggtaag   1080
atcctactgc tatgaggcat caatatcaga catggcttcg gacagccgct gcccaacaca   1140
aggtgaagcc taccttgaca agcaatcaga cactcaatat gtctgcaaaa gaacgttagt    1200
ggacagaggc tggggaaatg gatgtggact ttttggcaaa gggagcctgg tgacatgcgc    1260
taagtttgca tgctccaaga aaatgaccgg gaagagcatc cagccagaga atctggagta    1320
ccggataatg ctgtcagttc atggctccca gcacagtggg atgatcgtta atgacacagg    1380
acatgaaact gatgagaata gagcgaaagt tgagataacg cccaattcac caagagccga    1440
agccaccctg gggggtttg gaagcctagg acttgattgt gaaccgagga caggccttga    1500
cttttcagat ttgtattact tgactatgaa taacaagcac tggctggttc acaaggagtg    1560
gttccacgac attccattac cttggcacgc tggggcagac accggaactc cacactggaa   1620
caacaaagaa gcactggtag agttcaagga cgcacatgcc aaaaggcaaa ctgtcgtggt    1680
tctagggagt caagaaggag cagttcacac ggcccttgct ggagctctgg aggctgagat    1740
ggatggtgca aagggaaggc tgtcctctgg ccacttgaaa tgtcgcctga aaatggataa    1800
acttagattg aagggcgtgt catactcctt gtgtactgca gcgttcacat tcaccaagat   1860
cccggctgaa acactgcacg ggacagtcac agtggaggta cagtacgcag ggacagatgg   1920
accttgcaag gttccagctc agatggcggt ggacatgcaa actctgaccc cagttgggag   1980
gttgataacc gctaaccccg taatcactga aagcactgag aactctaaga tgatgctgga   2040
acttgatcca ccatttgggg actcttacat tgtcatagga gtcggggaga agaagatcac   2100
ccaccactgg cacaggagtg gcagcaccat tggaaaagca tttgaagcca ctgtgagagg   2160
tgccaagaga atggcagtct gggagacac agcctgggac tttggatcag ttggaggcgc    2220
tctcaactca ttgggcaagg gcatccatca aatctttgga gcagctttca atcattgtt    2280
tggaggaatg tcctgttct cacaaattct cattggaacg ttgctgatgt ggttgggtct    2340
gaacgcaaag aatggatcta tttccccttat gtgcttggcc ttagggggag tgttgatctt   2400
```

```
cttatccaca gccgtctctg ctgatgtggg gtgctcggtg gacttctcaa agaaggagac    2460
gagatgcggt acagggtgt tcgtctataa cgacgttgaa gcctggaggg acaggtacaa     2520
gtaccatcct gactcccccc gtagattggc agcagcagtc aagcaagcct gggaagatgg    2580
tatctgcggg atctcctctg tttcaagaat ggaaaacatc atgtggagat cagtagaagg    2640
ggagctcaac gcaatcctgg aagagaatgg agttcaactg acggtcgttg tgggatctgt    2700
aaaaaacccc atgtggagag gtccacagag attgcccgtg cctgtgaacg agctgcccca    2760
cggctggaag gcttggggga atcgtactt cgtcagagca gcaaagacaa ataacagctt     2820
tgtcgtggat ggtgacacac tgaaggaatg cccactcaaa catagagcat ggaacagctt    2880
tcttgtggag gatcatgggt tcggggtatt tcacactagt gtctggctca aggttagaga    2940
agattattca ttagagtgtg atccagccgt tattggaaca gctgttaagg gaaaggaggc    3000
tgtacacagt gatctaggct actggattga gagtgagaag aatgacacat ggaggctgaa    3060
gagggcccat ctgatcgaga tgaaaacatg tgaatggcca aagtcccaca cattgtggac    3120
agatggaata aagagagtg atctgatcat acccaagtct ttagctgggc cactcagcca    3180
tcacaatacc agagagggct acaggaccca aatgaaaggg ccatggcaca gtgaagagct    3240
tgaaattcgg tttgaggaat gcccaggcac taaggtccac gtggaggaaa catgtggaac    3300
gagaggacca tctctgagat caaccactgc aagcggaagg gtgatcgagg aatggtgctg    3360
cagggagtgc acaatgcccc cactgtcgtt ccgggctaaa gatggctgtt ggtatggaat    3420
ggagataagg cccaggaaag aaccagaaag caacttagta aggtcaatgg tgactgcagg    3480
atcaactgat cacatggacc acttctccct tggagtgctt gtgattctgc tcatggtgca    3540
ggaagggttg aagaagagaa tgaccacaaa gatcatcata agcacatcaa tggcagtgct    3600
ggtagctatg atcctgggag gattttcaat gagtgacctg gctaagcttg caattttgat    3660
gggtgccacc ttcgcggaaa tgaacactgg aggagatgta gctcatctgg cgctgatagc    3720
ggcattcaaa gtcagaccag cgttgctggt atctttcatc ttcagagcta attggacacc    3780
ccgtgaaagc atgctgctgg ccttggcctc gtgtcttttg caaactgcga tctccgcctt    3840
ggaaggcgac ctgatggttc tcatcaatgg ttttgctttg gcctggttgg caatacgagc    3900
gatggttgtt ccacgcactg ataacatcac cttggcaatc ctggctgctc tgacaccact    3960
ggcccggggc acactgcttg tggcgtggag agcaggcctt gctacttgcg gggggtttat    4020
gctcctctct ctgaagggaa aaggcagtgt gaagaagaac ttaccatttg tcatggccct    4080
gggactaacc gctgtgaggc tggtcgaccc catcaacgtg gtgggactgc tgttgctcac    4140
aaggagtggg aagcggagct ggcccccctag cgaagtactc acagctgttg gcctgatatg    4200
cgcattggct ggagggttcg ccaaggcaga tatagagatg gctgggccca tggccgcggt    4260
cggtctgcta attgtcagtt acgtggtctc aggaaagagt gtggacatgt acattgaaag    4320
agcaggtgac atcacatggg aaaaagatgc ggaagtcact ggaaacagtc ccggctcga    4380 tgtggcgcta gatgagagtg gtgatttctc cctggtggag gatgacggtc cccccatgag    4440
agagatcata ctcaaggtgg tcctgatgac catctgtggc atgaacccaa tagccatacc    4500
ctttgcagct ggagcgtggt acgtatacgt gaagactgga aaaaggagtg gtgctctatg    4560
ggatgtgcct gctcccaagg aagtaaaaaa ggggagagacc acagatggag tgtacagagt    4620
aatgactcgt agactgctag gttcaacaca agttggagtg ggagttatgc aagaggggt     4680 cttcacact atgtggcacg tcacaaaagg atccgcgctg agaagcggtg aagggagact     4740
```

```
tgatccatac tggggagatg tcaagcagga tctggtgtca tactgtggtc catggaagct    4800
agatgccgcc tgggacgggc acagcgaggt gcagctcttg gccgtgcccc cggagagag     4860 agcgaggaac atccagactc tgcccggaat atttaagaca aaggatgggg acattggagc    4920
ggttgcgctg gattacccag caggaacttc aggatctcct atcctagaca agtgtggag     4980 agtgatagga ctttatggca atggggtcgt gatcaaaaat gggagttatg ttagtgccat    5040
cacccaaggg aggagggagg aagagactcc tgttgagtgc ttcgagcctt cgatgctgaa    5100
gaagaagcag ctaactgtct tagacttgca tcctggagct gggaaaacca ggagagttct    5160
tcctgaaata gtccgtgaag ccataaaaac aagactccgt actgtgatct tagctccaac    5220
cagggttgtc gctgctgaaa tggaggaggc ccttagaggg cttccagtgc gttatatgac    5280
aacagcagtc aatgtcaccc actctggaac agaaatcgtc gacttaatgt gccatgccac    5340
cttcacttcg cgtctactac agccaatcag agtccccaac tataatctgt atattatgga    5400
tgaggcccac ttcacagatc cctcaagtat agcagcaaga ggatacattt caacaagggt    5460
tgagatgggg gaggcggccg ccatcttcat gaccgccacg ccaccaggaa cccgtgacgc    5520
atttccggac tccaactcac caattatgga caccgaagtg gaagtcccag agagagcctg    5580
gagctcaggc tttgattggg tgacggatca ttctggaaaa acagtttggt ttgttccaag    5640
cgtgaggaac ggcaatgaga tcgcagcttg tctgacaaag gctggaaaac gggtcataca    5700
gctcagcaga aagactttg agacagagtt ccagaaaaca aaacatcaag agtgggactt     5760
tgtcgtgaca actgacattt cagagatggg cgccaacttt aaagctgacc gtgtcataga    5820
ttccaggaga tgcctaaagc cggtcatact tgatggcgag agagtcattc tggctggacc    5880
catgcctgtc acacatgcca gcgctgccca gaggaggggg cgcataggca ggaatcccaa    5940
caaacctgga gatgagtatc tgtatggagg tgggtgcgca gagactgacg aagaccatgc    6000
acactggctt gaagcaagaa tgctccttga caatatttac ctccaagatg gcctcatagc    6060
ctcgctctat cgacctgagg ccgacaaagt agcagccatt gagggagagt tcaagcttag    6120
gacggagcaa aggaagacct tgtggaact catgaaaaga ggagatcttc ctgtttggct      6180
ggcctatcag gttgcatctg ccggaataac ctacacagat agaagatggt gctttgatgg    6240
cacgaccaac aacaccataa tggaagacag tgtgccggca gaagtgtgga ccagacacgg    6300
agagaaaaga gtgctcaaac cgaggtggat ggacgccaga gtttgttcag atcatgcggc    6360
cctgaagtca ttcaaggagt ttgccgctgg gaaaagagga gcggcttttg gagtgatgga    6420
agccctggga acactgccag acacatgac agagagattc caggaagcca ttgacaacct     6480
cgctgtgctc atgcgggcag agactggaag caggccttac aaaagccgcg gcgcccaatt    6540
gccggagacc ctagagacca ttatgctttt ggggttgctg ggaacagtct cgctgggaat    6600
cttcttcgtc ttgatgagga caagggcat agggaagatg gctttggaa tggtgactct       6660 tggggccagc gcatggctca tgtggctctc ggaaattgag ccagcagaa ttgcatgtgt      6720 cctcattgtt gtgttcctat tgctggtggt gctcataccct gagccagaaa agcaaagatc   6780
tccccaggac aaccaaatgg caatcatcat catggtagca gtaggtcttc tgggcttgat    6840
taccgccaat gaactcggat ggttggagag aacaaagagt gacctaagcc atctaatggg    6900
aaggagagag aggggggcaa ccataggatt ctcaatggac attgacctgc ggccagcctc    6960
agcttgggcc atctatgctg ccttgacaac tttcattacc ccagccgtcc aacatgcagt    7020 gaccaccctca tacaacaact actccttaat ggcgatggcc acgcaagctg gagtgttgtt    7080
tggtatgggc aaagggatgc cattctacgc atgggacttt ggagtccgc tgctaatgat     7140
```

```
aggttgctac tcacaattaa cacccctgac cctaatagtg gccatcattt tgctcgtggc    7200
gcactacatg tacttgatcc cagggctgca ggcagcagct gcgcgtgctg cccagaagag    7260
aacggcagct ggcatcatga agaaccctgt tgtggatgga atagtggtga ctgacattga    7320
cacaatgaca attgaccccc aagtggagaa aaagatggga caggtgctac tcatagcagt    7380
agccgtctcc agcgccatac tgtcgcggac cgcctggggg tgggggagg ctggggccct     7440 gatcacagcc gcaacttcca ctttgtggga aggctctccg aacaagtact ggaactcctc    7500
tacagccact tcactgtgta acatttttag gggaagttac ttggctggag cttctctaat    7560
ctacacagta acaagaaacg ctggcttggt caagagacgt gggggtggaa caggagagac    7620
cctgggagag aaatggaagg cccgcttgaa ccagatgtcg gccctggagt tctactccta    7680
caaaaagtca ggcatcaccg aggtgtgcag agaagaggcc cgccgcgccc tcaaggacgg    7740
tgtggcaacg ggaggccatg ctgtgtcccg aggaagtgca aagctgagat ggttggtgga    7800
gcggggatac ctgcagccct atggaaaggt cattgatctt ggatgtggca gaggggctg     7860 gagttactac gccgccacca tccgcaaagt tcaagaagtg aaaggataca caaaggagg     7920 ccctggtcat gaagaacccg tgttggtgca aagctatggg tggaacatag tccgtcttaa    7980 gagtgggtg gacgtctttc atatggcggc tgagccgtgt gacacgttgc tgtgtgacat     8040
aggtgagtca tcatctagtc ctgaagtgga agaagcacgg acgctcagag tcctctccat    8100
ggtgggggat tggcttgaaa aaagaccagg agccttttgt ataaaagtgt tgtgcccata    8160
caccagcact atgatggaaa ccctggagcg actgcagcgt aggtatgggg gaggactggt    8220
cagagtgcca ctctcccgca actctacaca tgagatgtac tgggtctctg gagcgaaaag    8280
caacaccata aaaagtgtgt ccaccacgag ccagctcctc ttggggcgca tggacgggcc    8340
taggaggcca gtgaaatatg aggaggatgt gaatctcggc tctggcacgc gggctgtggt    8400
aagctgcgct gaagctccca acatgaagat cattggtaac cgcattgaaa ggatccgcag    8460
tgagcacgcg gaaacgtggt tctttgacga gaaccaccca tataggacat gggcttacca    8520
tggaagctat gaggccccca cacaagggtc agcgtcctct ctaataaacg ggggttgtcag    8580 gctcctgtca aaaccctggg atgtggtgac tggagtcaca ggaatagcca tgaccgacac    8640
cacaccgtat ggtcagcaaa gagttttcaa ggaaaaagtg gacactaggg tgccagaccc    8700
ccaagaaggc actcgtcagg ttatgagcat ggtctcttcc tggttgtgga aagagctagg    8760
caaacacaaa cggccacgag tctgtaccaa agaagagttc atcaacaagg ttcgtagcaa    8820
tgcagcatta ggggcaatat ttgaagagga aaaagagtgg aagactgcag tggaagctgt    8880
gaacgatcca aggttctggg ctctagtgga caaggaaaga gagcaccacc tgagaggaga    8940
gtgccagagt tgtgtgtaca acatgatggg aaaaagagaa aagaaacaag ggaatttgg     9000 aaaggccaag ggcagccgcg ccatctggta tatgtggcta ggggctagat ttctagagtt    9060
cgaagccctt ggattcttga acgaggatca ctggatgggg agagaaact caggaggtgg    9120 tgttgaaggg ctgggattac aaagactcgg atatgtccta gaagagatga gtcgtatacc    9180
aggaggaagg atgtatgcag atgacactgc tggctgggac acccgcatta gcaggtttga    9240
tctggagaat gaagctctaa tcaccaacca atgagagaaa gggacaggg cttggcatt     9300 ggccataatc aagtacacat accaaaacaa agtggtaaag gtccttagac cagctgaaaa    9360
agggaaaaca gttatggaca ttatttcgag acaagaccaa aggggagcg acaagttgt     9420 cacttacgct cttaacacat ttaccaacct agtggtgcaa ctcattcgga atatggaggc    9480
```

```
tgaggaagtt ctagagatgc aagacttgtg gctgctgcgg aggtcagaga aagtgactaa      9540
ctggttgcag agcaacggat gggataggct caaacgaatg gcagtcagtg gagatgattg      9600
cgttgtgaag ccaattgatg ataggtttgc acatgccctc aggttcttga atgatatggg      9660
aaaagttagg aaggacacac aagagtggaa accctcaact ggatgggaca actgggaaga      9720
agttccgttt tgctcccacc acttcaacaa gctccatctc aaggacggga ggtccattgt      9780
ggttccctgc cgccaccaag atgaactgat tggccgggcc cgcgtctctc caggggcggg      9840
atggagcatc cgggagactg cttgcctagc aaaatcatat gcgcaaatgt ggcagctcct      9900
ttatttccac agaagggacc tccgactgat ggccaatgcc atttgttcat ctgtgccagt      9960
tgactgggtt ccaactggga gaactacctg gtcaatccat ggaaagggag aatggatgac     10020
cactgaagac atgcttgtgg tgtggaacag agtgtggatt gaggagaacg accacatgga     10080
agacaagacc ccagttacga aatggacaga cattccctat ttgggaaaaa gggaagactt     10140
gtggtgtgga tctctcatag ggcacagacc gcgcaccacc tgggctgaga acattaaaaa     10200
cacagtcaac atggtgcgca ggatcatagg tgatgaagaa aagtacatgg actacctatc     10260
cacccaagtt cgctacttgg gtgaagaagg gtctacacct ggagtgctgt aagcaccaat     10320
cttaatgttg tcaggcctgc tagtcagcca cagcttgggg aaagctgtgc agcc           10374

<210> SEQ ID NO 2
<211> LENGTH: 3423
<212> TYPE: PRT
<213> ORGANISM: Artificial Sequence
<220> FEATURE:
<223> OTHER INFORMATION: Synthetic peptide

<400> SEQUENCE: 2

Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Thr Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205
```

-continued

| | | | | | | | | | | | | | | |
|---|---|---|---|---|---|---|---|---|---|---|---|---|---|---|
|Glu|Ala|Arg|Arg|Ser|Arg|Arg|Ala|Val|Thr|Leu|Pro|Ser|His|Ser|Thr|
|210| | | | |215| | | | |220| | | | |

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
            245                 250                 255

Phe Ala Leu Ala Ala Ala Ile Ala Trp Leu Leu Gly Ser Ser Thr
                260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
                355                 360                 365

Glu Ala Tyr Leu Asp Lys Gln Ser Asp Thr Gln Tyr Val Cys Lys Arg
370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
            435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
            595                 600                 605

Ala Glu Thr Leu His Gly Thr Val Thr Val Glu Val Gln Tyr Ala Gly
610                 615                 620

Thr Asp Gly Pro Cys Lys Val Pro Ala Gln Met Ala Val Asp Met Gln

-continued

```
            625                 630                 635                 640
Thr Leu Thr Pro Val Gly Arg Leu Ile Thr Ala Asn Pro Val Ile Thr
                645                 650                 655
Glu Ser Thr Glu Asn Ser Lys Met Met Leu Glu Leu Asp Pro Pro Phe
                660                 665                 670
Gly Asp Ser Tyr Ile Val Ile Gly Val Gly Glu Lys Lys Ile Thr His
                675                 680                 685
His Trp His Arg Ser Gly Ser Thr Ile Gly Lys Ala Phe Glu Ala Thr
            690                 695                 700
Val Arg Gly Ala Lys Arg Met Ala Val Leu Gly Asp Thr Ala Trp Asp
705                 710                 715                 720
Phe Gly Ser Val Gly Gly Ala Leu Asn Ser Leu Gly Lys Gly Ile His
                725                 730                 735
Gln Ile Phe Gly Ala Ala Phe Lys Ser Leu Phe Gly Gly Met Ser Trp
                740                 745                 750
Phe Ser Gln Ile Leu Ile Gly Thr Leu Leu Met Trp Leu Gly Leu Asn
            755                 760                 765
Ala Lys Asn Gly Ser Ile Ser Leu Met Cys Leu Ala Leu Gly Gly Val
        770                 775                 780
Leu Ile Phe Leu Ser Thr Ala Val Ser Ala Asp Val Gly Cys Ser Val
785                 790                 795                 800
Asp Phe Ser Lys Lys Glu Thr Arg Cys Gly Thr Gly Val Phe Val Tyr
                805                 810                 815
Asn Asp Val Glu Ala Trp Arg Asp Arg Tyr Lys Tyr His Pro Asp Ser
                820                 825                 830
Pro Arg Arg Leu Ala Ala Ala Val Lys Gln Ala Trp Glu Asp Gly Ile
            835                 840                 845
Cys Gly Ile Ser Ser Val Ser Arg Met Glu Asn Ile Met Trp Arg Ser
        850                 855                 860
Val Glu Gly Glu Leu Asn Ala Ile Leu Glu Glu Asn Gly Val Gln Leu
865                 870                 875                 880
Thr Val Val Val Gly Ser Val Lys Asn Pro Met Trp Arg Gly Pro Gln
                885                 890                 895
Arg Leu Pro Val Pro Val Asn Glu Leu Pro His Gly Trp Lys Ala Trp
                900                 905                 910
Gly Lys Ser Tyr Phe Val Arg Ala Ala Lys Thr Asn Asn Ser Phe Val
            915                 920                 925
Val Asp Gly Asp Thr Leu Lys Glu Cys Pro Leu Lys His Arg Ala Trp
        930                 935                 940
Asn Ser Phe Leu Val Glu Asp His Gly Phe Gly Val Phe His Thr Ser
945                 950                 955                 960
Val Trp Leu Lys Val Arg Glu Asp Tyr Ser Leu Glu Cys Asp Pro Ala
                965                 970                 975
Val Ile Gly Thr Ala Val Lys Gly Lys Glu Ala Val His Ser Asp Leu
            980                 985                 990
Gly Tyr Trp Ile Glu Ser Glu Lys Asn Asp Thr Trp Arg Leu Lys Arg
            995                 1000                1005
Ala His Leu Ile Glu Met Lys Thr Cys Glu Trp Pro Lys Ser His
        1010                1015                1020
Thr Leu Trp Thr Asp Gly Ile Glu Glu Ser Asp Leu Ile Ile Pro
        1025                1030                1035
Lys Ser Leu Ala Gly Pro Leu Ser His His Asn Thr Arg Glu Gly
        1040                1045                1050
```

-continued

Tyr Arg Thr Gln Met Lys Gly Pro Trp His Ser Glu Glu Leu Glu
1055                     1060                1065

Ile Arg Phe Glu Glu Cys Pro Gly Thr Lys Val His Val Glu Glu
1070                     1075                1080

Thr Cys Gly Thr Arg Gly Pro Ser Leu Arg Ser Thr Thr Ala Ser
1085                     1090                1095

Gly Arg Val Ile Glu Glu Trp Cys Cys Arg Glu Cys Thr Met Pro
1100                     1105                1110

Pro Leu Ser Phe Arg Ala Lys Asp Gly Cys Trp Tyr Gly Met Glu
1115                     1120                1125

Ile Arg Pro Arg Lys Glu Pro Glu Ser Asn Leu Val Arg Ser Met
1130                     1135                1140

Val Thr Ala Gly Ser Thr Asp His Met Asp His Phe Ser Leu Gly
1145                     1150                1155

Val Leu Val Ile Leu Leu Met Val Gln Glu Gly Leu Lys Lys Arg
1160                     1165                1170

Met Thr Thr Lys Ile Ile Ile Ser Thr Ser Met Ala Val Leu Val
1175                     1180                1185

Ala Met Ile Leu Gly Gly Phe Ser Met Ser Asp Leu Ala Lys Leu
1190                     1195                1200

Ala Ile Leu Met Gly Ala Thr Phe Ala Glu Met Asn Thr Gly Gly
1205                     1210                1215

Asp Val Ala His Leu Ala Leu Ile Ala Ala Phe Lys Val Arg Pro
1220                     1225                1230

Ala Leu Leu Val Ser Phe Ile Phe Arg Ala Asn Trp Thr Pro Arg
1235                     1240                1245

Glu Ser Met Leu Leu Ala Leu Ala Ser Cys Leu Leu Gln Thr Ala
1250                     1255                1260

Ile Ser Ala Leu Glu Gly Asp Leu Met Val Leu Ile Asn Gly Phe
1265                     1270                1275

Ala Leu Ala Trp Leu Ala Ile Arg Ala Met Val Val Pro Arg Thr
1280                     1285                1290

Asp Asn Ile Thr Leu Ala Ile Leu Ala Ala Leu Thr Pro Leu Ala
1295                     1300                1305

Arg Gly Thr Leu Leu Val Ala Trp Arg Ala Gly Leu Ala Thr Cys
1310                     1315                1320

Gly Gly Phe Met Leu Leu Ser Leu Lys Gly Lys Gly Ser Val Lys
1325                     1330                1335

Lys Asn Leu Pro Phe Val Met Ala Leu Gly Leu Thr Ala Val Arg
1340                     1345                1350

Leu Val Asp Pro Ile Asn Val Val Gly Leu Leu Leu Leu Thr Arg
1355                     1360                1365

Ser Gly Lys Arg Ser Trp Pro Pro Ser Glu Val Leu Thr Ala Val
1370                     1375                1380

Gly Leu Ile Cys Ala Leu Ala Gly Gly Phe Ala Lys Ala Asp Ile
1385                     1390                1395

Glu Met Ala Gly Pro Met Ala Ala Val Gly Leu Leu Ile Val Ser
1400                     1405                1410

Tyr Val Val Ser Gly Lys Ser Val Asp Met Tyr Ile Glu Arg Ala
1415                     1420                1425

Gly Asp Ile Thr Trp Glu Lys Asp Ala Glu Val Thr Gly Asn Ser
1430                     1435                1440

-continued

Pro Arg Leu Asp Val Ala Leu Asp Glu Ser Gly Asp Phe Ser Leu
1445                1450                    1455

Val Glu Asp Asp Gly Pro Pro Met Arg Glu Ile Ile Leu Lys Val
1460                1465                    1470

Val Leu Met Thr Ile Cys Gly Met Asn Pro Ile Ala Ile Pro Phe
1475                1480                    1485

Ala Ala Gly Ala Trp Tyr Val Tyr Val Lys Thr Gly Lys Arg Ser
1490                1495                    1500

Gly Ala Leu Trp Asp Val Pro Ala Pro Lys Glu Val Lys Lys Gly
1505                1510                    1515

Glu Thr Thr Asp Gly Val Tyr Arg Val Met Thr Arg Arg Leu Leu
1520                1525                    1530

Gly Ser Thr Gln Val Gly Val Gly Val Met Gln Glu Gly Val Phe
1535                1540                    1545

His Thr Met Trp His Val Thr Lys Gly Ser Ala Leu Arg Ser Gly
1550                1555                    1560

Glu Gly Arg Leu Asp Pro Tyr Trp Gly Asp Val Lys Gln Asp Leu
1565                1570                    1575

Val Ser Tyr Cys Gly Pro Trp Lys Leu Asp Ala Ala Trp Asp Gly
1580                1585                    1590

His Ser Glu Val Gln Leu Leu Ala Val Pro Pro Gly Glu Arg Ala
1595                1600                    1605

Arg Asn Ile Gln Thr Leu Pro Gly Ile Phe Lys Thr Lys Asp Gly
1610                1615                    1620

Asp Ile Gly Ala Val Ala Leu Asp Tyr Pro Ala Gly Thr Ser Gly
1625                1630                    1635

Ser Pro Ile Leu Asp Lys Cys Gly Arg Val Ile Gly Leu Tyr Gly
1640                1645                    1650

Asn Gly Val Val Ile Lys Asn Gly Ser Tyr Val Ser Ala Ile Thr
1655                1660                    1665

Gln Gly Arg Arg Glu Glu Thr Pro Val Glu Cys Phe Glu Pro
1670                1675                    1680

Ser Met Leu Lys Lys Lys Gln Leu Thr Val Leu Asp Leu His Pro
1685                1690                    1695

Gly Ala Gly Lys Thr Arg Arg Val Leu Pro Glu Ile Val Arg Glu
1700                1705                    1710

Ala Ile Lys Thr Arg Leu Arg Thr Val Ile Leu Ala Pro Thr Arg
1715                1720                    1725

Val Val Ala Ala Glu Met Glu Glu Ala Leu Arg Gly Leu Pro Val
1730                1735                    1740

Arg Tyr Met Thr Thr Ala Val Asn Val Thr His Ser Gly Thr Glu
1745                1750                    1755

Ile Val Asp Leu Met Cys His Ala Thr Phe Thr Ser Arg Leu Leu
1760                1765                    1770

Gln Pro Ile Arg Val Pro Asn Tyr Asn Leu Tyr Ile Met Asp Glu
1775                1780                    1785

Ala His Phe Thr Asp Pro Ser Ser Ile Ala Ala Arg Gly Tyr Ile
1790                1795                    1800

Ser Thr Arg Val Glu Met Gly Glu Ala Ala Ile Phe Met Thr
1805                1810                    1815

Ala Thr Pro Pro Gly Thr Arg Asp Ala Phe Pro Asp Ser Asn Ser
1820                1825                    1830

Pro Ile Met Asp Thr Glu Val Glu Val Pro Glu Arg Ala Trp Ser

-continued

```
            1835                1840                1845

Ser Gly Phe Asp Trp Val Thr Asp His Ser Gly Lys Thr Val Trp
    1850                1855                1860

Phe Val Pro Ser Val Arg Asn Gly Asn Glu Ile Ala Ala Cys Leu
    1865                1870                1875

Thr Lys Ala Gly Lys Arg Val Ile Gln Leu Ser Arg Lys Thr Phe
    1880                1885                1890

Glu Thr Glu Phe Gln Lys Thr Lys His Gln Glu Trp Asp Phe Val
    1895                1900                1905

Val Thr Thr Asp Ile Ser Glu Met Gly Ala Asn Phe Lys Ala Asp
    1910                1915                1920

Arg Val Ile Asp Ser Arg Arg Cys Leu Lys Pro Val Ile Leu Asp
    1925                1930                1935

Gly Glu Arg Val Ile Leu Ala Gly Pro Met Pro Val Thr His Ala
    1940                1945                1950

Ser Ala Ala Gln Arg Arg Gly Arg Ile Gly Arg Asn Pro Asn Lys
    1955                1960                1965

Pro Gly Asp Glu Tyr Leu Tyr Gly Gly Gly Cys Ala Glu Thr Asp
    1970                1975                1980

Glu Asp His Ala His Trp Leu Glu Ala Arg Met Leu Leu Asp Asn
    1985                1990                1995

Ile Tyr Leu Gln Asp Gly Leu Ile Ala Ser Leu Tyr Arg Pro Glu
    2000                2005                2010

Ala Asp Lys Val Ala Ala Ile Glu Gly Glu Phe Lys Leu Arg Thr
    2015                2020                2025

Glu Gln Arg Lys Thr Phe Val Glu Leu Met Lys Arg Gly Asp Leu
    2030                2035                2040

Pro Val Trp Leu Ala Tyr Gln Val Ala Ser Ala Gly Ile Thr Tyr
    2045                2050                2055

Thr Asp Arg Arg Trp Cys Phe Asp Gly Thr Thr Asn Asn Thr Ile
    2060                2065                2070

Met Glu Asp Ser Val Pro Ala Glu Val Trp Thr Arg His Gly Glu
    2075                2080                2085

Lys Arg Val Leu Lys Pro Arg Trp Met Asp Ala Arg Val Cys Ser
    2090                2095                2100

Asp His Ala Ala Leu Lys Ser Phe Lys Glu Phe Ala Ala Gly Lys
    2105                2110                2115

Arg Gly Ala Ala Phe Gly Val Met Glu Ala Leu Gly Thr Leu Pro
    2120                2125                2130

Gly His Met Thr Glu Arg Phe Gln Glu Ala Ile Asp Asn Leu Ala
    2135                2140                2145

Val Leu Met Arg Ala Glu Thr Gly Ser Arg Pro Tyr Lys Ala Ala
    2150                2155                2160

Ala Ala Gln Leu Pro Glu Thr Leu Glu Thr Ile Met Leu Leu Gly
    2165                2170                2175

Leu Leu Gly Thr Val Ser Leu Gly Ile Phe Phe Val Leu Met Arg
    2180                2185                2190

Asn Lys Gly Ile Gly Lys Met Gly Phe Gly Met Val Thr Leu Gly
    2195                2200                2205

Ala Ser Ala Trp Leu Met Trp Leu Ser Glu Ile Glu Pro Ala Arg
    2210                2215                2220

Ile Ala Cys Val Leu Ile Val Val Phe Leu Leu Leu Val Val Leu
    2225                2230                2235
```

```
Ile Pro Glu Pro Glu Lys Gln Arg Ser Pro Gln Asp Asn Gln Met
2240                2245                2250

Ala Ile Ile Ile Met Val Ala Val Gly Leu Leu Gly Leu Ile Thr
2255                2260                2265

Ala Asn Glu Leu Gly Trp Leu Glu Arg Thr Lys Ser Asp Leu Ser
2270                2275                2280

His Leu Met Gly Arg Arg Glu Glu Gly Ala Thr Ile Gly Phe Ser
2285                2290                2295

Met Asp Ile Asp Leu Arg Pro Ala Ser Ala Trp Ala Ile Tyr Ala
2300                2305                2310

Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
2375                2380                2385

Tyr Met Tyr Leu Ile Pro Gly Leu Gln Ala Ala Ala Ala Arg Ala
2390                2395                2400

Ala Gln Lys Arg Thr Ala Ala Gly Ile Met Lys Asn Pro Val Val
2405                2410                2415

Asp Gly Ile Val Val Thr Asp Ile Asp Thr Met Thr Ile Asp Pro
2420                2425                2430

Gln Val Glu Lys Lys Met Gly Gln Val Leu Leu Ile Ala Val Ala
2435                2440                2445

Val Ser Ser Ala Ile Leu Ser Arg Thr Ala Trp Gly Trp Gly Glu
2450                2455                2460

Ala Gly Ala Leu Ile Thr Ala Ala Thr Ser Thr Leu Trp Glu Gly
2465                2470                2475

Ser Pro Asn Lys Tyr Trp Asn Ser Ser Thr Ala Thr Ser Leu Cys
2480                2485                2490

Asn Ile Phe Arg Gly Ser Tyr Leu Ala Gly Ala Ser Leu Ile Tyr
2495                2500                2505

Thr Val Thr Arg Asn Ala Gly Leu Val Lys Arg Arg Gly Gly Gly
2510                2515                2520

Thr Gly Glu Thr Leu Gly Glu Lys Trp Lys Ala Arg Leu Asn Gln
2525                2530                2535

Met Ser Ala Leu Glu Phe Tyr Ser Tyr Lys Lys Ser Gly Ile Thr
2540                2545                2550

Glu Val Cys Arg Glu Glu Ala Arg Arg Ala Leu Lys Asp Gly Val
2555                2560                2565

Ala Thr Gly Gly His Ala Val Ser Arg Gly Ser Ala Lys Leu Arg
2570                2575                2580

Trp Leu Val Glu Arg Gly Tyr Leu Gln Pro Tyr Gly Lys Val Ile
2585                2590                2595

Asp Leu Gly Cys Gly Arg Gly Gly Trp Ser Tyr Tyr Ala Ala Thr
2600                2605                2610

Ile Arg Lys Val Gln Glu Val Lys Gly Tyr Thr Lys Gly Gly Pro
2615                2620                2625
```

| | | | | | | | | | | | |
|---|---|---|---|---|---|---|---|---|---|---|---|
|Gly|His|Glu|Glu|Pro|Val|Leu|Val|Gln|Ser|Tyr|Gly|Trp|Asn|Ile|
| |2630| | | |2635| | | |2640| | | | | |

Gly His Glu Glu Pro Val Leu Val Gln Ser Tyr Gly Trp Asn Ile
    2630                2635                2640

Val Arg Leu Lys Ser Gly Val Asp Val Phe His Met Ala Ala Glu
    2645                2650                2655

Pro Cys Asp Thr Leu Leu Cys Asp Ile Gly Glu Ser Ser Ser Ser
    2660                2665                2670

Pro Glu Val Glu Glu Ala Arg Thr Leu Arg Val Leu Ser Met Val
    2675                2680                2685

Gly Asp Trp Leu Glu Lys Arg Pro Gly Ala Phe Cys Ile Lys Val
    2690                2695                2700

Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asn
    2765                2770                2775

Leu Gly Ser Gly Thr Arg Ala Val Val Ser Cys Ala Glu Ala Pro
    2780                2785                2790

Asn Met Lys Ile Ile Gly Asn Arg Ile Glu Arg Ile Arg Ser Glu
    2795                2800                2805

His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
    2855                2860                2865

Pro Tyr Gly Gln Gln Arg Val Phe Lys Glu Lys Val Asp Thr Arg
    2870                2875                2880

Val Pro Asp Pro Gln Glu Gly Thr Arg Gln Val Met Ser Met Val
    2885                2890                2895

Ser Ser Trp Leu Trp Lys Glu Leu Gly Lys His Lys Arg Pro Arg
    2900                2905                2910

Val Cys Thr Lys Glu Glu Phe Ile Asn Lys Val Arg Ser Asn Ala
    2915                2920                2925

Ala Leu Gly Ala Ile Phe Glu Glu Glu Lys Glu Trp Lys Thr Ala
    2930                2935                2940

Val Glu Ala Val Asn Asp Pro Arg Phe Trp Ala Leu Val Asp Lys
    2945                2950                2955

Glu Arg Glu His His Leu Arg Gly Glu Cys Gln Ser Cys Val Tyr
    2960                2965                2970

Asn Met Met Gly Lys Arg Glu Lys Lys Gln Gly Glu Phe Gly Lys
    2975                2980                2985

Ala Lys Gly Ser Arg Ala Ile Trp Tyr Met Trp Leu Gly Ala Arg
    2990                2995                3000

Phe Leu Glu Phe Glu Ala Leu Gly Phe Leu Asn Glu Asp His Trp
    3005                3010                3015

Met Gly Arg Glu Asn Ser Gly Gly Gly Val Glu Gly Leu Gly Leu

```
                3020                3025                3030

Gln Arg Leu Gly Tyr Val Leu Glu Glu Met Ser Arg Ile Pro Gly
        3035                3040                3045

Gly Arg Met Tyr Ala Asp Asp Thr Ala Gly Trp Asp Thr Arg Ile
        3050                3055                3060

Ser Arg Phe Asp Leu Glu Asn Glu Ala Leu Ile Thr Asn Gln Met
        3065                3070                3075

Glu Lys Gly His Arg Ala Leu Ala Leu Ala Ile Ile Lys Tyr Thr
        3080                3085                3090

Tyr Gln Asn Lys Val Val Lys Val Leu Arg Pro Ala Glu Lys Gly
        3095                3100                3105

Lys Thr Val Met Asp Ile Ile Ser Arg Gln Asp Gln Arg Gly Ser
        3110                3115                3120

Gly Gln Val Val Thr Tyr Ala Leu Asn Thr Phe Thr Asn Leu Val
        3125                3130                3135

Val Gln Leu Ile Arg Asn Met Glu Ala Glu Glu Val Leu Glu Met
        3140                3145                3150

Gln Asp Leu Trp Leu Leu Arg Arg Ser Glu Lys Val Thr Asn Trp
        3155                3160                3165

Leu Gln Ser Asn Gly Trp Asp Arg Leu Lys Arg Met Ala Val Ser
        3170                3175                3180

Gly Asp Asp Cys Val Val Lys Pro Ile Asp Asp Arg Phe Ala His
        3185                3190                3195

Ala Leu Arg Phe Leu Asn Asp Met Gly Lys Val Arg Lys Asp Thr
        3200                3205                3210

Gln Glu Trp Lys Pro Ser Thr Gly Trp Asp Asn Trp Glu Glu Val
        3215                3220                3225

Pro Phe Cys Ser His His Phe Asn Lys Leu His Leu Lys Asp Gly
        3230                3235                3240

Arg Ser Ile Val Val Pro Cys Arg His Gln Asp Glu Leu Ile Gly
        3245                3250                3255

Arg Ala Arg Val Ser Pro Gly Ala Gly Trp Ser Ile Arg Glu Thr
        3260                3265                3270

Ala Cys Leu Ala Lys Ser Tyr Ala Gln Met Trp Gln Leu Leu Tyr
        3275                3280                3285

Phe His Arg Arg Asp Leu Arg Leu Met Ala Asn Ala Ile Cys Ser
        3290                3295                3300

Ser Val Pro Val Asp Trp Val Pro Thr Gly Arg Thr Thr Trp Ser
        3305                3310                3315

Ile His Gly Lys Gly Glu Trp Met Thr Thr Glu Asp Met Leu Val
        3320                3325                3330

Val Trp Asn Arg Val Trp Ile Glu Glu Asn Asp His Met Glu Asp
        3335                3340                3345

Lys Thr Pro Val Thr Lys Trp Thr Asp Ile Pro Tyr Leu Gly Lys
        3350                3355                3360

Arg Glu Asp Leu Trp Cys Gly Ser Leu Ile Gly His Arg Pro Arg
        3365                3370                3375

Thr Thr Trp Ala Glu Asn Ile Lys Asn Thr Val Asn Met Val Arg
        3380                3385                3390

Arg Ile Ile Gly Asp Glu Glu Lys Tyr Met Asp Tyr Leu Ser Thr
        3395                3400                3405

Gln Val Arg Tyr Leu Gly Glu Glu Gly Ser Thr Pro Gly Val Leu
        3410                3415                3420
```

<210> SEQ ID NO 3
<211> LENGTH: 2391
<212> TYPE: DNA
<213> ORGANISM: Artificial Sequence
<220> FEATURE:
<223> OTHER INFORMATION: Synthetic primer

<400> SEQUENCE: 3

| | | | | | |
|---|---|---|---|---|---|
| atgaagaatc | ccaagaagaa | atctggcggg | ttccgaatcg | tcaatatgct | gaagagagga | 60 |
| gtggcaagag | tgtcacccttt | tggcgggctg | aagaggctgc | ctgcaggact | gctgctgggg | 120 |
| cacgaccaa | tcaggatggt | gctggcaatt | ctggccttcc | tgcgctttac | cgctatcaaa | 180 |
| cccagcctgg | gcctgattaa | tcgctggggg | tccgtgggaa | agaaagaggc | tatggagatc | 240 |
| atcaagaagt | tcaagaaaga | cctggccgct | atgctgcgga | tcattaacgc | tagaaaggag | 300 |
| aagaaacgga | gagggcaga | tacctctgtg | gcatcgtcg | ggctgctgct | gaccacagca | 360 |
| atggcagccg | aggtgacaag | gcgcggatca | gcctactata | tgtacctgga | ccggaatgat | 420 |
| gctggcgaag | caatcagctt | cccaactacc | ctggggatga | caagtgcta | catccagatt | 480 |
| atggacctgg | ccacacatg | cgatgccacc | atgagctatg | agtgtccaat | gctggacgag | 540 |
| ggggtggaac | ccgacgatgt | cgattgctgg | tgtaatacaa | cttccacttg | ggtggtctac | 600 |
| ggcacctgtc | accataagaa | aggagaagct | cggcggagcc | ggagggcagt | gacactgcca | 660 |
| tcacacagca | ctaggaagct | gcagacacgc | agccagactt | ggctggagtc | cagagaatat | 720 |
| acaaaacatc | tgatcagagt | ggagaactgg | atcttccgga | atccaggatt | cgcactggct | 780 |
| gcagccgcta | tcgcatggct | gctgggcagc | tccacctctc | agaaagtgat | ctacctggtc | 840 |
| atgatcctgc | tgattgcccc | cgcttattct | atccgctgca | ttggggtgag | taatcgagac | 900 |
| ttcgtcgagg | aatgagcgg | cggacatgg | gtggatgtgg | tcctggaaca | cggaggctgc | 960 |
| gtgactgtga | tggctcagga | caagcctacc | gtggatatcg | agctggtgac | cacaactgtc | 1020 |
| tcaaacatgg | ccgaggtgag | gagctactgc | tatgaagcct | ccatttctga | catggctagt | 1080 |
| gattcacgct | gtccaaccca | gggcgaggcc | tacctggaca | gcagagtga | tacccagtac | 1140 |
| gtgtgcaaac | gaacactggt | cgaccggggc | tgggggaatg | gatgtggcct | gtttgggaag | 1200 |
| ggaagcctgg | tgacatgcgc | caaattcgct | tgttccaaga | aaatgactgg | caagtctatc | 1260 |
| cagcctgaga | acctggaata | caggattatg | ctgagcgtgc | acggatcaca | gcatagcggc | 1320 |
| atgatcgtca | cgacaccgg | ccacgagaca | gatgaaaatc | gagccaaagt | ggagattacc | 1380 |
| cctaactctc | caagagcaga | agccacactg | gggggatttg | gaagtctggg | cctggactgc | 1440 |
| gagccacgaa | ccggcctgga | cttctccgat | ctgtactatc | tgacaatgaa | caataagcac | 1500 |
| tggctggtgc | ataagaatg | gtttcacgac | atcccactgc | cctggcatgc | tggagcagat | 1560 |
| accggcacac | ctcactggaa | caataaggag | gccctggtgg | agttcaagga | tgcccatgct | 1620 |
| aaacggcaga | cagtggtcgt | gctggggagc | caggagggag | cagtgcacac | tgcactggcc | 1680 |
| ggcgctctgg | aggcagaaat | ggacggggcc | aagggaagac | tgtctagtgg | gcatctgaaa | 1740 |
| tgccggctga | agatggataa | actgagactg | aagggagtga | gctactccct | gtgcactgca | 1800 |
| gccttcactt | ttaccaaaat | cccagctgag | acactgcacg | gcacagtcac | tgtggaagtc | 1860 |
| cagtatgccg | gcactgacgg | ccccttgtaag | gtgcctgcac | agatggccgt | cgatatgcag | 1920 |
| accctgacac | cagtgggccg | gctgatcacc | gccaatcctg | tcattactga | gagtaccgaa | 1980 |
| aactcaaaaa | tgatgctgga | gctggaccccc | cctttttgggg | attcctatat | cgtgattggc | 2040 |

```
gtcggggaaa agaaaatcac acaccattgg caccggagcg gcagtacaat tgggaaggct    2100
tttgaggcaa ctgtgcgcgg cgccaaacga atggctgtcc tgggagacac cgcatgggat    2160
ttcggcagtg tgggaggggc tctgaactca ctgggaaagg gcatccatca gattttcgga    2220
gctgccttca agagcctgtt cggaggcatg tcctggttct ctcagatcct gattggcact    2280
ctgctgatgt ggctggggct gaacgccaag aatggcagca tcagtctgat gtgcctggcc    2340
ctgggggggg tcctgatttt cctgtcaacc gcagtctccg ctgactgatg a             2391
```

<210> SEQ ID NO 4
<211> LENGTH: 795
<212> TYPE: PRT
<213> ORGANISM: Artificial Sequence
<220> FEATURE:
<223> OTHER INFORMATION: Synthetic peptide

<400> SEQUENCE: 4

```
Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Thr Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300
```

```
Met Ser Gly Gly Thr Trp Val Asp Val Val Leu Glu His Gly Gly Cys
305                 310                 315                 320
Val Thr Val Met Ala Gln Asp Lys Pro Thr Val Asp Ile Glu Leu Val
                325                 330                 335
Thr Thr Thr Val Ser Asn Met Ala Glu Val Arg Ser Tyr Cys Tyr Glu
                340                 345                 350
Ala Ser Ile Ser Asp Met Ala Ser Asp Ser Arg Cys Pro Thr Gln Gly
            355                 360                 365
Glu Ala Tyr Leu Asp Lys Gln Ser Asp Thr Gln Tyr Val Cys Lys Arg
370                 375                 380
Thr Leu Val Asp Arg Gly Trp Gly Asn Gly Cys Gly Leu Phe Gly Lys
385                 390                 395                 400
Gly Ser Leu Val Thr Cys Ala Lys Phe Ala Cys Ser Lys Lys Met Thr
                405                 410                 415
Gly Lys Ser Ile Gln Pro Glu Asn Leu Glu Tyr Arg Ile Met Leu Ser
                420                 425                 430
Val His Gly Ser Gln His Ser Gly Met Ile Val Asn Asp Thr Gly His
                435                 440                 445
Glu Thr Asp Glu Asn Arg Ala Lys Val Glu Ile Thr Pro Asn Ser Pro
450                 455                 460
Arg Ala Glu Ala Thr Leu Gly Gly Phe Gly Ser Leu Gly Leu Asp Cys
465                 470                 475                 480
Glu Pro Arg Thr Gly Leu Asp Phe Ser Asp Leu Tyr Tyr Leu Thr Met
                485                 490                 495
Asn Asn Lys His Trp Leu Val His Lys Glu Trp Phe His Asp Ile Pro
                500                 505                 510
Leu Pro Trp His Ala Gly Ala Asp Thr Gly Thr Pro His Trp Asn Asn
                515                 520                 525
Lys Glu Ala Leu Val Glu Phe Lys Asp Ala His Ala Lys Arg Gln Thr
530                 535                 540
Val Val Val Leu Gly Ser Gln Glu Gly Ala Val His Thr Ala Leu Ala
545                 550                 555                 560
Gly Ala Leu Glu Ala Glu Met Asp Gly Ala Lys Gly Arg Leu Ser Ser
                565                 570                 575
Gly His Leu Lys Cys Arg Leu Lys Met Asp Lys Leu Arg Leu Lys Gly
                580                 585                 590
Val Ser Tyr Ser Leu Cys Thr Ala Ala Phe Thr Phe Thr Lys Ile Pro
                595                 600                 605
Ala Glu Thr Leu His Gly Thr Val Thr Val Glu Val Gln Tyr Ala Gly
610                 615                 620
Thr Asp Gly Pro Cys Lys Val Pro Ala Gln Met Ala Val Asp Met Gln
625                 630                 635                 640
Thr Leu Thr Pro Val Gly Arg Leu Ile Thr Ala Asn Pro Val Ile Thr
                645                 650                 655
Glu Ser Thr Glu Asn Ser Lys Met Met Leu Glu Leu Asp Pro Pro Phe
                660                 665                 670
Gly Asp Ser Tyr Ile Val Ile Gly Val Gly Glu Lys Lys Ile Thr His
                675                 680                 685
His Trp His Arg Ser Gly Ser Thr Ile Gly Lys Ala Phe Glu Ala Thr
                690                 695                 700
Val Arg Gly Ala Lys Arg Met Ala Val Leu Gly Asp Thr Ala Trp Asp
705                 710                 715                 720
Phe Gly Ser Val Gly Gly Ala Leu Asn Ser Leu Gly Lys Gly Ile His
```

|  |  |  | 725 |  |  |  | 730 |  |  |  | 735 |  |
|---|---|---|---|---|---|---|---|---|---|---|---|---|
| Gln | Ile | Phe | Gly | Ala | Ala | Phe | Lys | Ser | Leu | Phe | Gly | Gly | Met | Ser | Trp |
|  |  |  |  | 740 |  |  |  |  | 745 |  |  |  |  | 750 |  |

| Phe | Ser | Gln | Ile | Leu | Ile | Gly | Thr | Leu | Leu | Met | Trp | Leu | Gly | Leu | Asn |
|  |  | 755 |  |  |  |  | 760 |  |  |  |  | 765 |  |  |  |

| Ala | Lys | Asn | Gly | Ser | Ile | Ser | Leu | Met | Cys | Leu | Ala | Leu | Gly | Gly | Val |
|  | 770 |  |  |  |  | 775 |  |  |  |  | 780 |  |  |  |  |

| Leu | Ile | Phe | Leu | Ser | Thr | Ala | Val | Ser | Ala | Asp |
| 785 |  |  |  |  | 790 |  |  |  | 795 |  |